United States Patent
Takaku et al.

(10) Patent No.: US 12,404,264 B2
(45) Date of Patent: *Sep. 2, 2025

(54) ORGANIC ELECTRIC LIGHT EMITTING ELEMENT, MATERIAL FOR SAID ELEMENT, AND LIGHT EMITTING DEVICE, DISPLAY DEVICE, AND ILLUMINATION DEVICE EMPLOYING SAID ELEMENT

(71) Applicant: UDC IRELAND LIMITED, Dublin (IE)

(72) Inventors: Koji Takaku, Kanagawa (JP); Tetsu Kitamura, Kanagawa (JP); Wataru Sotoyama, Kanagawa (JP); Yasunori Yonekuta, Kanagawa (JP); Toru Watanabe, Kanagawa (JP); Toshihiro Ise, Kanagawa (JP); Saki Takada, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 928 days.

This patent is subject to a terminal disclaimer.

(21) Appl. No.: 16/662,143

(22) Filed: Oct. 24, 2019

(65) Prior Publication Data

US 2020/0058883 A1 Feb. 20, 2020

Related U.S. Application Data

(63) Continuation of application No. 14/237,764, filed as application No. PCT/JP2012/069691 on Aug. 2, 2012, now Pat. No. 10,468,607.

(30) Foreign Application Priority Data

Aug. 11, 2011 (JP) .................................. 2011-176340

(51) Int. Cl.
*H01L 51/00* (2006.01)
*C07D 209/86* (2006.01)
(Continued)

(52) U.S. Cl.
CPC ......... *C07D 403/04* (2013.01); *C07D 209/86* (2013.01); *C07D 209/88* (2013.01);
(Continued)

(58) Field of Classification Search
None
See application file for complete search history.

(56) References Cited

U.S. PATENT DOCUMENTS 10,468,607 B2 * 11/2019 Takaku ................ C07D 471/04
2004/0150352 A1 8/2004 Koide
(Continued)

FOREIGN PATENT DOCUMENTS

DE 102008035413 A1 2/2010
JP 2008311446 A 12/2008
(Continued)

OTHER PUBLICATIONS

Machine English translation of Nakatsuka (JP 2010-205986 A). Jul. 14, 2022.*
(Continued)

*Primary Examiner* — Jay Yang
(74) *Attorney, Agent, or Firm* — Riverside Law LLP

(57) ABSTRACT

An organic electroluminescent element including a substrate, a pair of electrodes including an anode and a cathode, disposed on the substrate, and at least one organic layer including a light emitting layer, disposed between the electrodes, in which the organic layer includes a compound represented by the following general formula, has high luminous efficiency, excellent blue color purity, and a small
(Continued)

change in the chromaticity due to deterioration by driving (Cy represents a fused aromatic ring structure having the number of constituent rings of 3 or more, and has $Dn^1$ and $Ac^1$ as different constituent rings, and each of the constituent rings are all hydrocarbon rings. $Dn^1$ represents $NR^{11}$, an O atom, or an S atom. $Ac^1$ represents an electron absorbing substituent, an aryl group having an electron absorbing substituent, or an electron deficient heteroaryl group. The ring $Z^1$ represents an arylene group or a heteroarylene group. $L^1$, $L^2$ and $L^3$ represent specific linking groups. u1 represents 0 or 1, and in the case where u1 is 1, the ring thus formed is not an aromatic ring. n1 and q1 represent 0 or 1, and in the case where any one of n1 and q1 is 0 and n1 or q1 is 1, the rings thus formed are not all aromatic rings. When $Ac^1$ is a pyridine ring, at least one of n1 and q1 is 1.)

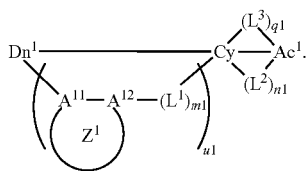

16 Claims, 1 Drawing Sheet

(51) Int. Cl.
| | |
|---|---|
| *C07D 209/88* | (2006.01) |
| *C07D 403/04* | (2006.01) |
| *C07D 405/04* | (2006.01) |
| *C07D 471/04* | (2006.01) |
| *C07D 487/04* | (2006.01) |
| *C07D 491/052* | (2006.01) |
| *C07D 491/16* | (2006.01) |
| *C09K 11/06* | (2006.01) |
| *H05B 33/10* | (2006.01) |
| *H10K 85/60* | (2023.01) |
| *H10K 50/11* | (2023.01) |
| *H10K 50/15* | (2023.01) |
| *H10K 50/16* | (2023.01) |
| *H10K 50/17* | (2023.01) |
| *H10K 50/18* | (2023.01) |

(52) U.S. Cl.
CPC ......... *C07D 405/04* (2013.01); *C07D 471/04* (2013.01); *C07D 487/04* (2013.01); *C07D 491/052* (2013.01); *C07D 491/16* (2013.01); *C09K 11/06* (2013.01); *H05B 33/10* (2013.01); *H10K 85/622* (2023.02); *H10K 85/6572* (2023.02); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 50/181* (2023.02)

(56) References Cited

U.S. PATENT DOCUMENTS

| | | |
|---|---|---|
| 2007/0231503 A1 | 10/2007 | Hwang |
| 2008/0124455 A1 | 5/2008 | Shin |
| 2010/0109517 A1 | 5/2010 | Fukushima |
| 2010/0252819 A1* | 10/2010 | Lecloux ............... C07C 211/54 |
| | | 257/E51.027 |
| 2012/0097929 A1 | 4/2012 | Kim |

FOREIGN PATENT DOCUMENTS

| | | | | |
|---|---|---|---|---|
| JP | 2010034458 A | | 2/2010 | |
| JP | 201087410 | | 4/2010 | |
| JP | 2010138121 | | 6/2010 | |
| JP | 2010205986 A | | 9/2010 | |
| JP | 2011051969 | | 3/2011 | |
| JP | 2011079822 A | * | 4/2011 | ............ C07C 13/62 |
| JP | 2011249539 | | 12/2011 | |
| JP | 2013532371 | | 8/2013 | |
| KR | 10-2011-0002155 | * | 1/2011 | |
| WO | 02060910 A1 | | 8/2002 | |
| WO | 2004065520 | | 8/2004 | |
| WO | 2010074520 A2 | | 7/2010 | |
| WO | 2011139125 | | 11/2011 | |

OTHER PUBLICATIONS

Machine English translation of Bae et al. (KR-10-2011-0002155). Feb. 15, 2023.*
Machine English translation of Kim et al. (JP-2011079822-A). Apr. 4, 2024.*
Machine English translation of Kim et al. (JP 2011-079822 A). Jul. 30, 2024.*
Machine English translation of Nakatsuka et al. (JP 2008-311446 A). Oct. 9, 2017.
Machine English translation of Kim et al. (JP 2011 -079822 A). May 6, 2017.
Machine English translation of Nakatsuka et al. (JP 2010-205986 A). May 6, 2017.
Yoshida, Masafumi et al., "High-Efficiency Carrier Injection Characteristics of Dixanthene Derivatives in Organic Light-Emitting Diodes." Japanese Journal of Applied Physics, 2005. vol. 44/No. 1A p. 410-411.

* cited by examiner

ORGANIC ELECTRIC LIGHT EMITTING ELEMENT, MATERIAL FOR SAID ELEMENT, AND LIGHT EMITTING DEVICE, DISPLAY DEVICE, AND ILLUMINATION DEVICE EMPLOYING SAID ELEMENT

CROSS-REFERENCE TO RELATED APPLICATIONS

This application is a continuation of pending U.S. application Ser. No. 14/237,764, filed May 13, 2014, now allowed, which is a U.S. national phase application filed under 35 U.S.C. § 371 claiming benefit to PCT International Patent Application No. PCT/JP2012/069691, filed on Aug. 2, 2012, which claims priority to Japanese Patent Application No. 2011-176340, filed Aug. 11, 2011, each of which applications is incorporated herein by reference in its entirety.

TECHNICAL FIELD

The present invention relates to an organic electroluminescent element and a material for an organic electroluminescent element used therefor. The present invention further relates to a light emitting device, a display device, or an illumination device using the organic electroluminescent element.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have an organic layer between a pair of electrodes, and utilize, for light emitting, energy of the exciton generated as a result of recombination of the electron injected from the cathode and the hole injected from the anode in the organic layer. The organic electroluminescent elements can provide elements having diverse light emitting wavelengths, and since they have a high response speed and are relatively thin and light-weight, it is expected that they can be employed in a wide range of applications. Above all, it is important to develop an organic electroluminescent element having high blue color purity and luminous efficiency in the applications in full-color displays and the like, and the outcomes have been reported of various research and development studies up to now.

For example, PTL 1 describes an organic electroluminescent element using a wide range of a fused polycyclic aromatic compounds containing a triazine group, in which an example of an organic electroluminescent element in which a compound having a substituted or unsubstituted triazine group substituted with a pyrene skeleton is mentioned, blue light emission is achieved with good luminous efficiency, and a long life span is attained. Further, PTLs 2 and 3 describe a compound in which a nitrogen atom is directly bonded to a pyrene skeleton to further form a fused ring structure, and PTLs 4 and 5 describe a compound in which a nitrogen atom is directly bonded to a fused polycyclic aromatic ring skeleton other than a pyrene skeleton to further form a fused ring structure, and in any case, the applications thereof in organic electroluminescent elements are described.

In addition, as a compound having further ring fusion with such a fused polycyclic aromatic ring, compounds having various structures are described in PTL 6, but in this literature, none of these compounds is expected to be excellent in luminous efficiency, color purity, or durability in an organic blue light emitting electroluminescent element.

CITATION LIST

Patent Literature

[PTL 1] JP-A-2010-138121
[PTL 2] JP-A-2011-51969
[PTL 3] JP-A-2011-79822
[PTL 4] WO2010/074520
[PTL 5] US2008/0124455 A1
[PTL 6] DE102008035413 (A1)

SUMMARY OF INVENTION

Technical Problem

However, the present inventors have investigated and have found that for the organic electroluminescent elements described in PTLs 1 to 5 above, there is a demand for further improvement of luminous efficiency. Further, it cannot be said that blue color purity of the organic electroluminescent element is also sufficient and it has been found that it is necessary to achieve higher blue color purity. It has also been found that if such an organic electroluminescent element is used for a long period of time, the chromaticity is changed due to deterioration by driving with a lowered luminous intensity (hereinafter also referred to as a change in the driving chromaticity). In addition, in PTL 6, there is a disclosure of a compound with its specific structure, in which rings are fused at two positions on a fused polycyclic aromatic ring, and the ring members to form the fused ring structures at the two positions are carbon atoms. It could be seen that there is a demand for an improvement of the luminous efficiency, the blue color purity, and the change in the driving chromaticity of this compound.

The present invention aims to solve the foregoing problems. It is an object of the present invention to provide an organic electroluminescent element having high luminous efficiency, excellent blue color purity, and a small change in the chromaticity due to deterioration by driving.

Solution to Problem

Therefore, the present inventors have conducted intensive studies so as to provide an organic electroluminescent element having high luminous efficiency, excellent blue color purity, and a small change in the chromaticity due to deterioration by driving. As a result, the present inventors have found that by using a compound in which at least two kinds of specific donor substituents and acceptor substituents are introduced into a fused polycyclic aromatic ring, the foregoing problems are solved, thereby providing the present invention as described below.

[1] An organic electroluminescent element including a substrate, a pair of electrodes including an anode and a cathode, disposed on the substrate, and at least one organic layer including a light emitting layer, disposed between the electrodes, in which the organic layer includes a compound represented by the following general formula (1).

[Chem. 1]

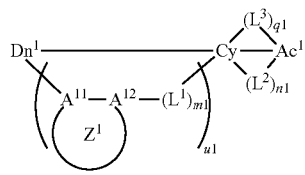

General formula (1)

(in which Cy represents a fused aromatic ring structure having the number of constituent rings of 3 or more, and has $Dn^1$ and $Ac^1$ as different constituent rings, and each of the constituent rings are all hydrocarbon rings. $Dn^1$ represents $NR^{11}$, an O atom, or an S atom, and in the case where u1 is 0, u1 further has a substituent. $R^{11}$ represents a substituent, and $R^{11}$ may be bonded to Cy to form a ring other than an aromatic ring. $Ac^1$ represents an electron absorbing substituent, an aryl group having an electron absorbing substituent, or an electron deficient heteroaryl group, and $Ac^1$ may further have a substituent. The ring $Z^1$ represents an arylene group or a heteroarylene group, $A^{11}$ represents a carbon atom constituting the ring $Z^1$, and $A^{12}$ represents a carbon atom or a nitrogen atom constituting the ring $Z^1$, $L^1$, $L^2$ and $L^3$ each independently represent an oxygen atom, a sulfur atom, $CR^{12}R^{13}$, or $SiR^{14}R^{15}$, and $R^{12}$, $R^{13}$, $R^{14}$ and $R^{15}$ each independently represent a hydrogen atom or a substituent. u1 represents 0 or 1, and in the case where u1 is 1, the ring formed by Cy, $Dn^1$, and the ring $Z^1$ is not an aromatic ring. m1 represents 0 or 1, and when m1 is 0 and u1 is 1, Cy and the ring $Z^1$ are directly bonded to each other. n1 and q1 represent 0 or 1, and in the case where any one of n1 and q1 is 0 and n1 or q1 is 1, the rings formed by Cy, $Ac^1$ and $L^2$ or $L^3$ are not all aromatic rings. However, when $Ac^1$ is a pyridine ring, at least one of n1 and q1 is 1.)

[2] In the organic electroluminescent element as described in [1], the Cy is preferably represented by pyrene, chrysene, fluoranthene, or phenanthrene, each of which may have a substituent, in the general formula (1).

[3] In the organic electroluminescent element as described in [1] or [2], the Cy is preferably represented by pyrene which may have a substituent, has any one of the $Dn^1$ and the $Ac^1$ at the 1- or 3-position of the pyrene, and has the other of the $Dn^1$ and the $Ac^1$ at the 6- or 8-position of the pyrene, in the general formula (1).

[4] In the organic electroluminescent element as described in anyone of [1] to [3], the compound represented by the general formula (1) is preferably a compound represented by any one of the following general formulae (2) to (5).

[Chem. 2]

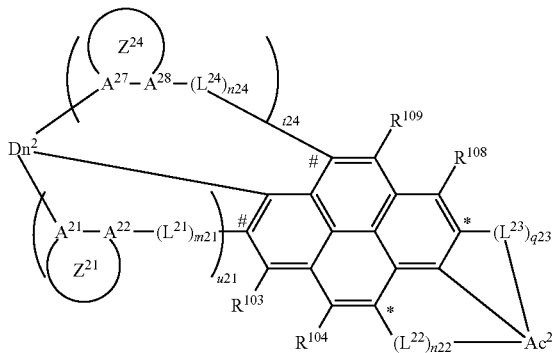

General formula (2)

(in which in the case where $Dn^2$ represents an N atom, an O atom, or an S atom and $Dn^2$ represents an O atom or an S atom, the sum of u21 and t24 is 0 or 1. When in the case where $Dn^2$ represents an N atom, at least one of u21 and t24 represents 0, or when in the case where $Dn^2$ represents an O atom or an S atom, u21 and t24 are both 0, $Dn^2$ further has a substituent. $Ac^2$ represents an electron absorbing substituent, an aryl group having an electron absorbing substituent, or an electron deficient heteroaryl group, and Ac may further have a substituent. The ring $Z^{21}$ and the ring $Z^{24}$ each independently represent an arylene group or a heteroarylene group, $A^{21}$ represents a carbon atom constituting the ring $Z^1$, $A^2$ represents a carbon atom or a nitrogen atom constituting the ring $Z^{21}$, $A^2$ represents a carbon atom constituting the ring $Z^{24}$, and $A^{28}$ represents a carbon atom or a nitrogen atom constituting the ring $Z^{24}$. $R^{103}$, $R^{104}$, $R^{108}$ and $R^{109}$ each independently represent a hydrogen atom or a substituent. $L^{21}$, $L^{22}$, $L^{23}$ and $L^{24}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #positions of the pyrene ring and $Dn^2$ are not bonded to each other, and in the case where u21 is 1, the ring formed by the pyrene ring, $Dn^2$, and the ring $Z^{21}$ is not an aromatic ring. t24 represents 0 or 1, in the case where t24 is 0, the #positions of the pyrene ring and $Dn^2$ are not bonded to each other, and in the case where t24 is 1, the ring formed by the pyrene ring, $Dn^2$, and the ring $Z^{24}$ is not an aromatic ring. m21 represents 0 or 1, and when m21 is 0 and u21 is 1, the #positions of the pyrene ring and the ring $Z^{21}$ are directly bonded to each other. s24 represents 0 or 1, and when s24 is 0 and u24 is 1, the #positions of the pyrene ring and the ring $Z^{24}$ are directly bonded to each other. n22 and q23 represent 0 or 1, in the case where any one of n22 and q23 is 0 and n22 or q23 is 1, the rings formed by the pyrene ring, $Ac^2$ and $L^{22}$ or $L^{23}$ are not all aromatic rings. In the case where n22 or q23 is 0, the * positions of the pyrene ring and $Ac^2$ are not bonded to each other. However, when $Ac^2$ is a pyridine ring, at least one of n22 and q23 is 1.)

[Chem. 3]

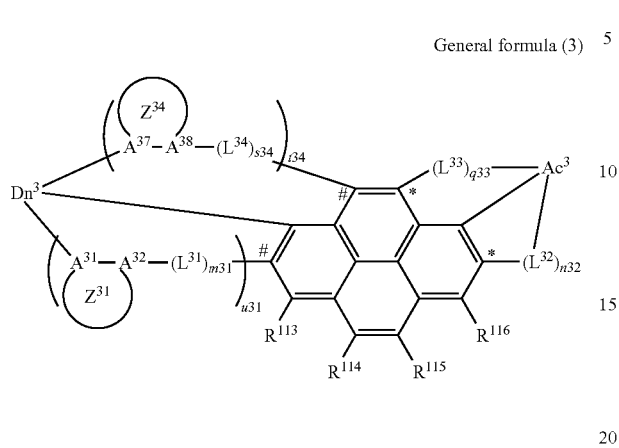

General formula (3)

[Chem. 4]

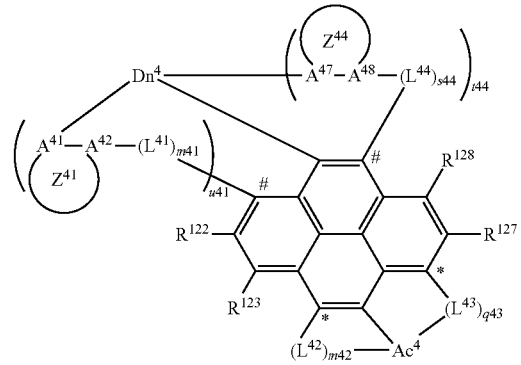

General formula (4)

(in which $Dn^3$ represents an N atom, an O atom, or an S atom, and in the case where $Dn^3$ represents an O atom or an S atom, the sum of u31 and t34 is 0 or 1. When in the case where $Dn^3$ represents an N atom, at least one of u31 and t34 represents 0, or when in the case where $Dn^3$ represents an O atom or an S atom and u31 and t34 are both 0, $Dn^3$ further has a substituent. $Ac^3$ represents an electron absorbing substituent, an aryl group having an electron absorbing substituent, or an electron deficient heteroaryl group, and $Ac^3$ may further have a substituent. The ring $Z^{31}$ and the ring $Z^{34}$ each independently represent an arylene group or a heteroarylene group, $A^{31}$ represents a carbon atom constituting the ring $Z^{31}$, and $A^{32}$ represents a carbon atom or a nitrogen atom constituting the ring $Z^{31}$, $A^{37}$ represents a carbon atom constituting the ring $Z^{34}$, and $A^3a$ represents a carbon atom or a nitrogen atom constituting the ring $Z^{34}$. $R^{113}$, $R^{114}$, $R^{115}$ and $R^{116}$ each independently represent a hydrogen atom or a substituent. $L^3$, $L^{32}$, $L^{33}$ and $L^{34}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, in the case where u31 is 0, the #position of the pyrene ring and $Dn^3$ are not bonded to each other, and in the case where u31 is 1, the ring formed by the pyrene ring, $Dn^3$ and the ring $Z^{31}$ is not an aromatic ring. t34 represents 0 or 1, in the case where t34 is 0, the #positions of the pyrene ring and $Dn^3$ are not bonded to each other, and in the case where t34 is 1, the ring formed by pyrene ring, $Dn^3$ and the ring $Z^{34}$ is not an aromatic ring. m31 represents 0 or 1, and when m31 is 0 and u31 is 1, the #positions of the pyrene ring and the ring $Z^{31}$ are directly bonded to each other. m34 represents 0 or 1 and when m34 is 0 and t34 is 1, the #positions of the pyrene ring and the ring $Z^{34}$ are directly bonded to each other. n32 and q33 represent 0 or 1, and in the case where any one of n32 and q33 is 0 and n32 or q33 is 1, the rings formed by the pyrene ring, $Ac^3$ and $L^{32}$ or $L^{33}$ are not all aromatic rings. In the case where n32 or q33 is 0, the * positions of the pyrene ring and $Ac^3$ are not bonded to each other. However, when $Ac^3$ is a pyridine ring, at least one of n32 and q33 is 1.)

(in which $Dn^4$ represents an N atom, an O atom, or an S atom, and in the case where $Dn^4$ represents an O atom or an S atom, the sum of u41 and t44 is 0 or 1. When in the case where $Dn^4$ represents an N atom and at least one of u41 and t44 represents 0, or when in the case where $Dn^4$ represents an O atom or an S atom, u41 and t44 are both 0, $Dn^4$ further has a substituent. $Ac^4$ represents an electron absorbing substituent, an aryl group having an electron absorbing substituent, or an electron deficient heteroaryl group, and $Ac^4$ may further have a substituent. The ring $Z^{41}$ and the ring $Z^{44}$ each independently represent an arylene group or a heteroarylene group, $A^{41}$ represents a carbon atom constituting the ring $Z^{41}$, $A^{42}$ represents a carbon atom or a nitrogen atom constituting the ring $Z^{41}$, $A^{47}$ represents a carbon atom constituting the ring $Z^{44}$, and $A^{48}$ represents a carbon atom or a nitrogen atom constituting the ring $Z^{44}$. $R^2$, $R^3$, $R^7$ and $R^8$ each independently represent a hydrogen atom or a substituent. $L^4$, $L^{42}$, $L^{43}$ and $L^{44}$ each independently represent an oxygen atom, a sulfur atom, $CR^{42}R^{43}$, or $SiR^{44}R^{45}$, and $R^{42}$, $R^{43}$, $R^{44}$ and $R^{45}$ each independently represent a hydrogen atom or a substituent. u41 represents 0 or 1, in the case where u41 is 0, the #positions of the pyrene ring and $Dn^4$ are not bonded to each other, and in the case where u41 is 1, the ring formed by the pyrene ring, $Dn^4$ and the ring $Z^{41}$ is not an aromatic ring. t44 represents 0 or 1, in the case where t44 is 0, the #positions of the pyrene ring and $Dn^4$ are not bonded to each other, and in the case where t44 is 1, the ring formed by the pyrene ring, $Dn^4$ and the ring $Z^{44}$ is not an aromatic ring. m41 represents 0 or 1, and when m41 is 0 and u41 is 1, the #positions of the pyrene ring and the ring $Z^{41}$ are directly bonded to each other. m44 represents 0 or 1, and when m44 is 0 and t44 is 1, the #positions of the pyrene ring and the ring $Z^{44}$ are directly bonded to each other. n42 and q43 represent 0 or 1, and in the case where any one of n42 and q43 is 0 and n42 or q43 is 1, the rings formed by the pyrene ring, $Ac^4$ and $L^{42}$ or $L^{43}$ are not all aromatic rings. In the case where n42 or q43 is 0, the * positions of the pyrene ring and $Ac^4$ are not bonded to each other. However, when $Ac^4$ is a pyridine ring, at least one of n42 and q43 is 1.)

[Chem. 5]

General formula (5)

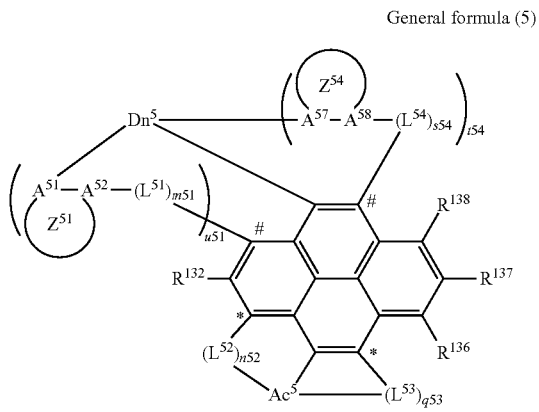

(in which $Dn^5$ represents an N atom, an O atom, or an S atom, in the case where $Dn^5$ represents an O atom or an S atom, the sum of u51 and t54 is 0 or 1. When in the case where $Dn^5$ represents an N atom, at least one of u51 and t54 represents 0, or when in the case where $Dn^5$ represents an O atom or an S atom, u51 and t54 are both 0, $Dn^5$ further has a substituent. $Ac^5$ represents an electron absorbing substituent, an aryl group having an electron absorbing substituent, or an electron deficient heteroaryl group, $Ac^5$ may further have a substituent. The ring $Z^{51}$ and the ring $Z^{54}$ each independently represent an arylene group or a heteroarylene group, $A^{51}$ represents a carbon atom constituting the ring $Z^{51}$, $A^{52}$ represents a carbon atom or a nitrogen atom constituting the ring $Z^{51}$, $A^{57}$ represents a carbon atom constituting the ring $Z^{54}$, and $A^{58}$ represents a carbon atom or a nitrogen atom constituting the ring $Z^{54}$. $R^2$, $R^6$, $R^7$ and $R^8$ each independently represent a hydrogen atom or a substituent. $L^{51}$, $L^{52}$, $L^{53}$ and $L^{54}$ each independently represent an oxygen atom, a sulfur atom, $CR^{52}R^{53}$, or $SiR^{54}R^{55}$, and $R^{52}$, $R^{53}$, $R^{54}$ and $R^{55}$ each independently represent a hydrogen atom or a substituent. u51 represents 0 or 1, in the case where u51 is 0, the #positions of the pyrene ring and $Dn^5$ are not bonded to each other, and in the case where u51 is 1, the ring formed by the pyrene ring, $Dn^5$ and the ring $Z^{51}$ is not an aromatic ring. t54 represents 0 or 1, in the case where t54 is 0, the #positions of the pyrene ring and $Dn^5$ are not bonded to each other, and in the case where t54 is 1, the ring formed by the pyrene ring, $Dn^5$ and the ring $Z^{54}$ is not an aromatic ring. m51 represents 0 or 1, and when m51 is 0 and u51 is 1, the #positions of the pyrene ring and the ring $Z^{51}$ are directly bonded to each other. m54 represents 0 or 1, and when m54 is 0 and t54 is 1, the #positions of the pyrene ring and the ring $Z^{54}$ are directly bonded to each other. n52 and q53 represent 0 or 1, and in the case where any one of n52 and q53 is 0 and n52 or q53 is 1, the rings formed by the pyrene ring, $Ac^5$ and $L^{52}$ or $L^{53}$ are not all aromatic rings. In the case where n52 or q53 is 0, the * positions of the pyrene ring and $Ac^5$ are not bonded to each other. However, when $Ac^5$ is a pyridine ring, at least one of n52 and q53 is 1.)

[5] In the organic electroluminescent element as described in [4], the compound represented by the general formula (1) is preferably the compound represented by the general formula (2).

[6] In the organic electroluminescent element as described in [5], the compound represented by the general formula (2) is preferably a compound represented by the following general formula (6).

[Chem. 6]

General formula (6)

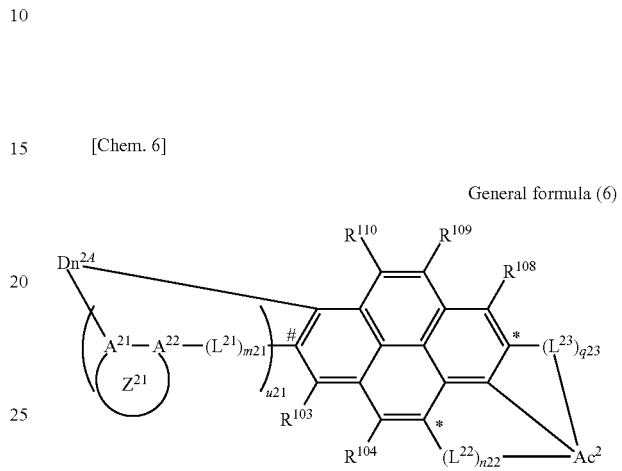

(in which $Dn^{24}$ represents $NR^{114}$, an O atom, or an S atom, and when u21 represents 0, $Dn^{24}$ further has a substituent. $R^{114}$ represents a substituent. $Ac^2$ represents an electron absorbing substituent, an aryl group having an electron absorbing substituent, or an electron deficient heteroaryl group, $Ac^2$ may further have a substituent. The ring $Z^{21}$ represents an arylene group or a heteroarylene group, $A^{21}$ represents a carbon atom constituting the ring $Z^{21}$, $A^{22}$ represents a carbon atom or a nitrogen atom constituting the ring $Z^{21}$. $R^{103}$, $R^{104}$, $R^{108}$, $R^{109}$ and $R^{110}$ each independently represent a hydrogen atom or a substituent. $L^{21}$, $L^{22}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #positions of the pyrene ring and $Dn^{24}$ are not bonded to each other, and in the case where u21 is 1, the ring formed by the pyrene ring, $Dn^{24}$ and the ring $Z^{21}$ is not an aromatic ring, m21 represents 0 or 1, and when m21 is 0 and u21 is 1, the #positions of the pyrene ring and the ring $Z^{21}$ are directly bonded to each other. n22 and q23 represent 0 or 1, and in the case where any one of n22 and q23 is 0 and n22 or q23 is 1, the rings formed by the pyrene ring, $Ac^2$ and $L^{22}$ or $L^{23}$ are not all aromatic rings. In the case where n22 or q23 is 0, the * positions of the pyrene ring and $Ac^2$ are not bonded to each other. However, when $Ac^2$ is a pyridine ring, at least one of n22 and q23 is 1.)

[7] In the organic electroluminescent element as described in [6], the compound represented by the general formula (6) is preferably a compound represented by the following general formula (8).

[Chem. 7]

General formula (8)

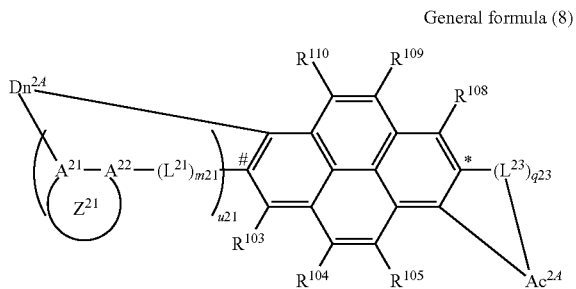

(in which $Dn^{24}$ represents $NR^{114}$, an O atom, or an S atom, and when u21 represents 0, $Dn^{24}$ further has a substituent. $R^{114}$ represents a substituent. $Ac^{24}$ represents an electron absorbing substituent, an aryl group having an electron absorbing substituent, or an electron deficient heteroaryl group, $Ac^{24}$ may further have a substituent. The ring $Z^{21}$ represents an arylene group or a heteroarylene group, $A^{21}$ represents a carbon atom constituting the ring $Z^{21}$, and $A^{22}$ represents a carbon atom or a nitrogen atom constituting the ring $Z^{21}$. $R^{103}$, $R^{104}$, $R^{105}$, $R^{108}$, $R^{109}$ and $R^{110}$ each independently represent a hydrogen atom or a substituent. $L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #positions of the pyrene ring and $Dn^{24}$ are not bonded to each other, and in the case where u21 is 1, the ring formed by the pyrene ring, $Dn^{24}$ and the ring $Z^{21}$ is not an aromatic ring. m21 represents 0 or 1, when m21 is 0 and u21 is 1, the #positions of the pyrene ring and the ring $Z^{21}$ are directly bonded to each other. q23 represents 0 or 1, and in the case where q23 is 1, the rings formed by the pyrene ring, $Ac^{24}$ and $L^{23}$ are not all aromatic rings. In the case where q23 is 0, the * positions of the pyrene ring and $Ac^{24}$ are not bonded to each other. However, when $Ac^{24}$ is a pyridine ring, q23 is 1.)

[8] In the organic electroluminescent element as described in [7], the compound represented by the general formula (8) is preferably a compound represented by the following general formula (10).

[Chem. 8]

General formula (10)

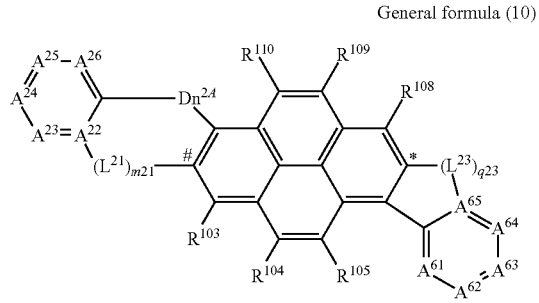

(in which $Dn^{24}$ represents $NR^{114}$, an O atom, or an S atom, and $R^{114}$ represents a substituent. $A^{22}$, $A^{23}$, $A^{24}$, $A^{25}$, $A^{26}$, $A^{61}$, $A^{62}$, $A^{63}$, $A^{64}$ and $A^{65}$ each independently represent CRzs (Rz represents a hydrogen atom or a substituent, and two adjacent CRzs may be combined with each other to form a 5- or 6-membered ring) or an N atom. In the case where $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent. $R^{103}$, $R^{104}$, $R^{105}$, $R^{108}$, $R^{109}$ and $R^{110}$ each independently represent a hydrogen atom or a substituent. $L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. m21 represents 0 or 1, and when m21 is 0, the #positions of the pyrene ring and $A^{22}$ are directly bonded to each other. q23 represents 0 or 1, and in the case where q23 is 0, the * positions of the pyrene ring and $A^{65}$ are not bonded to each other. However, in the case where only one of $A^{61}$, $A^{62}$, $A^{63}$, $A^{64}$ and $A^{65}$ is an N atom, q23 represents 1.)

[9] In the organic electroluminescent element as described in [8], the compound represented by the general formula (10) is preferably a compound represented by the following general formula (12).

[Chem. 9]

General formula (12)

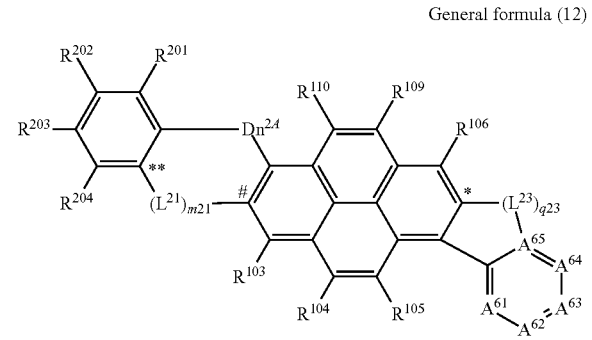

(in which $Dn^{24}$ represents $NR^{114}$, an O atom, or an S atom, and $R^{114}$ represents a substituent. $A^{61}$, $A^{62}$, $A^{63}$, $A^{64}$ and $A^{65}$ each independently represent CRzs (Rz represents a hydrogen atom or a substituent, and two adjacent CRzs may be combined with each other to form a 5- or 6-membered ring) or an N atom. In the case where $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent. $R^{103}$, $R^{104}$, $R^{105}$, $R^{108}$, $R^{109}$, $R^{110}$, $R^{201}$, $R^{202}$, $R^{203}$ and $R^{204}$ each independently represent a hydrogen atom or a substituent. $L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. m21 represents 0 or 1, and when m21 is 0, the ** position and the #position of the pyrene ring are directly bonded to each other. q23 represents 0 or 1, and in the case where q23 is 0, the * positions of the pyrene ring and $A^{65}$ are not bonded to each other. However, in the case where only one of $A^{61}$, $A^{62}$, $A^{63}$, $A^{64}$ and $A^{65}$ is an N atom, q23 is 1.)

[10] In the organic electroluminescent element as described in any one of [5] to [9], the q23 of the compound represented by the general formula (2) is preferably 1.

[11] In the organic electroluminescent element as described in [4], the compound represented by the general formula (1) is preferably the compound represented by the general formula (3).

[12] In the organic electroluminescent element as described in [11], the compound represented by the general formula (3) is preferably a compound represented by the following general formula (7).

[Chem. 10]

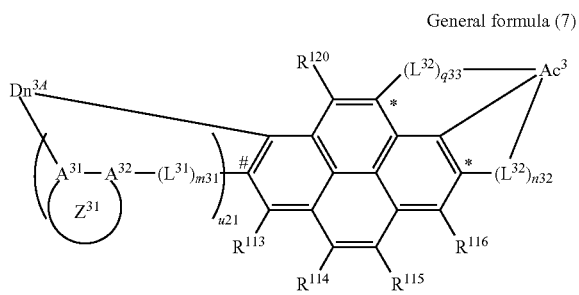

General formula (7)

(in which $Dn^{3A}$ represents $NR^{11B}$, an O atom, or an S atom, and when u31 represents 0, $Dn^{3A}$ further has a substituent. $R^{11B}$ represents a substituent. $Ac^3$ represents an electron absorbing substituent, an aryl group having an electron absorbing substituent, or an electron deficient heteroaryl group, $Ac^3$ may further have a substituent. The ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$. $R^{113}$, $R^{114}$, $R^{115}$, $R^{116}$ and $R^{120}$ each independently represent a hydrogen atom or a substituent. $L^{31}$, $L^{32}$ and $L^{33}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, and in the case where u31 is 0, the #positions of the pyrene ring and $Dn^{3A}$ are not bonded to each other, and in the case where u31 is 1, the ring formed by the pyrene ring, $Dn^{3A}$ and the ring $Z^{31}$ is not an aromatic ring. m31 represents 0 or 1, and when m31 is 0 and u31 is 1, the #positions of the pyrene ring and the ring $Z^{31}$ are directly bonded to each other. n32 and q33 represent 0 or 1, and in the case where any one of n32 and q33 is 0 and n32 or q33 is 1, the rings formed by the pyrene ring, $Ac^3$ and $L^{32}$ or $L^{33}$ are not all aromatic rings. In the case where n32 or q33 is 0, the * positions of the pyrene ring and $Ac^3$ are not bonded to each other. However, when $Ac^3$ is a pyridine ring, at least one of n32 and q33 is 1.)

[13] In the organic electroluminescent element as described in [12], the compound represented by the general formula (7) is preferably a compound represented by the following general formula (9).

[Chem. 11]

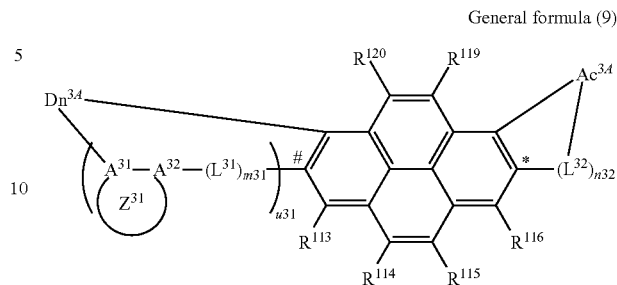

General formula (9)

(in which $Dn^{3A}$ represents $NR^{11B}$, an O atom, or an S atom, and when u31 represents 0, $Dn^{3A}$ further has a substituent. $R^{11B}$ represents a substituent. $Ac^{3A}$ represents an electron absorbing substituent, an aryl group having an electron absorbing substituent, or an electron deficient heteroaryl group, $Ac^{3A}$ may further have a substituent. The ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$. $R^{113}$, $R^{114}$, $R^{115}$, $R^{116}$, $R^{119}$ and $R^{120}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, and in the case where u31 is 0, the #positions of the pyrene ring and $Dn^{3A}$ are not bonded to each other, and in the case where u31 is 1, the ring formed by the pyrene ring, $Dn^{3A}$ and the ring $Z^{31}$ is not an aromatic ring. m31 represents 0 or 1, and when m31 is 0 and u31 is 1, the #positions of the pyrene ring and the ring $Z^{31}$ are directly bonded to each other. n32 represents 0 or 1, and in the case where n32 is 1, the rings formed by the pyrene ring, $Ac^{3A}$ and $L^{32}$ are not all aromatic rings. In the case where n32 is 0, the * positions of the pyrene ring and $Ac^{3A}$ are not bonded to each other. However, when $Ac^{3A}$ is a pyridine ring, n32 is 1.)

[14] In the organic electroluminescent element as described in [13], the compound represented by the general formula (9) is preferably a compound represented by the following general formula (11).

[Chem. 12]

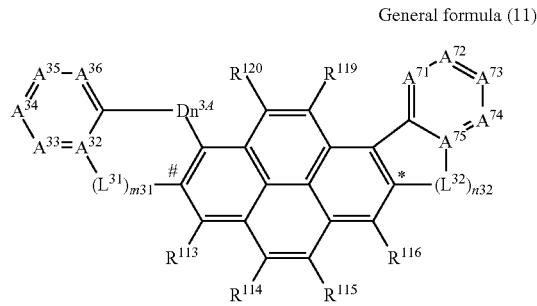

General formula (11)

(in which $Dn^{3A}$ represents $NR^{11B}$, an O atom, or an S atom, and $R^{11B}$ represents a substituent. $A^{32}$, $A^{33}$, $A^{34}$, $A^{35}$, $A^{36}$, $A^{71}$, $A^{72}$, $A^{73}$, $A^{74}$ and $A^{75}$ each independently represent CRz' (two adjacent CRz's may be combined with each other to form a 5- or 6-membered ring) or an N atom. In the case where $A^{71}, A^{72}, A^{73}, A^{74}$ and $A^{75}$ are not all N atoms, at least one Rz' in CRz's represented by $A^{71}, A^{72}, A^{73}, A^{74}$ and $A^{75}$ represents an electron absorbing substituent. $R^{113}, R^{114}, R^{115}, R^{116}, R^{119}$ and $R^{120}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}, R^{33}, R^{34}$ and $R^{35}$ each independently represent a hydrogen atom or a substituent. m31 represents 0 or 1, and when m31 is 0, the #positions of the pyrene ring and $A^{32}$ are directly bonded to each other. n32 represents 0 or 1, and in the case where n32 is 1, the rings formed by the pyrene ring, $Ac^{34}$ and $L^{32}$ are not all aromatic rings. In the case where n32 is 0, the * positions of the pyrene ring and $A^{75}$ are not bonded to each other. However, in the case where only one of $A^{71}, A^{72}, A^{73}, A^{74}$ and $A^{75}$ is an N atom, n32 represents 1.)

[15] In the organic electroluminescent element as described in [14], the compound represented by the general formula (11) is preferably a compound represented by the following general formula (13).

[Chem. 13]

General formula (13)

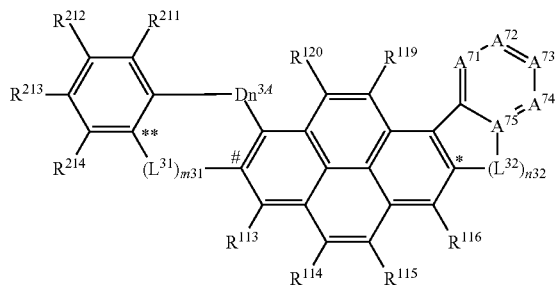

(in which $Dn^{34}$ represents $NR^{11B}$, an O atom, or an S atom, and $R^{11B}$ represents a substituent. $A^{71}, A^{72}, A^{73}, A^{74}$ and $A^{75}$ each independently represent CRz' (two adjacent CRz's may be combined with each other to form a 5- or 6-membered ring) or an N atom. In the case where $A^{71}, A^{72}, A^{73}, A^{74}$ and $A^{75}$ are not all N atoms, at least one Rz' in CRz's represented by $A^{71}, A^{72}, A^{73}, A^{74}$ and $A^{75}$ represents an electron absorbing substituent. $R^{113}, R^{114}, R^{115}, R^{116}, R^{119}, R^{120}, R^{211}, R^{212}, R^{213}$ and $R^{214}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}, R^{33}, R^{34}$ and $R^{35}$ each independently represent a hydrogen atom or a substituent. m31 represents 0 or 1, and when m31 is 0, the ** position and the #position of the pyrene ring are directly bonded to each other. n32 represents 0 or 1, and in the case where n32 is 0, the * position of the pyrene ring and $A^{75}$ are not bonded to each other. However, in the case where only one of $A^{71}, A^{72}, A^{73}, A^{74}$ and $A^{75}$ is an N atom, n32 represents 1.)

[16] In the organic electroluminescent element as described in any one of [11] to [15], the n32 of the compound represented by the general formula (3) is preferably 1.

[17] In the organic electroluminescent element as described in any one of [1] to [16], the molecule weight of the compound represented by the general formula (1) is preferably 800 or less.

[18] In the organic electroluminescent element as described in any one of [1] to [17], at least one organic layer including the compound represented by the general formula (1) is preferably the light emitting layer.

[19] In the organic electroluminescent element as described in any one of [1] to [18], the compound represented by the general formula (1) is preferably a light emitting material.

[20] In the organic electroluminescent element as described in any one of [1] to [19], the light emitting layer preferably includes an anthracene-based host material.

[21] In the organic electroluminescent element as described in any one of [1] to [20], the light emitting layer is preferably formed by a vacuum deposition process.

[22] In the organic electroluminescent element as described in any one of [1] to [20], the light emitting layer is preferably formed by a wet process.

[23] A light emitting device using the organic electroluminescent element as described in any one of [1] to [22].

[24] A display device using the organic electroluminescent element as described in any one of [1] to [23].

[25] An illumination device using the organic electroluminescent element as described in any one of [1] to [24].

[26] A material for an organic electroluminescent element, which is represented by the following general formula (1).

[Chem. 14]

General formula (1)

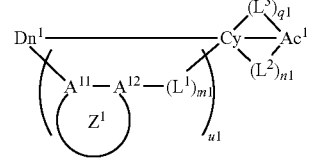

(in which Cy represents a fused aromatic ring structure having the number of constituent rings of 3 or more, and has $Dn^1$ and $Ac^1$ as different constituent rings, and each of the constituent rings are all hydrocarbon rings. $Dn^1$ represents $NR^{11}$, an O atom, or an S atom, and in the case where u1 is 0, u1 further has a substituent. $R^{11}$ represents a substituent, and $R^{11}$ may be bonded to Cy to form a ring other than an aromatic ring. $Ac^1$ represents an electron absorbing substituent, an aryl group having an electron absorbing substituent, or an electron deficient heteroaryl group, and $Ac^1$ may further have a substituent. The ring $Z^1$ represents an arylene group or a heteroarylene group, $A^{11}$ represents a carbon atom constituting the ring $Z^1$, and $A^{12}$ represents a carbon atom or a nitrogen atom constituting the ring $Z^1$. $L^1, L^2$ and $L^3$ each independently represent an oxygen atom, a sulfur atom, $CR^{12}R^{13}$, or $SiR^{14}R^{15}$, and $R^{12}, R^{13}, R^{14}$ and $R^{15}$ each independently represent a hydrogen atom or a substituent, u1 represents 0 or 1, and in the case where u1 is 1, the ring formed by Cy, $Dn^1$, and the ring $Z^1$ is not an aromatic ring, m1 represents 0 or 1, and when m1 is 0 and u1 is 1, Cy and the ring $Z^1$ are directly bonded to each other, n1 and q1 represent 0 or 1, and in the case where any one of n1 and q1 is 0 and n1 or q1 is 1, the rings formed by Cy, Ac$^1$ and L$^2$ or L$^3$ are not all aromatic rings. However, when Ac$^1$ is a pyridine ring, at least one of n1 and q1 is 1.)

Advantageous Effects of Invention

The organic electroluminescent element of the present invention has an advantageous effect that the luminous efficiency is high, the blue color purity is excellent, and the change in the chromaticity due to deterioration by driving is small. Further, when the compound of the present invention is used, such an excellent organic electroluminescent element can be easily prepared. Further, the light emitting device, the display device, and the illumination device of the present invention have advantageous effects in that the power consumption is low and the blue color purity is excellent, but the chromaticity is not easily changed even with a long-term use.

DESCRIPTION OF EMBODIMENTS

Figure 1:
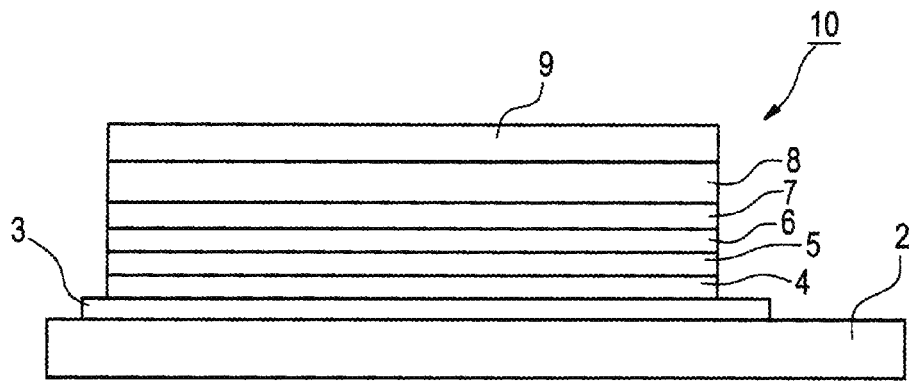
FIG. 1 is a schematic view showing one example of a configuration of the organic electroluminescent element according to the present invention.

Hereinafter, the details of the present invention will be described. The description of the configuration requirements as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Material for Organic Electroluminescent Element, Represented by General Formula (1)]

The organic electroluminescent element of the present invention has a substrate, a pair of electrodes including an anode and a cathode, disposed on the substrate, and at least one organic layer including a light emitting layer, disposed between the electrodes, in which the organic layer includes a compound represented by the following general formula (1).

[Chem. 15]

General formula (1)

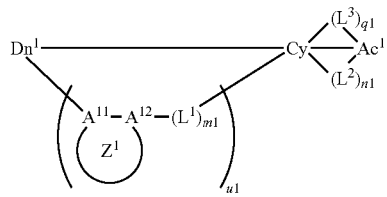

(in which Cy represents a fused aromatic ring structure having the number of constituent rings of 3 or more, and has Dn$^1$ and Ac$^1$ as different constituent rings, and each of the constituent rings are all hydrocarbon rings.

Dn$^1$ represents NR$^{11}$, an O atom, or an S atom, and in the case where u1 is 0, u1 further has a substituent. R$^{11}$ represents a substituent, and R$^{11}$ may be bonded to Cy to form a ring other than an aromatic ring. Ac$^1$ represents an electron absorbing substituent, an aryl group having an electron absorbing substituent, or an electron deficient heteroaryl group, and Ac$^1$ may further have a substituent. The ring Z$^1$ represents an arylene group or a heteroarylene group, A$^{11}$ represents a carbon atom constituting the ring Z$^1$, and A$^{12}$ represents a carbon atom or a nitrogen atom constituting the ring Z$^1$. L$^1$, L$^2$ and L$^3$ each independently represent an oxygen atom, a sulfur atom, CR$^{12}$R$^{13}$, or SiR$^{14}$R$^{15}$, and R$^{12}$, R$^{13}$, R$^{14}$ and R$^{15}$ each independently represent a hydrogen atom or a substituent, u1 represents 0 or 1, and in the case where u1 is 1, the ring formed by Cy, Dn$^1$, and the ring Z$^1$ is not an aromatic ring, m1 represents 0 or 1, and when m1 is 0 and u1 is 1, Cy and the ring Z$^1$ are directly bonded to each other, n1 and q1 represent 0 or 1, and in the case where any one of n1 and q1 is 0 and n1 or q1 is 1, the rings formed by Cy, Ac$^1$ and L$^2$ or L$^3$ are not all aromatic rings. However, when Ac$^1$ is a pyridine ring, at least one of n1 and q1 is 1.)

When the organic electroluminescent element of the present invention includes the compound represented by the general formula (1) in an organic layer, the luminous spectrum is sharp and the blue color purity is good. In the organic electroluminescent element of the present invention, at least one organic layer including the compound represented by the general formula (1) is preferably a light emitting layer. It is known that in order to obtain good blue color purity, it is useful to shorten the light emitting wavelength. However, when the light emitting wavelength of the light emitting material is shortened, the S$_1$ (lowest excited singlet energy level) of light emitting material increases, and thus, the difference between the S$_1$ of the light emitting material and the S$_1$ of the host material decreases, or the S$_1$ of the host material becomes larger than the S$_1$ of the light emitting material. As a result, the problems that the luminous efficiency is lowered and the sub-light emission of the host material is mixed, leading to lowered blue color purity. To the contrary, when the compound represented by the general formula (1) is used according to the present invention, the spectrum can be sharpened and the blue color purity can be improved, while achieving high luminous efficiency.

Not wishing to be restricted to any theory, such a change in the luminous spectrum of the compound represented by the general formula (1) is sharpened, but first, for a skeleton having a fused aromatic ring structure having the number of constituent rings of 3 or more and each of the constituent rings being a hydrocarbon ring, by introducing a donor substituent which is NR$^{11}$, an O atom, or an S atom, and an acceptor substituent which is an electron absorbing substituent, an aryl group having an electron absorbing substituent, or an electron deficient heteroaryl group in a specific embodiment, the bias of the charges in the molecule causes a small change in the structures between the ground state and the exciton state, and the luminous spectrum can be more sharpened that the compounds known in the related art. As a compound similar to those compounds, the compounds 13 to 15 in which a pyridine ring is introduced into a pyrene ring are described in JP-A-2011-79822, which were insufficient as an acceptor group contributing the bias of the charge distribution in the molecule even with the introduction of the pyridine ring, and the effects of the present invention, such as a sharpened luminous spectrum, were insufficient, in fact.

The compound of the present invention represented by the general formula (1) is stable against holes (oxidation) or electrons (reduction), has a high charge injecting or transporting property. With the compound, the association among the pyrene rings does not easily occur and the chemical reaction deterioration by element driving does not easily occur. As a result, the change in the chromaticity due to deterioration by driving does not easily occur, either.

Hereinafter, preferred structures of the compound represented by the general formula (1) will be described.

In the present invention, the hydrogen atom in the description of the general formula (1) also includes isotopes (a deuterium atom and the like), and the atoms constituting the substituent are also intended to include isotopes of the atoms.

In the present invention, the "substituent" at each occurrence may be further substituted with a substituent. For example, in the present invention, the "alkyl group" at each occurrence includes an alkyl group substituted with a fluorine atom (for example, a trifluoromethyl group), an alkyl group substituted with an aryl group (for example, a triphenylmethyl group), and the like, but "an alkyl group having 1 to 6 carbon atoms" represents one having 1 to 6 carbon atoms, as any group also including substituted groups thereof.

For the compound represented by the general formula (1), Cy represents a fused aromatic ring structure having the number of constituent rings of 3 or more, $Dn^1$ and $Ac^1$ have different constituent rings, and the respective constituent rings are all hydrocarbon rings. The fused aromatic ring structure having the number of constituent rings of 3 or more is not particularly limited, but for the organic load emitting element of the present invention, in the general formula (1), the Cy is preferably represented by pyrene, chrysene, fluoranthene, or phenanthrene, which may have a substituent, and more preferably pyrene which may have a substituent.

In the general formula (1), the Cy is preferably represented by pyrene which may have a substituent, and preferably has a donor group or an acceptor group at a position other than the 2- and 7-positions of the pyrene skeleton. Not wishing to be restricted to any theory, $Dn^1$ and $Ac^1$ placed at a position other than the 2- and 7-positions of the pyrene skeleton, in which HOMO and LUMO are usually present give a significant effect on the effects of the present invention. The organic load emitting element of the present invention has any one of the $Dn^1$ or the $Ac^1$ particularly on the 1- or 3-position of the pyrene skeleton, and particularly preferably has the other of the $Dn^1$ or the $Ac^1$ at the 6- or 8-position of the pyrene.

For the compound represented by the general formula (1), Cy may has a substituent other than $Dn^1$ and $Ac^1$.

Examples of the substituent other than $Dn^1$ and $Ac^1$, which Cy may have, include the following Substituent Group A.

<<Substituent Group A>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, anthranyl), amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methyl sulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxy group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazine group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidine, morpholine, pyrrolidyl, pyrrolidine, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenyl silyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the further substituent include the groups selected from the Substituent Group A as described above. Further, the substituent substituted with a substituent may be further substituted, and examples of the further substituent include the groups selected from the Substituent Group A as described above. In addition, the substituent substituted with the substituent substituted with a substituent may be further substituted, and examples of the further substituent include the groups selected from the Substituent Group A as described above.

For the material for the organic electroluminescent element of the present invention, Cy in the general formula (1) is a pyrene ring, and at least one of the 2-, 3-, 4-, 5-, 7-, 9-, and 10-positions on the pyrene ring is a substituent. By placing the substituent at these positions of the pyrene ring, it is difficult for association of the compounds represented by the general formula (1) to form in the light emitting layer, and thus, the blue color purity can be increased.

The compound used in the material for an organic electroluminescent element, represented by the general formula (1), of the present invention preferably further has an association inhibition effect from the viewpoint of improving the color purity. However, the present invention is not limited by the extent of the association inhibition effect. In the case where the compound represented by the general formula (1) is a pyrene-based compound, the pyrene-based compound has a property of causing association light emission (excimer light emission) having a longer wavelength than that of monomer light emission, and therefore, the association light emission leads to lowered color purity in some cases. In the case where the compound of the present invention represented by the general formula (1) is a pyrene-based compound, it is thought that by incorporating a substituent having an association inhibition effect into the compound, the association between the pyrene rings is effectively inhibited.

The material for an organic electroluminescent element of the present invention preferably has an alkyl group, a silyl group, an amino group, a fluorine atom, a phenyl group or pyridyl group substituted with any one of these groups, or a hydrogen atom at the 2-, 3-, 4-, 5-, 7-, 9-, and 10-positions. When only these substituents having specific structures are substituted at these positions of the pyrene ring, for example, the unsubstituted phenyl group does not easily form association, as compared with other pyrene ring compounds having substituents on these positions, whereby the change in the driving chromaticity can be decreased.

The material for an organic electroluminescent element of the present invention more preferably has any one substituent of an alkyl group, a silyl group, an amino group, a fluorine atom, and a phenyl group or pyridyl group substituted with any one of these groups at one or more of the 2-, 3-, 4-, 5-, 7-, 9-, and 10-positions.

In addition, the material for an organic electroluminescent element of the present invention particularly preferably has any one substituent of an alkyl group, a silyl group, an amino group, a fluorine atom, and a phenyl group or pyridyl group substituted with any one of these groups at one or more of the 4-, 5-, 9-, and 10-positions.

Moreover, for the material for an organic electroluminescent element of the present invention, the substituents other than $Dn^1$ and $Ac^1$ which the Cy may have are not preferably combined with each other to form a ring. However, so far as the gist of the present invention is not deviated, two adjacent substituents among the substituents other than $Dn^1$ and $Ac^1$ which the Cy may have may be combined with each other to form a 5- or 6-membered ring. The 5- or 6-membered ring thus formed may be any one of a cycloalkenyl ring, a benzene ring, and a heteroaryl ring. Examples of the heteroaryl ring include those containing 1 to 3 hetero atoms selected from the group consisting of a nitrogen atom, an oxygen atom, and a sulfur atom among the ring-constituting atoms. Specific examples thereof include a pyridine ring, a pyrazine ring, a pyridazine ring, a pyrimidine ring, an imidazole ring, an oxazole ring, a thiazole ring, a pyrazole ring, a thiophene ring, and a furan ring. The 5- or 6-membered ring thus formed may have a substituent, examples of the substituent on the carbon atom include the Substituent Group A, and examples of the substituent on the nitrogen atom include the Substituent Group B.

The compound represented by the general formula (1) is preferably a compound in which Cy is a pyrene ring and the pyrene ring is substituted with an alkyl group, a silyl group, an amino group, a fluorine atom, or an aryl group or nitrogen-containing heterocyclic group substituted with at least one of these groups, other than $Dn^1$ and $Ac^1$, at one or more positions (that is, at 3 positions in the case of containing $Dn^1$ and $Ac^1$), from the viewpoint of inhibiting the association among the pyrene-based compounds. The number of ring members of the aryl group or the nitrogen-containing heterocyclic group is not limited, but the number of ring members is preferably small to some degrees from the viewpoint of inhibiting the association inhibition, and the number of ring members is preferably 5 to 12, and more preferably 6 to 10.

Moreover, the compound represented by the general formula (1) is more preferably a compound in which Cy is a pyrene ring and the pyrene ring is substituted with an alkyl group, a silyl group, an amino group, a fluorine atom, or a phenyl group or pyridyl group substituted with any one of these groups, other than $Dn^1$ and $Ac^1$ at one or more positions in the pyrene ring, from the viewpoint of inhibiting the association among the pyrene-based compounds. The compound represented by the general formula (1) is still more preferably a compound in which any one of these substituents are substituted at 1 to 3 positions (that is, 3 to 5 positions in the case of containing $Dn^1$ and $Ac^1$), particularly preferably a compound in which any one of these substituents are substituted at 1 or 2 positions (that is, 3 or 4 positions in the case of containing $Dn^1$ and $Ac^1$), and more particularly preferably a compound in which any one of these substituents are substituted at 2 positions (that is, 4 positions in the case of containing $Dn^1$ and $Ac^1$).

Above all, the compound represented by the general formula (1) is more preferably a compound in which Cy is a pyrene ring and the pyrene ring is substituted with at least one orthoalkyl-substituted phenyl group other than $Dn^1$ and $Ac^1$ from the viewpoint of chemical stability and an association inhibition effect while not lowering the color purity. The compound represented by the general formula (1) is still more preferably a compound in which the orthoalkyl-substituted phenyl group is any one of an o-tolyl group, a 2,6-xylyl group, and a mesityl group.

In the general formula (1), $Dn^1$ represents $NR^{11}$, an O atom, or an S atom, and in the case where u1 is 0, u1 further has a substituent. Examples of the substituent include Substituent Group B as described later.

$R^{11}$ represents a substituent and $R^{11}$ may be bonded to Cy to form a ring other than an aromatic ring. Examples of the $R^{11}$ (substituent on the nitrogen atom) include the following Substituent Group B.

<<Substituent Group B>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidine, morpholine, pyrrolidyl, pyrrolidine, benzoxazolyl, benzoimidazolyl, benzothiazolyl, a carbazolyl group, an azepinyl group, and a silolyl group). These substituents may be further substituted, and examples of the further substituent include the groups selected from the Substituent Group B. Further, the substituent substituted with a substituent may be further substituted, and examples of the further substituent include the groups selected from the Substituent Group B. In addition, the substituent substituted with the substituent substituted with a substituent may be further substituted, and examples of the further substituent include the groups selected from the Substituent Group B.

The $R^{11}$ is preferably an alkyl group, a perfluoroalkyl group, an aryl group, a heteroaryl group, or a fluorine atom, and more preferably any one of a linear, branched, or cyclic alkyl group having 1 to 10 carbon atoms; an aryl group having carbon atoms 6 to 50; and a heteroaryl group having 5 to 20 carbon atoms and at least any one of N, O, and S as a hetero atom. The $R^{11}$ is particularly preferably an aryl group having 6 to 14 carbon atoms, more particularly preferably an aryl group having 6 to 14 carbon atoms, in which the aryl group is substituted with a linear or branched alkyl group having 1 to 10 carbon atoms, and still more particularly preferably an alkyl group having 6 carbon atoms, in which the alkyl group is substituted with a linear or branched alkyl group having 1 to 10 carbon atoms. As the linear or branched alkyl group having 1 to 10 carbon atoms which the aryl group having 6 to 14 carbon atoms may have is preferably, for example, methyl, ethyl, isopropyl, t-butyl, n-octyl, or n-decyl, and more preferably methyl, isopropyl, or t-butyl.

$Ac^1$ represents an electron absorbing substituent, an aryl group having an electron absorbing substituent, or an electron deficient heteroaryl group, $Ac^1$ may further have a substituent. Here, in the present specification, the electron absorbing substituent refers to a "substituent having a substituent constant $\sigma_p$ of more than 0.05 in the Hammett's law".

The electron deficient heteroaryl group refers to one having a n electron density of carbon atoms in the heteroaryl group of 1.00 or less, as described in pp. 3 to 4 of "Chemistry of Heterocyclic Compounds" (Kodansha Scientific Ltd.).

Examples of the electron absorbing substituent as the $Ac^1$ include a halogen atom (for example, a fluorine atom), a cyano group, and a trifluoromethyl group, and above all, the cyano group is preferred.

As the aryl group having an electron absorbing substituent as the $Ac^1$, an aryl group having 6 to 10 carbon atoms, substituted with an electron absorbing substituent, is preferred, and an aryl group having 6 carbon atoms, substituted with an electron absorbing substituent, is more preferred. The electron absorbing substituent of the aryl group having an electron absorbing substituent is the same as the electron absorbing substituent as the $Ac^1$, and the preferred range thereof is also the same.

The electron deficient heteroaryl group as the $Ac^1$, an N atom-containing heteroaryl group having a number of ring members of 6 to 14 is preferred, an N atom-containing heteroaryl group having a number of ring members of 6 to 14 is more preferred, and an N atom-containing heteroaryl group having a number of ring members of 6 is particularly preferred.

Further, the electron deficient heteroaryl group may be substituted with an alkyl group (which may be further substituted with a fluorine atom) or a silyl group (which may be further substituted with an alkyl group, and the preferred range thereof is as described above). By containing an alkyl group or a silyl group, the chemical stability of the compound is improved and the change in the driving chromaticity does not easily occur while not lowering the color purity. Here, the alkyl group is the same as the alkyl group which may be contained when $R^{11}$ is an aryl group, and the preferred range thereof is also the same.

The $Ac^1$ is preferably an aryl group having an electron absorbing substituent or an electron deficient heteroaryl group.

The ring $Z^1$ represents an arylene group or a heteroarylene group, $A^{11}$ represents a carbon atom constituting the ring $Z^1$, $A^{12}$ represents a carbon atom or a nitrogen atom constituting the ring $Z^1$.

$L^1$, $L^2$ and $L^3$ each independently represent an oxygen atom, a sulfur atom, $CR^{12}R^{13}$, or $SiR^{14}R^{15}$, and $R^{12}$, $R^{13}$, $R^{14}$ and $R^{15}$ each independently represent a hydrogen atom or a substituent.

In $CR^{12}R^{13}$, the carbon atom becomes a ring-constituting atom of the compound represented by the general formula (1), and $R^{12}$ and $R^{13}$ represent a hydrogen atom or a substituent, which is bonded to the carbon atom. $R^{12}$ and $R^{13}$ may be the same as or different from each other. Further, $R^{12}$ and $R^{13}$ may be combined with each other to form a 5- or 6-membered ring.

In $SiR^{14}R^{15}$, the silicon atom becomes a ring-constituting atom of the compound represented by the general formula (1), and $R^{14}$ and $R^{15}$ represent a hydrogen atom or a substituent, which is bonded to the carbon atom. $R^{14}$ and $R^{15}$ may be the same as or different from each other. Further, $R^{14}$ and $R^{15}$ may be combined with each other to form a 5- or 6-membered ring.

Examples of $R^{12}$, $R^{13}$, $R^{14}$ and $R^{15}$ (the substituent on the carbon atom and the substituent on the silicon atom) include the Substituent Group A.

$R^{12}$, $R^{13}$, $R^{14}$ and $R^{15}$ are preferably each independently an alkyl group, an aryl group, a heteroaryl group, a perfluoroalkyl group, an alkoxy group, or a fluorine atom, and more preferably an alkyl group, an aryl group, or a heteroaryl group. $R^{12}$, $R^{13}$, $R^{14}$ and $R^{15}$ are particularly preferably each independently any one of a linear, branched, or cyclic alkyl group having 1 to 10 carbon atoms; an aryl group having 6 to 14 carbon atoms; and a heteroaryl group having 5 to 20 carbon atoms, which contains at least any one of N, 0, and S as a hetero atom; and more particularly preferably a linear or branched alkyl group having 1 to 6 carbon atoms. Further, from the viewpoint of easiness of synthesis, $R^{12}$ and $R^{13}$ are preferably the same substituents. In addition, from the same viewpoint, $R^{14}$ and $R^{15}$ are preferably the same substituents.

$R^{12}$, $R^{13}$, $R^{14}$ and $R^{15}$ may be combined with each other to form a 5- or 6-membered ring. The 5- or 6-membered ring thus formed may be any one of a cycloalkyl ring, a cycloalkenyl ring, and a heterocycle. Examples of the heterocycle include those containing 1 to 3 hetero atoms selected from the group consisting of a nitrogen atom, an oxygen atom, and a sulfur atom among the ring-constituting atoms. The 5- or 6-membered ring thus formed may have a substituent, examples of the substituent on the carbon atom include Substituent Group A as described above, and examples of the substituent on the nitrogen atom include the Substituent Group B as described above.

In the present invention, in the general formula (1), $L^1$, $L^2$ and $L^3$ are preferably each independently any one of $CR^{12}R^{13}$ and O, and more preferably $CR^{12}R^{13}$, from the viewpoint of the light emitting color.

In the general formula (1), u1 represents 0 or 1, and in the case where u1 is 1, the rings formed by Cy, $Dn^1$, and the ring $Z^1$ is not an aromatic ring, u1 is preferably 1.

In the general formula (1), m1 represents 0 or 1, and when m1 is 0 and u1 is 1, Cy and the ring $Z^1$ are directly bonded to each other. When the $Dn^1$ is $NR^{11}$, m1 is preferably 0, when the $Dn^1$ is an O atom or an S atom, m1 is preferably 1. Above all, a combination in which the $Dn^1$ is $NR^{11}$ and the m1 is 0 is more preferred.

In the general formula (1), n1 and q1 represent 0 or 1, and in the case where any one of n1 and q1 is 0 and n1 or q1 is 1, Cy, the rings formed by $Ac^1$ and $L^2$ or $L^3$ are not all aromatic rings. However, when $Ac^1$ is a pyridine ring, at least one of n1 and q1 is 1.

In the organic electroluminescent element of the present invention, the compound represented by the general formula (1) is preferably a compound represented by any one of the following general formulae (2) to (5). Hereinafter, each general formula of the general formulae (2) to (5) will be described.

[Chem. 16]

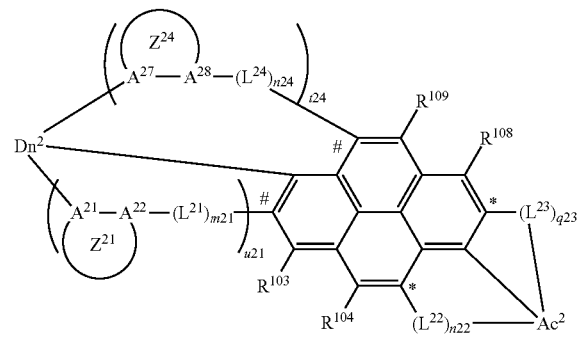

General formula (2)

(in which in the case where $Dn^2$ represents an N atom, an O atom, or an S atom and $Dn^2$ represents an O atom or an S atom, the sum of u21 and t24 is 0 or 1. When in the case where $Dn^2$ represents an N atom, at least one of u21 and t24 represents 0, or when in the case where $Dn^2$ represents an O atom or an S atom, u21 and t24 are both 0, $Dn^2$ further has a substituent. $Ac^2$ represents an electron absorbing substituent, an aryl group having an electron absorbing substituent, or an electron deficient heteroaryl group, and $Ac^2$ may further have a substituent. The ring $Z^{21}$ and the ring $Z^{24}$ each independently represent an arylene group or a heteroarylene group, $A^{21}$ represents a carbon atom constituting the ring $Z^{21}$, $A^{22}$ represents a carbon atom or a nitrogen atom constituting the ring $Z^{21}$, $A^{27}$ represents a carbon atom constituting the ring $Z^{24}$, and $A^{28}$ represents a carbon atom or a nitrogen atom constituting the ring $Z^{24}$. $R^{103}$, $R^{104}$, $R^{108}$ and $R^{109}$ each independently represent a hydrogen atom or a substituent. $L^{21}$, $L^{22}$, $L^{23}$ and $L^{24}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #position of the pyrene ring and $Dn^2$ are not bonded to each other, and in the case where u21 is 1, the ring formed by the pyrene ring, $Dn^2$, and the ring $Z^{21}$ is not an aromatic ring. t24 represents 0 or 1, in the case where t24 is 0, the #position of the pyrene ring and $Dn^2$ are not bonded to each other, and in the case where t24 is 1, the ring formed by the pyrene ring, $Dn^2$, and the ring $Z^{24}$ is not an aromatic ring. m21 represents 0 or 1, and when m21 is 0 and u21 is 1, the #position of the pyrene ring and the ring $Z^{21}$ are directly bonded to each other. s24 represents 0 or 1, and when s24 is 0 and u24 is 1, the #position of the pyrene ring and the ring $Z^{24}$ are directly bonded to each other. n22 and q23 represent 0 or 1, in the case where any one of n22 and q23 is 0 and n22 or q23 is 1, the rings formed by the pyrene ring, $Ac^2$ and $L^{22}$ or $L^{23}$ are not all aromatic rings. In the case where n22 or q23 is 0, the * position of the pyrene ring and $Ac^2$ are not bonded to each other. However, when $Ac^2$ is a pyridine ring, at least one of n22 and q23 is 1.)

[Chem. 17]

General formula (3)

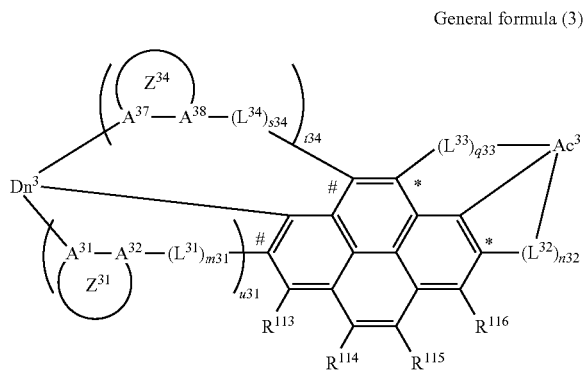

(in which $Dn^3$ represents an N atom, an O atom, or an S atom, and in the case where $Dn^3$ represents an O atom or an S atom, the sum of u31 and t34 is 0 or 1. When in the case where $Dn^3$ represents an N atom, at least one of u31 and t34 represents 0, or when in the case where $Dn^3$ represents an O atom or an S atom and u31 and t34 are both 0, $Dn^3$ further has a substituent. $Ac^3$ represents an electron absorbing substituent, an aryl group having an electron absorbing substituent, or an electron deficient heteroaryl group, and $Ac^3$ may further have a substituent. The ring $Z^{31}$ and the ring $Z^{34}$ each independently represent an arylene group or a heteroarylene group, $A^{31}$ represents a carbon atom constituting the ring $Z^{31}$, and $A^{32}$ represents a carbon atom or a nitrogen atom constituting the ring $Z^{31}$, $A^{37}$ represents a carbon atom constituting the ring $Z^{34}$, and $A^{38}$ represents a carbon atom or a nitrogen atom constituting the ring $Z^{34}$. $R^{113}$, $R^{114}$, $R^{115}$ and $R^{116}$ each independently represent a hydrogen atom or a substituent. $L^{31}$, $L^{32}$, $L^{33}$ and $L^{34}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, in the case where u31 is 0, the #position of the pyrene ring and $Dn^3$ are not bonded to each other, and in the case where u31 is 1, the ring formed by the pyrene ring, $Dn^3$ and the ring $Z^{31}$ is not an aromatic ring. t34 represents 0 or 1, in the case where t34 is 0, the #position of the pyrene ring and $Dn^3$ are not bonded to each other, and in the case where t34 is 1, the ring formed by pyrene ring, $Dn^3$ and the ring $Z^{34}$ is not an aromatic ring. m31 represents 0 or 1, and when m31 is 0 and u31 is 1, the #position of the pyrene ring and the ring $Z^{31}$ are directly bonded to each other. m34 represents 0 or 1 and when m34 is 0 and t34 is 1, the #position of the pyrene ring and the ring $Z^{34}$ are directly bonded to each other. n32 and q33 represent 0 or 1, and in the case where any one of n32 and q33 is 0 and n32 or q33 is 1, the rings formed by the pyrene ring, $Ac^3$ and $L^{32}$ or $L^{33}$ are not all aromatic rings. In the case where n32 or q33 is 0, the * position of the pyrene ring and $Ac^3$ are not bonded to each other. However, when $Ac^3$ is a pyridine ring, at least one of n32 and q33 is 1.)

[Chem. 18]

General formula (4)

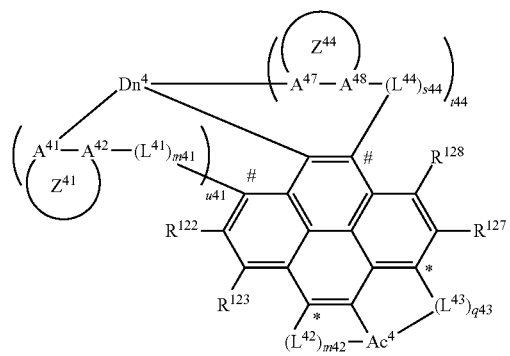

(in which $Dn^4$ represents an N atom, an O atom, or an S atom, and in the case where $Dn^4$ represents an O atom or an S atom, the sum of u41 and t44 is 0 or 1. When in the case where $Dn^4$ represents an N atom and at least one of u41 and t44 represents 0, or when in the case where $Dn^4$ represents an O atom or an S atom, u41 and t44 are both 0, $Dn^4$ further has a substituent. $Ac^4$ represents an electron absorbing substituent, an aryl group having an electron absorbing substituent, or an electron deficient heteroaryl group, and $Ac^4$ may further have a substituent. The ring $Z^{41}$ and the ring $Z^{44}$ each independently represent an arylene group or a heteroarylene group, $A^{41}$ represents a carbon atom constituting the ring $Z^{41}$, $A^{42}$ represents a carbon atom or a nitrogen atom constituting the ring $Z^{41}$, $A^{47}$ represents a carbon atom constituting the ring $Z^{44}$, and $A^{48}$ represents a carbon atom or a nitrogen atom constituting the ring $Z^{44}$. $R^2$, $R^3$, $R^7$ and $R^8$ each independently represent a hydrogen atom or a substituent. $L^{41}$, $L^{42}$, $L^{43}$ and $L^{44}$ each independently represent an oxygen atom, a sulfur atom, $CR^{42}R^{43}$, or $SiR^{44}R^{45}$, and $R^{42}$, $R^{43}$, $R^{44}$ and $R^{45}$ each independently represent a hydrogen atom or a substituent. u41 represents 0 or 1, in the case where u41 is 0, the #position of the pyrene ring and $Dn^4$ are not bonded to each other, and in the case where u41 is 1, the ring formed by the pyrene ring, $Dn^4$ and the ring $Z^{41}$ is not an aromatic ring. t44 represents 0 or 1, in the case where t44 is 0, the #position of the pyrene ring and $Dn^4$ are not bonded to each other, and in the case where t44 is 1, the ring formed by the pyrene ring, $Dn^4$ and the ring $Z^{44}$ is not an aromatic ring. m41 represents 0 or 1, and when m41 is 0 and u41 is 1, the #position of the pyrene ring and the ring $Z^{41}$ are directly bonded to each other. m44 represents 0 or 1, and when m44 is 0 and t44 is 1, the #position of the pyrene ring and the ring $Z^{44}$ are directly bonded to each other. n42 and q43 represents 0 or 1, and in the case where any one of n42 and q43 is 0 and n42 or q43 is 1, the rings formed by the pyrene ring, Ac and L or L are not all aromatic rings. In the case where n42 or q43 is 0, the * position of the pyrene ring and $Ac^4$ are not bonded to each other. However, when $Ac^4$ is a pyridine ring, at least one of n42 and q43 is 1.)

[Chem. 19]

General formula (5)

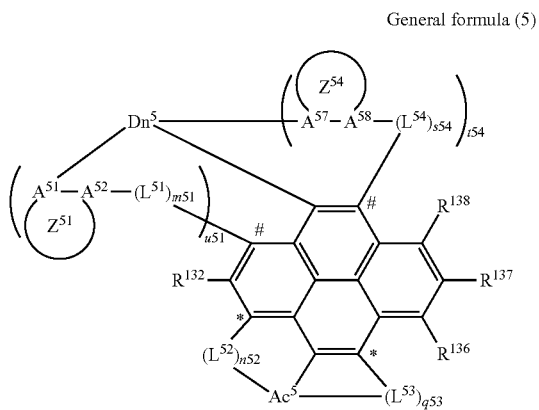

(in which $Dn^5$ represents an N atom, an O atom, or an S atom, in the case where $Dn^5$ represents an O atom or an S atom, the sum of u51 and t54 is 0 or 1. When in the case where $Dn^5$ represents an N atom, at least one of u51 and t54 represents 0, or when in the case where $Dn^5$ represents an O atom or an S atom, u51 and t54 are both 0, $Dn^5$ further has a substituent. $Ac^5$ represents an electron absorbing substituent, an aryl group having an electron absorbing substituent, or an electron deficient heteroaryl group, $Ac^5$ may further have a substituent. The ring $Z^{51}$ and the ring $Z^{54}$ each independently represent an arylene group or a heteroarylene group, $A^{51}$ represents a carbon atom constituting the ring $Z^{51}$, $A^{52}$ represents a carbon atom or a nitrogen atom constituting the ring $Z^{51}$, $A^{57}$ represents a carbon atom constituting the ring $Z^{54}$, and $A^{58}$ represents a carbon atom or a nitrogen atom constituting the ring $Z^{54}$. $R^2$, $R^6$, $R^7$ and $R^8$ each independently represent a hydrogen atom or a substituent. $L^{51}$, $L^{52}$, $L^{53}$ and $L^{54}$ each independently represent an oxygen atom, a sulfur atom, $CR^{52}R^{53}$, or $SiR^{54}R^{55}$, and $R^{52}$, $R^{53}$, $R^{54}$ and $R^{55}$ each independently represent a hydrogen atom or a substituent. u51 represents 0 or 1, in the case where u51 is 0, the #position of the pyrene ring and $Dn^5$ are not bonded to each other, and in the case where u51 is 1, the ring formed by the pyrene ring, $Dn^5$ and the ring $Z^{51}$ is not an aromatic ring. t54 represents 0 or 1, in the case where t54 is 0, the #position of the pyrene ring and $Dn^5$ are not bonded to each other, and in the case where t54 is 1, the ring formed by the pyrene ring, $Dn^5$ and the ring $Z^{54}$ is not an aromatic ring. m51 represents 0 or 1, and when m51 is 0 and u51 is 1, the #position of the pyrene ring and the ring $Z^{51}$ are directly bonded to each other. m54 represents 0 or 1, and when m54 is 0 and t54 is 1, the #position of the pyrene ring and the ring $Z^{54}$ are directly bonded to each other. n52 and q53 represents 0 or 1, and in the case where any one of n52 and q53 is 0 and n52 or q53 is 1, the rings formed by the pyrene ring, $Ac^5$ and $L^{52}$ or $L^{53}$ are not all aromatic rings. In the case where n52 or q53 is 0, the * position of the pyrene ring and $Ac^5$ are not bonded to each other. However, when $Ac^5$ is a pyridine ring, at least one of n52 and q53 is 1.)

The description and the preferred ranges of $Dn^2$ and $Ac^2$ in the general formula (2) are the same as the description and the preferred ranges of $Dn^1$ and $Ac^1$ in the general formula (1). The description and the preferred ranges of the ring $Z^{21}$, the ring $Z^{24}$, $A^{21}$, $A^{22}$, $A^{27}$, and $A^{28}$ in the general formula (2) are the same as the description and the preferred ranges of the ring $Z^1$, $A^{11}$, and $A^{12}$ in the general formula (1). The description and the preferred ranges of $L^{21}$ and $L^{24}$ in the general formula (2) are the same as the description and the preferred ranges of $L^1$ in the general formula (1). The description and the preferred ranges of u21 and t24 in the general formula (2) are the same as the description and the preferred ranges of u1 in the general formula (1). The description and the preferred ranges of m21 and s24 in the general formula (2) are the same as the description and the preferred ranges of m1 in the general formula (1). The description and the preferred ranges of $L^{22}$, $L^{23}$, n22, and q23 in the general formula (2) are the same as the description and the preferred ranges of $L^2$, $L^3$, n1, and q1 in the general formula (1). In the case where $R^{103}$, $R^{104}$, $R^{108}$ and $R^{109}$ in the general formula (2) each represent a substituent, the range of the substituent is the same as the range of a substituent other than $Dn^1$ and $Ac^1$, which Cy may have in the general formula (1), and above all, it is preferable that $R^{103}$, $R^{104}$, $R^{108}$ and $R^{109}$ do not contain pyrene skeletons.

The description and the preferred ranges of $Dn^3$ and $Ac^3$ in the general formula (3) are the same as the description and the preferred ranges of $Dn^1$ and $Ac^1$ in the general formula (1). The description and the preferred ranges of the ring $Z^{31}$, the ring $Z^{34}$, $A^{31}$, $A^{32}$, $A^{37}$, and $A^{38}$ in the general formula (3) are the same as the description and the preferred ranges of the ring $Z^1$, $A^{11}$, and $A^{12}$ in the general formula (1). The description and the preferred ranges of $L^{31}$ and $L^{34}$ in the general formula (3) are the same as the description and the preferred ranges of $L^1$ in the general formula (1). The description and the preferred ranges of u31 and t34 in the general formula (3) are the same as the description and the preferred ranges of u1 in the general formula (1). The description and the preferred ranges of m31 and s34 in the general formula (3) are the same as the description and the preferred ranges of m1 in the general formula (1). The description and the preferred ranges of $L^{32}$, $L^{33}$, n32, and q33 in the general formula (3) are the same as the description and the preferred ranges of $L^2$, $L^3$, n1, and q1 in the general formula (1). In the case where $R^{113}$, $R^{114}$, $R^{115}$ and $R^{116}$ in the general formula (3) each represent a substituent, the range of the substituent is the same as the range of a substituent other than $Dn^1$ and $Ac^1$, which Cy may have in the general formula (1), and above all, it is preferable that $R^{113}$, $R^{114}$, $R^{115}$ and $R^{116}$ do not contain pyrene skeletons.

The description and the preferred ranges of $Dn^4$ and $Ac^4$ in the general formula (4) are the same as the description and the preferred ranges of $Dn^1$ and $Ac^1$ in the general formula (1). The description and the preferred ranges of the ring $Z^{41}$, the ring $Z^{44}$, $A^{41}$, $A^{42}$, $A^{47}$, and $A^{48}$ in the general formula (4) are the same as the description and the preferred ranges of the ring $Z^1$, $A^{11}$, and $A^{12}$ in the general formula (1). The description and the preferred ranges of $L^{41}$ and $L^{44}$ in the general formula (4) are the same as the description and the preferred ranges of $L^1$ in the general formula (1). The description and the preferred ranges of u41 and t44 in the general formula (4) are the same as the description and the preferred ranges of u1 in the general formula (1). The description and the preferred ranges of m41 and s44 in the general formula (4) are the same as the description and the preferred ranges of m1 in the general formula (1). The description and the preferred ranges of $L^{42}$, $L^{43}$, n42, and q43 in the general formula (4) are the same as the description and the preferred ranges of $L^2$, $L^3$, n1, and q1 in the general formula (1). In the case where $R^{122}$, $R^{123}$, $R^{127}$ and $R^{128}$ in the general formula (4) each represent a substituent, the range of the substituent is the same as the range of a substituent other than $Dn^1$ and $Ac^1$, which Cy may have in the general formula (1), and above all, it is preferable that $R^{122}$, $R^{123}$, $R^{127}$ and $R^{128}$ do not contain pyrene skeletons.

The description and the preferred ranges of $Dn^5$ and $Ac^5$ in the general formula (5) are the same as the description and the preferred ranges of $Dn^1$ and $Ac^1$ in the general formula (1). The description and the preferred ranges of the ring $Z^{51}$, the ring $Z^{54}$, $A^{51}$, $A^{52}$, $A^{57}$, and $A^{58}$ in the general formula (5) are the same as the description and the preferred ranges of the ring $Z^1$, $A^{11}$, and $A^{12}$ in the general formula (1). The description and the preferred ranges of $L^{51}$ and $L^{54}$ in the general formula (5) are the same as the description and the preferred ranges of $L^1$ in the general formula (1). The description and the preferred ranges of u51 and t54 in the general formula (5) are the same as the description and the preferred ranges of u1 in the general formula (1). The description and the preferred ranges of m51 and s54 in the general formula (5) are the same as the description and the preferred ranges of m1 in the general formula (1). The description and the preferred ranges of $L^{52}$, $L^{53}$, n52, and q53 in the general formula (5) are the same as the description and the preferred ranges of $L^2$, $L^3$, n1, and q1 in the general formula (1). In the case where $R^{132}$, $R^{136}$, $R^{137}$ and $R^{138}$ in the general formula (5) each represent a substituent, the range of the substituent is the same as the range of a substituent other than $Dn^1$ and $Ac^1$, which Cy may have in the general formula (1), and above all, it is preferable that $R^{132}$, $R^{136}$, $R^{137}$ and $R^{138}$ do not contain pyrene skeletons.

In the organic electroluminescent element of the present invention, the compound represented by the general formula (1) is preferably a compound represented by the general formula (2) or (3) out of the general formulae (2) to (5). Hereinafter, the more preferred structures of the compounds represented by the general formula (2) and (3) will be described.

(Compound Represented by General Formula (2))

In the organic electroluminescent element of the present invention, the q23 is preferably 1 in the general formula (2). Further, in this case, n22 is 0.

The compound represented by the general formula (2) is preferably a compound represented by the following general formula (6)

[Chem. 20]

General formula (6)

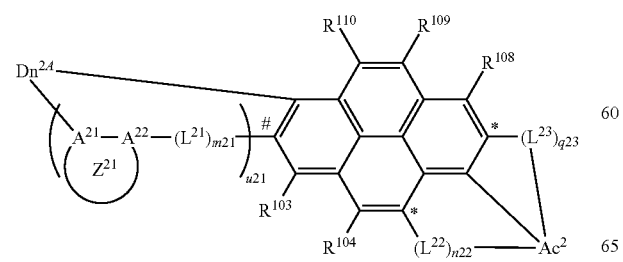

(in which $Dn^{24}$ represents $NR^{114}$, an O atom, or an S atom, and when u21 represents 0, $Dn^{24}$ further has a substituent. $R^{114}$ represents a substituent. $Ac^2$ represents an electron absorbing substituent, an aryl group having an electron absorbing substituent, or an electron deficient heteroaryl group, $Ac^2$ may further have a substituent. The ring $Z^{21}$ represents an arylene group or a heteroarylene group, $A^{21}$ represents a carbon atom constituting the ring $Z^{21}$, $A^{22}$ represents a carbon atom or a nitrogen atom constituting the ring $Z^{21}$. $R^{103}$, $R^{104}$, $R^{108}$, $R^{109}$ and $R^{110}$ each independently represent a hydrogen atom or a substituent. $L^{21}$, $L^{22}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #position of the pyrene ring and $Dn^{24}$ are not bonded to each other, and in the case where u21 is 1, the rings formed by the pyrene ring, $Dn^{24}$ and the ring $Z^{21}$ is not an aromatic ring, m21 represents 0 or 1, and when m21 is 0 and u21 is 1, the #position of the pyrene ring and the ring $Z^{21}$ are directly bonded to each other. n22 and q23 represent 0 or 1, and in the case where any one of n22 and q23 is 0 and n22 or q23 is 1, the rings formed by the pyrene ring, $Ac^2$ and $L^{22}$ or $L^{23}$ are not all aromatic rings. In the case where n22 or q23 is 0, the * position of the pyrene ring and $Ac^2$ are not bonded to each other. However, when $Ac^2$ is a pyridine ring, at least one of n22 and q23 is 1.)

In the general formula (6), the range represented by a group having the same name as the general formula (2) is the same as the preferred range in the general formula (2) of the group.

The description and the preferred ranges of $Dn^{24}$ in the general formula (6) are the same as the description and the preferred ranges of $Dn^1$ in the general formula (1). The substituents which $Dn^{24}$ in the general formula (6) may further have are the rings formed by $A^{22}$, $A^{23}$, $A^{24}$, $A^{25}$ and $A^{26}$ in the general formula (10) as described later, and these will be described later.

The range of the substituent in the case where $R^{110}$ in the general formula (6) represents a substituent is the same as the range of the substituents other than $Dn^1$ and $Ac^1$, which Cy in the general formula (1) may have, and it is preferable that the substituent do not contain a pyrene skeleton.

In the organic electroluminescent element of the present invention, the compound represented by the general formula (6) is preferably a compound represented by the following general formula (8).

[Chem. 21]

General formula (8)

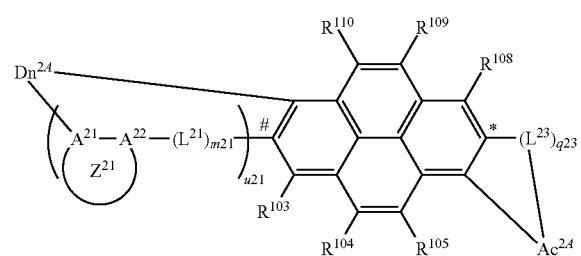

(in which $Dn^{24}$ represents $NR^{114}$, an O atom, or an S atom, and when u21 represents 0, $Dn^{24}$ further has a substituent. $R^{114}$ represents a substituent. $Ac^{24}$ represents an electron absorbing substituent, an aryl group having an electron absorbing substituent, or an electron deficient heteroaryl group, $Ac^{24}$ may further have a substituent. The ring $Z^{21}$ represents an arylene group or a heteroarylene group, $A^{21}$ represents a carbon atom constituting the ring $Z^{21}$, and $A^{22}$ represents a carbon atom or a nitrogen atom constituting the ring $Z^{21}$. $R^{103}$, $R^{104}$, $R^{105}$, $R^{108}$, $R^{109}$ and $R^{110}$ each independently represent a hydrogen atom or a substituent. $L^{21}$ and L each independently represent an oxygen atom, a sulfur atom, $CR^{32}R^{33}$, or $SiR^{24}R^{25}$, and $R^{22}$, $R^{23}$, $R^{24}$ and $R^{25}$ each independently represent a hydrogen atom or a substituent. u21 represents 0 or 1, in the case where u21 is 0, the #position of the pyrene ring and $Dn^{24}$ are not bonded to each other, and in the case where u21 is 1, the ring formed by the pyrene ring, $Dn^{24}$ and the ring $Z^{21}$ is not an aromatic ring. m21 represents 0 or 1, when m21 is 0 and u21 is 1, the #position of the pyrene ring and the ring $Z^{21}$ are directly bonded to each other. q23 represents 0 or 1, and in the case where q23 is 1, the rings formed by the pyrene ring, $Ac^{24}$ and $L^{23}$ are not all aromatic rings. In the case where q23 is 0, the * position of the pyrene ring and $Ac^{24}$ are not bonded to each other. However, when $Ac^{24}$ is a pyridine ring, q23 is 1.)

In the general formula (8), the range represented by a group having the same name as the general formula (6) is the same as the preferred range in the general formula (6) of the group.

The description and the preferred ranges of $Ac^{24}$ in the general formula (8) are the same as the description and the preferred ranges of $Ac^2$ in the general formula (6). The substituents which $Ac^2$ in the general formula (8) may further have are the rings formed by $A^{61}$, $A^{62}$, $A^{63}$, $A^{64}$, and $A^{65}$ in the general formulae (10) and (12) as described later, and these will be described later.

The range of the substituent in the case where $R^{105}$ in the general formula (8) represents a substituent is the same as the range of the substituents other than $Dn^1$ and $Ac^1$, which Cy in the general formula (1) may have, and it is preferable that the substituent do not contain a pyrene skeleton.

In the organic electroluminescent element of the present invention, the compound represented by the general formula (8) is preferably a compound represented by the following general formula (10).

[Chem. 22]

General formula (10)

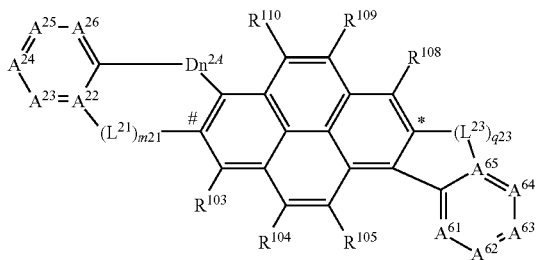

(in which $Dn^{24}$ represents $NR^{114}$, an O atom, or an S atom, and $R^{114}$ represents a substituent. $A^{22}$, $A^{23}$, $A^{24}$, $A^{25}$, $A^{26}$, $A^{61}$, $A^{62}$, $A^{63}$, $A^{64}$ and $A^{65}$ each independently represent CRzs (Rz represents a hydrogen atom or a substituent, and two adjacent CRzs may be combined with each other to form a 5- or 6-membered ring) or an N atom. In the case where $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent. $R^{103}$, $R^{104}$, $R^{105}$, $R^{108}$, $R^{109}$ and $R^{110}$ each independently represent a hydrogen atom or a substituent. $L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. m21 represents 0 or 1, and when m21 is 0, the #position of the pyrene ring and $A^{22}$ are directly bonded to each other. q23 represents 0 or 1, and in the case where q23 is 0, the * position of the pyrene ring and $A^{65}$ are not bonded to each other. However, in the case where only one of $A^{61}$, $A^{62}$, $A^{63}$, $A^{64}$ and $A^{65}$ is an N atom, q23 represents 1.)

In the general formula (10), the range represented by a group having the same name as the general formula (8) is the same as the preferred range in the general formula (8) of the group.

$A^{22}$, $A^{23}$, $A^{24}$, $A^{25}$ and $A^{26}$ in the general formula (10) each independently represent CRzs (Rz represents a hydrogen atom or a substituent, and two adjacent CRzs may be combined with each other to form a 5- or 6-membered ring) or an N atom.

The number of the nitrogen atoms contained in $A^{22}$, $A^{23}$, $A^{24}$, $A^{25}$ and $A^{26}$ in the general formula (10) is preferably 1 or less, and more preferably 0. In this case, the positions of the nitrogen atoms in $A^{22}$, $A^{23}$, $A^{24}$, $A^{25}$, and $A^{26}$ are not particularly limited.

When two or more of $A^{22}$, $A^{23}$, $A^{24}$, $A^{25}$, and $A^{26}$ represent CRz, it is preferable that the respective substituents (the corresponding Rz) which two adjacent groups thereof contain carbon atoms be not combined with each other to form a 5- or 6-membered ring in the present invention, but they may be combined with each other to form a 5- or 6-membered ring. The 5- or 6-membered ring thus formed may be any one of a cycloalkenyl ring, a benzene ring, and a heteroaryl ring. Examples of the heteroaryl ring include those in which 1 to 3 hetero atoms selected from the group consisting of a nitrogen atom, an oxygen atom, and a sulfur atom among the atoms constituting the ring. Specific examples thereof include a pyridine ring, a pyrazine ring, a pyridazine ring, a pyrimidine ring, an imidazole ring, an oxazole ring, a thiazole ring, a pyrazole ring, a thiophene ring, and a furan ring. The 5- or 6-membered ring thus formed may have a substituent, examples of the substituent on the carbon atom include the Substituent Group A, and examples of the substituent on the nitrogen atom include the Substituent Group B. The 5- or 6-membered ring thus formed is preferably a benzene ring, and more preferably an unsubstituted benzene ring.

When $A^{22}$, $A^{23}$, $A^{24}$, $A^{25}$, and $A^{26}$ represent CRz, Rz represents a hydrogen atom or a substituent.

When $A^{22}$, $A^{23}$, $A^{24}$, $A^{25}$, and $A^{26}$ represent CRz, examples of Rz include the Substituent Group A. When $A^{22}$, $A^{23}$, $A^{24}$, $A^{25}$, and $A^{26}$ represent CRz, Rz is preferably a substituent having any one of a fluorine atom, an alkyl group, a silyl group, an aryl group, an aryloxy group, a cyano group, and an amino group. Specific examples thereof include a fluorine atom, an alkyl group, a perfluoroalkyl group, a trialkylsilyl group, a phenyl group, a phenoxy group, and a diarylamino group.

When $A^{22}$, $A^{23}$, $A^{24}$, $A^{25}$, and $A^{26}$ represent CRz, Rz preferably represents a hydrogen atom, an alkyl group, a silyl group, an aryl group, or an aryloxy group, more preferably a hydrogen atom, an alkyl group, or a silyl group, and particularly preferably a hydrogen atom or an alkyl group.

When $A^{22}$, $A^{23}$, $A^{24}$, $A^{25}$, and $A^{26}$ represent CRz, the alkyl group represented by Rz is preferably an unsubstituted linear alkyl group, an unsubstituted branched alkyl group, an unsubstituted cycloalkyl group, or a perfluoroalkyl group, more preferably a linear alkyl group having 1 to 6 carbon atoms, a branched alkyl group having 1 to 6 carbon atoms, and a perfluoroalkyl group having 1 to 6 carbon atoms, particularly preferably a methyl group, an ethyl group, an isopropyl group, a t-butyl group, a t-amyl group, a neopentyl group, or a trifluoromethyl group, and more particularly preferably a methyl group, an ethyl group, an isopropyl group, or a t-butyl group.

When $A^{22}$, $A^{23}$, $A^{24}$, $A^{25}$, and $A^{26}$ represent CRz, the silyl group represented by Rz is preferably an alkylsilyl group, and more preferably a trialkylsilyl group. The alkyl groups of the trialkylsilyl group are preferably each independently a methyl group, an ethyl group, or an isopropyl group, and more preferably a methyl group. When $A^{22}$, $A^{23}$, $A^{24}$, $A^{25}$, and $A^{26}$ represent CRz, the silyl group represented by at least one of Rzs is particularly preferably a trimethylsilyl group.

$A^{61}$, $A^{62}$, $A^{63}$, $A^{64}$ and $A^{65}$ in the general formula (10) each independently represent CRzs (Rz represents a hydrogen atom or a substituent, and two adjacent CRzs may be combined with each other to form a 5- or 6-membered ring) or an N atom. In the case where $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent.

At least one of $A^{61}$, $A^{62}$, $A^{63}$, $A^{64}$ and $A^{65}$ in the general formula (10) is preferably a nitrogen atom, and in this case, the preferred positions of nitrogen atoms in $A^{61}$, $A^{62}$, $A^{63}$, $A^{64}$ and $A^{65}$ are not particularly limited.

In $A^{22}$, $A^{23}$, $A^{24}$, $A^{25}$, and $A^{26}$, the number of the nitrogen atoms is preferably 1 to 3 from the viewpoint of chemical stability of the compound, and more preferably 2 or 3 from the viewpoint of increasing the blue color purity.

In the nitrogen-containing aromatic heterocycle, a carbon atom in the vicinity of an N atom constituting the heterocycle is a reaction active position, and when the carbon atom in the vicinity of an N atom has a substituent, the chemical stability in the redox state and excitation state is improved, which is thus preferable. It is more preferable that both the carbon atoms in the vicinity of an N atom have a substituent. In particular, by introducing an alkyl group (including a fluoroalkyl group) or a silyl group into both the carbon atoms in the vicinity of an N atom, the chemical stability in the redox state and excitation state is improved while not lowering the color purity and the change in the driving chromaticity can be reduced, with the alkyl group providing higher stability. From the viewpoint of this, in the general formula (10), a case where at least one of $A^{61}$, $A^{63}$ and $A^{65}$ is a nitrogen atom, and $A^{62}$ and $A^{64}$ are each independently CRz is preferred. In this case, at least one of the substituent Rz which $A^{62}$ and $A^{64}$ have (preferably one adjacent to an N atom in $A^{62}$ and $A^{64}$) is preferably an alkyl group or a silyl group, and more preferably an alkyl group. Further, in the general formula (10), in the case where $A^{61}$, $A^{63}$ and $A^{65}$ are CRz, a preferred range of Rz is the same as the preferred range of the substituent Rz which $A^{62}$ and $A^{64}$ have.

In the organic electroluminescent element of the present invention, the compound represented by the general formula (10) is preferably a compound represented by the following general formula (12).

[Chem. 23]

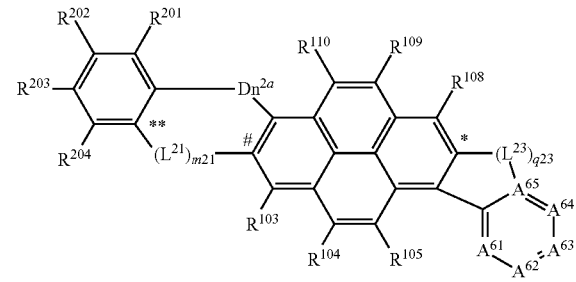

General formula (12)

(in which $Dn^{2A}$ represents $NR^{11A}$, an O atom, or an S atom, and $R^{11A}$ represents a substituent. $A^{61}$, $A^{62}$, $A^{63}$, $A^{64}$ and $A^{65}$ each independently represent CRzs (Rz represents a hydrogen atom or a substituent, and two adjacent CRzs may be combined with each other to form a 5- or 6-membered ring) or an N atom. In the case where $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent. $R^{103}$, $R^{104}$, $R^{105}$, $R^{108}$, $R^{109}$, $R^{110}$, $R^{201}$, $R^{202}$, $R^{203}$ and $R^{204}$ each independently represent a hydrogen atom or a substituent. $L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent. m21 represents 0 or 1, and when m21 is 0, the ** position and the #position of the pyrene ring are directly bonded to each other. q23 represents 0 or 1, and in the case where q23 is 0, the * position of the pyrene ring and $A^{65}$ are not bonded to each other. However, in the case where only one of $A^{61}$, $A^{62}$, $A^{63}$, $A^{64}$ and $A^{65}$ is an N atom, q23 is 1.)

In the general formula (12), the range represented by a group having the same name as the general formula (10) is the same as the preferred range in the general formula (10) of the group.

$R^{201}$, $R^{202}$, $R^{203}$ and $R^{204}$ in the general formula (12) each independently represent a hydrogen atom or a substituent. In the case where $R^{201}$, $R^{202}$, $R^{203}$ and $R^{204}$ represent substituents, the description of the substituents is the same as the description of Rz in the case where $A^{22}$, $A^{23}$, $A^{24}$, $A^{25}$ and $A^{26}$ in the general formula (10) represent CRz. In $R^{201}$, $R^{202}$, $R^{203}$ and $R^{204}$ in the general formula (12), the number of the substituents is preferably 0 or 1.

(Compound Represented by General Formula (3))

In the organic electroluminescent element of the present invention, the compound represented by the general formula (1) is also preferably the compound represented by the general formula (3).

The n32 of the compound represented by the general formula (3) is preferably 1.

In the organic electroluminescent element of the present invention, the compound represented by the general formula (3) is preferably a compound represented by the following general formula (7).

[Chem. 24]

General formula (7)

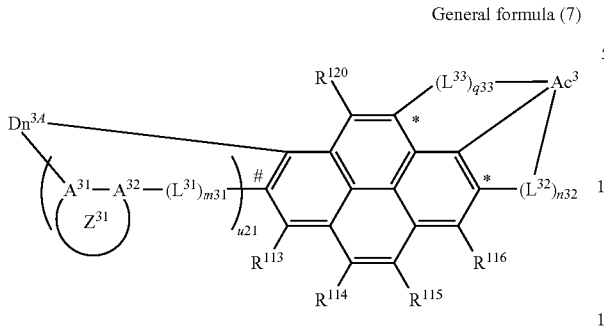

(in which $Dn^{3A}$ represents $NR^{11B}$, an O atom, or an S atom, and when u31 represents 0, $Dn^{3A}$ further has a substituent. $R^{11B}$ represents a substituent. $Ac^3$ represents an electron absorbing substituent, an aryl group having an electron absorbing substituent, or an electron deficient heteroaryl group, $Ac^3$ may further have a substituent. The ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$. $R^{113}$, $R^{114}$, $R^{115}$, $R^{116}$ and $R^{120}$ each independently represent a hydrogen atom or a substituent. $L^{31}$, $L^{32}$ and $L^{33}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, and in the case where u31 is 0, the #position of the pyrene ring and $Dn^{3A}$ are not bonded to each other, and in the case where u31 is 1, the ring formed by the pyrene ring, $Dn^{3A}$ and the ring $Z^{31}$ is not an aromatic ring. m31 represents 0 or 1, and when m31 is 0 and u31 is 1, the #position of the pyrene ring and the ring $Z^{31}$ are directly bonded to each other. n32 and q33 represent 0 or 1, and in the case where any one of n32 and q33 is 0 and n32 or q33 is 1, the rings formed by the pyrene ring, Ac and L or L are not all aromatic rings. In the case where n32 or q33 is 0, the * position of the pyrene ring and $Ac^3$ are not bonded to each other. However, when $Ac^3$ is a pyridine ring, at least one of n32 and q33 is 1.)

In the general formula (7), the range represented by a group having the same name as the general formula (3) is the same as the preferred range in the general formula (3) of the group.

The description and the preferred ranges of $Dn^{3A}$ in the general formula (7) are the same as the description and the preferred ranges of $Dn^1$ in the general formula (1). The substituents which $Dn^{3A}$ in the general formula (7) may further have are the rings formed by $A^{32}$, $A^{33}$, $A^{34}$, $A^{35}$ and $A^{36}$ in the general formula (11) as described later, and these will be described later.

The range of a substituent in the case where $R^{120}$ in the general formula (7) represents a substituent is the same as the range of the substituents other than $Dn^1$ and $Ac^1$, which Cy in the general formula (1) may have, and it is preferable that the substituent do not contain a pyrene skeleton.

In the organic electroluminescent element of the present invention, the compound represented by the general formula (7) is preferably a compound represented by the following general formula (9).

[Chem. 25]

General formula (9)

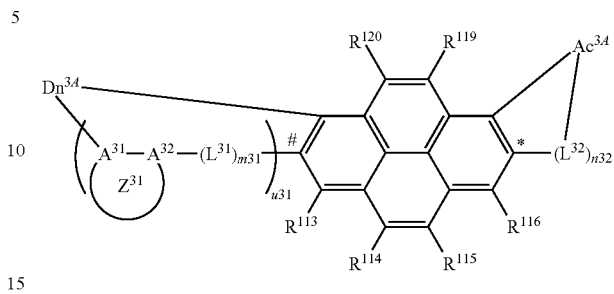

(in which $Dn^{3A}$ represents $NR^{11B}$, an O atom, or an S atom, and when u31 represents 0, $Dn^{3A}$ further has a substituent. $R^{11B}$ represents a substituent. $Ac^{3A}$ represents an electron absorbing substituent, an aryl group having an electron absorbing substituent, or an electron deficient heteroaryl group, $Ac^{3A}$ may further have a substituent. The ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$. $R^{113}$, $R^{114}$, $R^{115}$, $R^{116}$, $R^{119}$ and $R^{120}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. u31 represents 0 or 1, and in the case where u31 is 0, the #position of the pyrene ring and $Dn^{3A}$ are not bonded to each other, and in the case where u31 is 1, the ring formed by the pyrene ring, $Dn^{3A}$ and the ring $Z^{31}$ is not an aromatic ring. m31 represents 0 or 1, and when m31 is 0 and u31 is 1, the #position of the pyrene ring and the ring $Z^{31}$ are directly bonded to each other. n32 represents 0 or 1, and in the case where n32 is 1, the rings formed by the pyrene ring, $Ac^{3A}$ and $L^{32}$ are not all aromatic rings. In the case where n32 is 0, the * position of the pyrene ring and $Ac^{3A}$ are not bonded to each other. However, when $Ac^{3A}$ is a pyridine ring, n32 is 1.)

In the general formula (9), the range represented by a group having the same name as the general formula (7) is the same as the preferred range in the general formula (7) of the group.

The description and the preferred ranges of $Ac^{3A}$ in the general formula (9) are the same as the description and the preferred ranges of $Ac^3$ in the general formula (7). The substituents which $Ac^{3A}$ in the general formula (9) may further have are the rings formed by $A^{61}$, $A^{62}$, $A^{63}$, $A^{64}$, and $A^{65}$ in the general formulae (11) and (13) as described later, and these will be described later.

The range of the substituent in the case where $R^{119}$ in the general formula (9) represents a substituent is the same as the range of the substituents other than $Dn^1$ and $Ac^1$, which Cy in the general formula (1) may have, and it is preferable that the substituent do not contain a pyrene skeleton.

In the organic electroluminescent element of the present invention, the compound represented by the general formula (9) is preferably a compound represented by the following general formula (11).

[Chem. 26]

General formula (11)

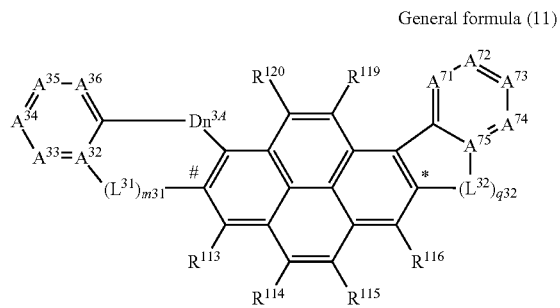

(in which $Dn^{34}$ represents $NR^{11B}$, an O atom, or an S atom, and $R^{11B}$ represents a substituent. $A^{32}$, $A^{33}$, $A^{34}$, $A^{35}$, $A^{36}$, $A^{71}$, $A^{72}$, $A^{73}$, $A^{74}$ and $A^{75}$ each independently represent CRz' (two adjacent CRz's may be combined with each other to form a 5- or 6-membered ring) or an N atom. In the case where $A^{71}$, $A^{72}$, $A^{73}$, $A^{74}$ and $A^{75}$ are not all N atoms, at least one Rz' in CRz's represented by $A^{71}$, $A^{72}$, $A^{73}$, $A^{74}$ and $A^{75}$ represents an electron absorbing substituent. $R^{113}$, $R^{114}$, $R^{115}$, $R^{116}$, $R^{119}$ and $R^{120}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. m31 represents 0 or 1, and when m31 is 0, the #position of the pyrene ring and $A^{32}$ are directly bonded to each other. n32 represents 0 or 1, and in the case where n32 is 1, the rings formed by the pyrene ring, $Ac^{34}$ and $L^{32}$ are not all aromatic rings. In the case where n32 is 0, the * position of the pyrene ring and $A^{75}$ are not bonded to each other. However, in the case where only one of $A^{71}$, $A^{72}$, $A^{73}$, $A^{74}$ and $A^{75}$ is an N atom, n32 represents 1.)

In the general formula (11), the range represented by a group having the same name as the general formula (9) is the same as the preferred range in the general formula (9) of the group.

The preferred ranges of $A^{32}$, $A^{33}$, $A^{34}$, $A^{35}$ and $A^{36}$ in the general formula (11) are the same as the preferred ranges of $A^{22}$, $A^{23}$, $A^{24}$, $A^{25}$ and $A^{26}$ in the general formula (10).

The preferred ranges of $A^{71}$, $A^{72}$, $A^{73}$, $A^{74}$ and $A^{75}$ in the general formula (11) are the same as the preferred ranges of $A^{61}$, $A^{62}$, $A^{63}$, $A^{64}$ and $A^{65}$ in the general formula (10).

In the organic electroluminescent element of the present invention, the compound represented by the general formula (11) is preferably a compound represented by the following general formula (13).

General formula (13)

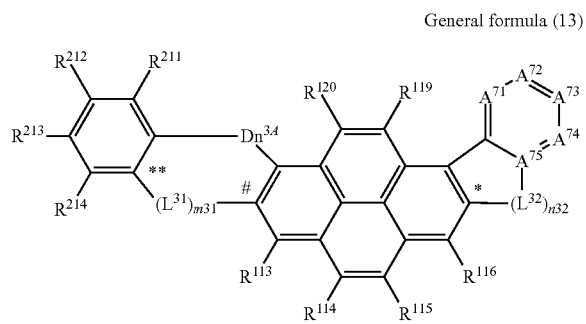

(in which $Dn^{34}$ represents $NR^{11B}$, an O atom, or an S atom, and $R^{11B}$ represents a substituent. $A^{71}$, $A^{72}$, $A^{73}$, $A^{74}$ and $A^{75}$ each independently represent CRz' (two adjacent CRz's may be combined with each other to form a 5- or 6-membered ring) or an N atom. In the case where $A^{71}$, $A^{72}$, $A^{73}$, $A^{74}$ and $A^{75}$ are not all N atoms, at least one Rz' in CRz's represented by $A^{71}$, $A^{72}$, $A^{73}$, $A^{74}$ and $A^{75}$ represents an electron absorbing substituent. $R^{113}$, $R^{114}$, $R^{115}$, $R^{116}$, $R^{119}$, $R^{120}$, $R^{221}$, $R^{212}$, $R^{213}$ and $R^{214}$ each independently represent a hydrogen atom or a substituent. $L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent. m31 represents 0 or 1, and when m31 is 0, the ** position and the #position of the pyrene ring are directly bonded to each other. n32 represents 0 or 1, and in the case where n32 is 0, the * position of the pyrene ring and $A^{75}$ are not bonded to each other. However, in the case where only one of $A^{71}$, $A^{72}$, $A^{73}$, $A^{74}$ and $A^{75}$ is an N atom, n32 represents 1.)

In the general formula (13), the range represented by a group having the same name as the general formula (11) is the same as the preferred range in the general formula (11) of the group.

The preferred ranges of $R^{211}$, $R^{212}$, $R^{213}$ and $R^{214}$ in the general formula (13) are the same as the preferred ranges of $R^{201}$, $R^{202}$, $R^{203}$ and $R^{204}$ in the general formula (12).

When the compound represented by the general formula (1) is used as a light emitting material, the maximum light emitting wavelength of the organic electroluminescent element is usually less than 455 nm, preferably 400 nm or more and less than 455 nm, more preferably 420 nm or more and less than 455 nm, still more preferably 430 nm or more and less than 455 nm, and most preferably 440 nm or more and less than 455 nm from the viewpoint of obtaining high blue light emission of color purity.

The molecule weight of the compound represented by the general formula (1) is preferably 1000 or less, more preferably 900 or less, particularly preferably 850 or less, and still more preferably 800 or less. By reducing the molecule weight, the sublimation temperature can be lowered, and thus, the thermal decomposition of the compound during deposition can be prevented. Further, by reducing the deposition time, the energy required for deposition can also be inhibited. Here, with the material having a high sublimation temperature, thermal decomposition can occur during long-term deposition, and thus, from the viewpoint of deposition suitability, sublimation temperatures that are not too high are desirable. The sublimation temperature (which means a temperature for reduction by 10% by mass in the specification) of the compound represented by the general formula (1) is preferably 300° C., more preferably 285° C. or lower, and still more preferably 270° C. or lower.

Specific examples of the compound represented by the general formula (1) are shown below, but it should not be construed that the compound represented by the general formula (1) which can be used in the present invention is limited to the specific examples.

[Chem. 28]
Compound 1
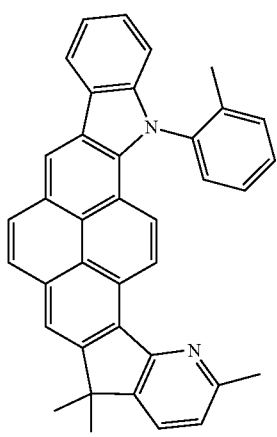
Compound 2
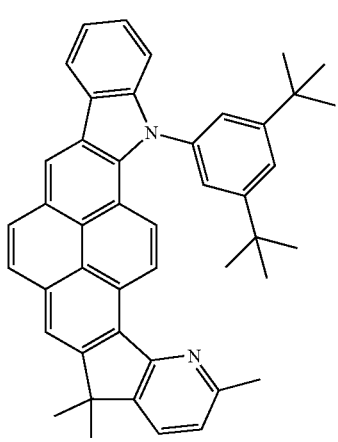
Compound 3
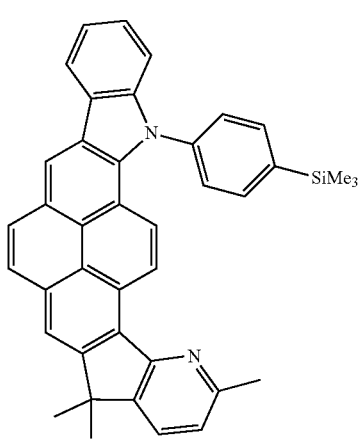
Compound 4
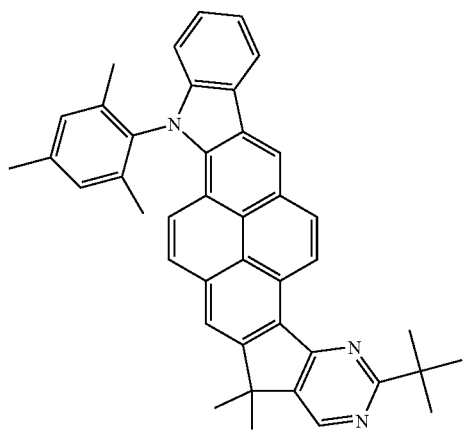
Compound 5
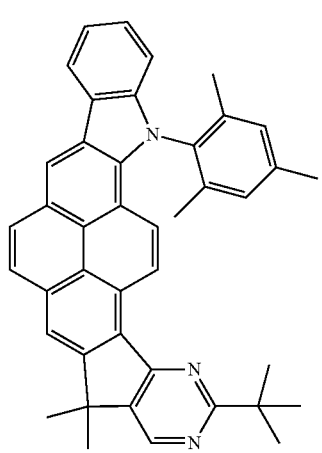
Compound 6
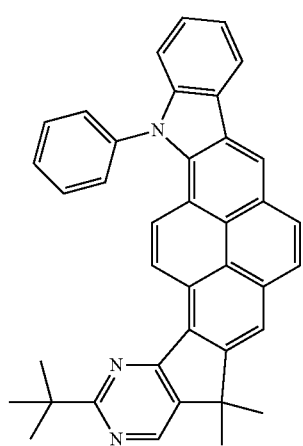

Compound 7
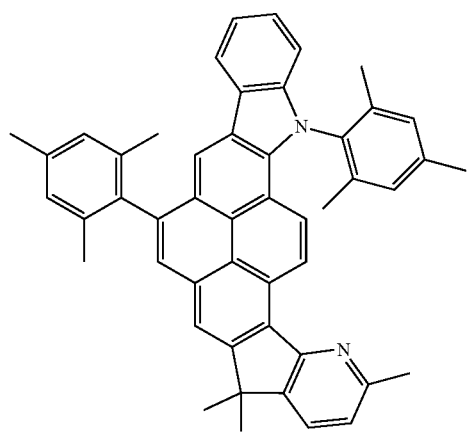
Compound 8
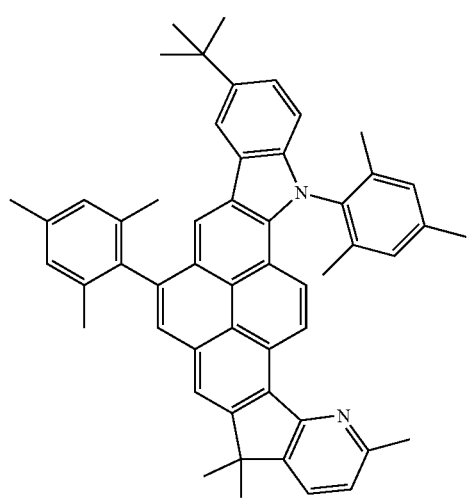
Compound 9
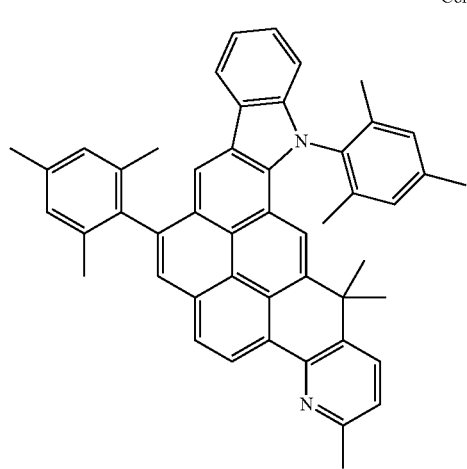
Compound 10
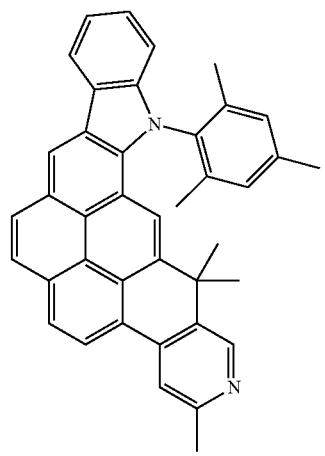
Compound 11
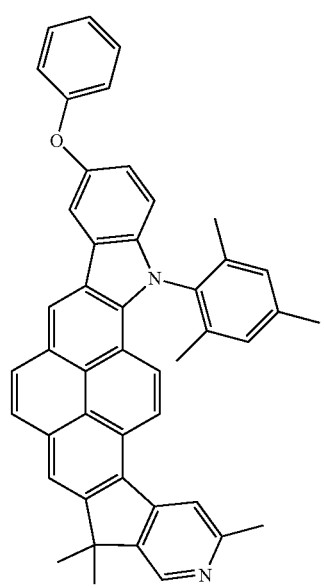
Compound 12
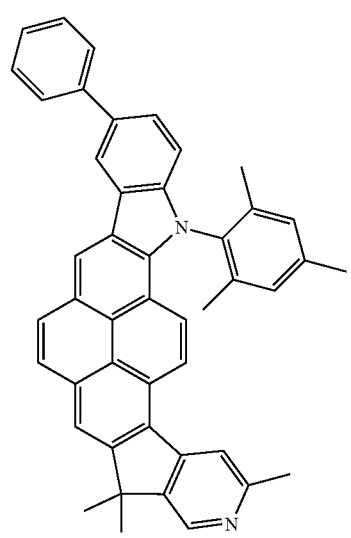

-continued
[Chem. 29]
Compound 13
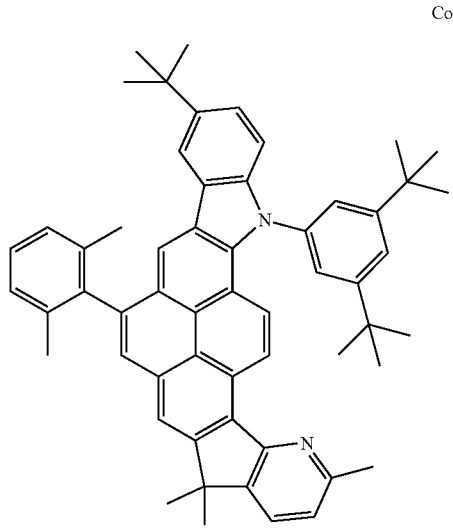
Compound 14
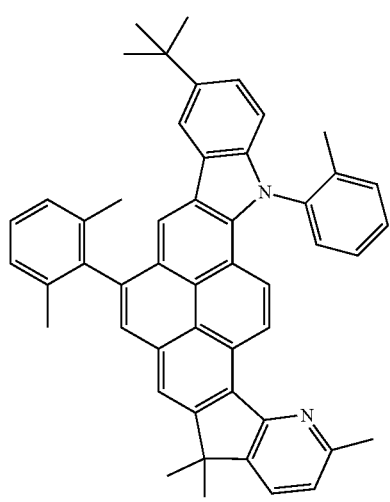
Compound 15
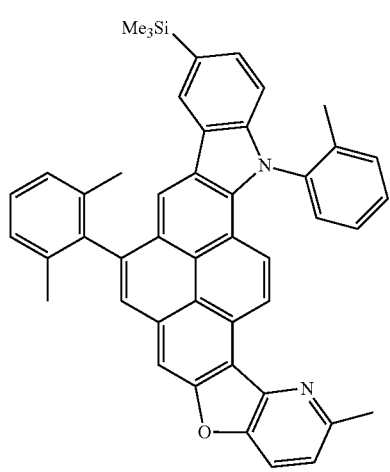
-continued
Compound 16
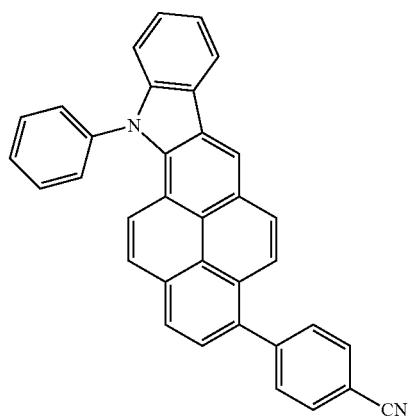
Compound 17
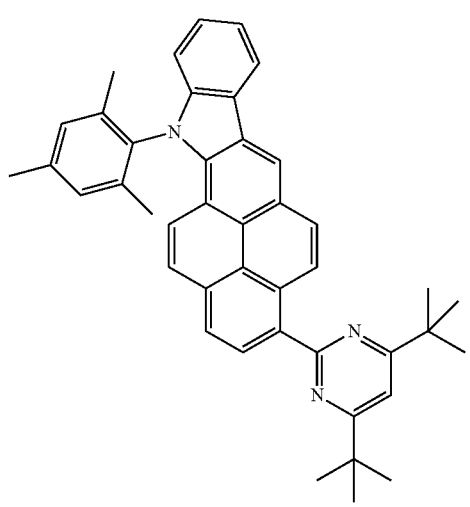
Compound 18
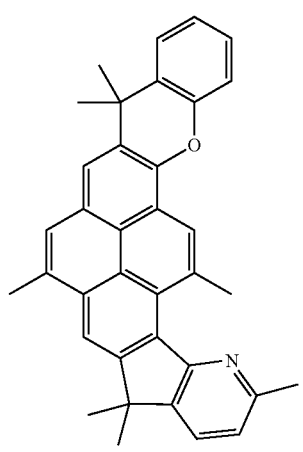

Compound 19
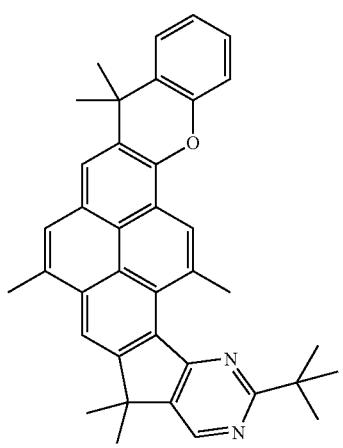
Compound 20
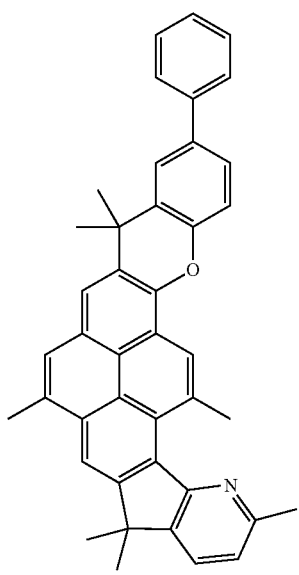
Compound 21
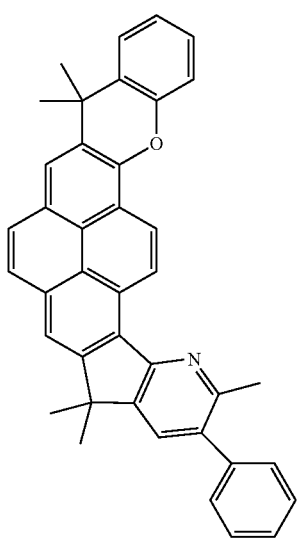
Compound 22
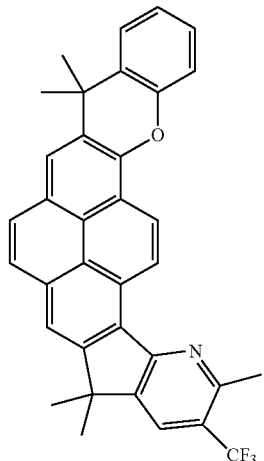
Compound 23
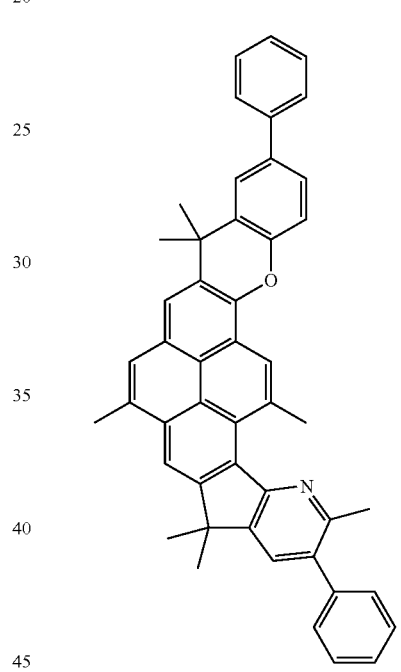
Compound 24
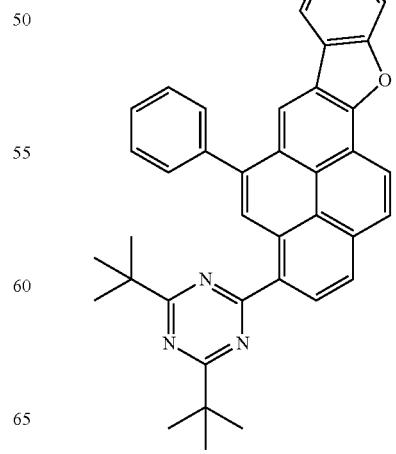

[Chem. 30]
Compound 25
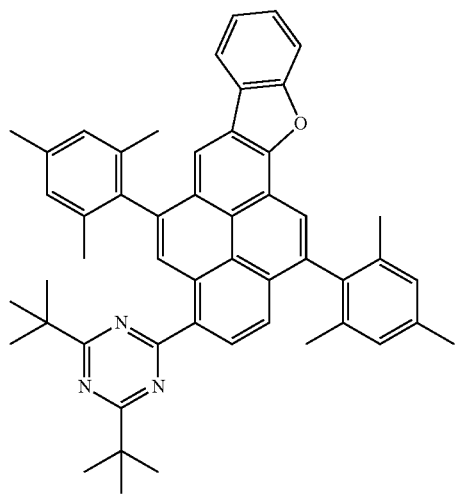
Compound 26
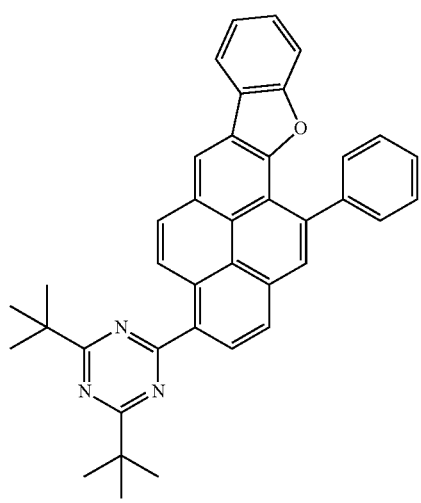
Compound 27
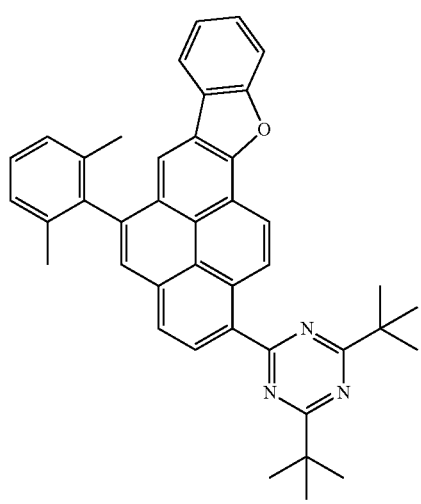
Compound 28
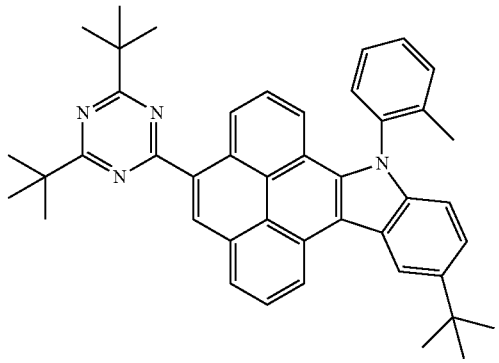
Compound 29
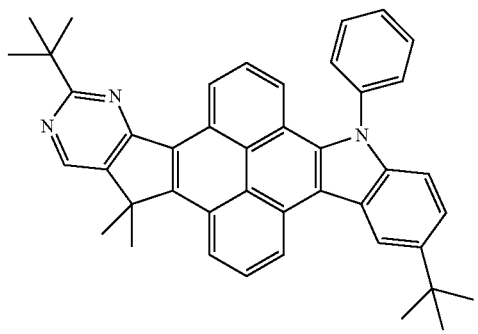
Compound 30
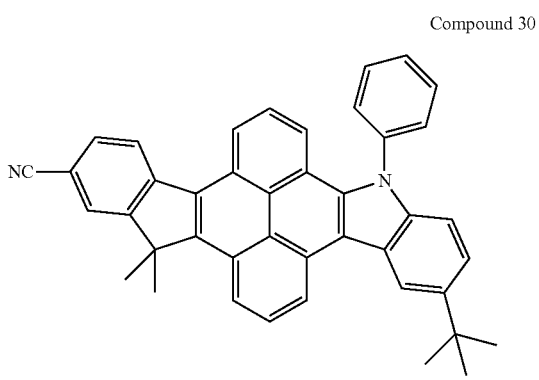
The compound represented by the general formula (1) can be synthesized by the method described in JP-A-2010-111620, Korean Patent Publication No. 2011-0041726, or the like, or a combination of other known reactions. Further, it is possible to synthesize the compound by, for example, a combination of the following schemes.

[Chem. 31]

Scheme

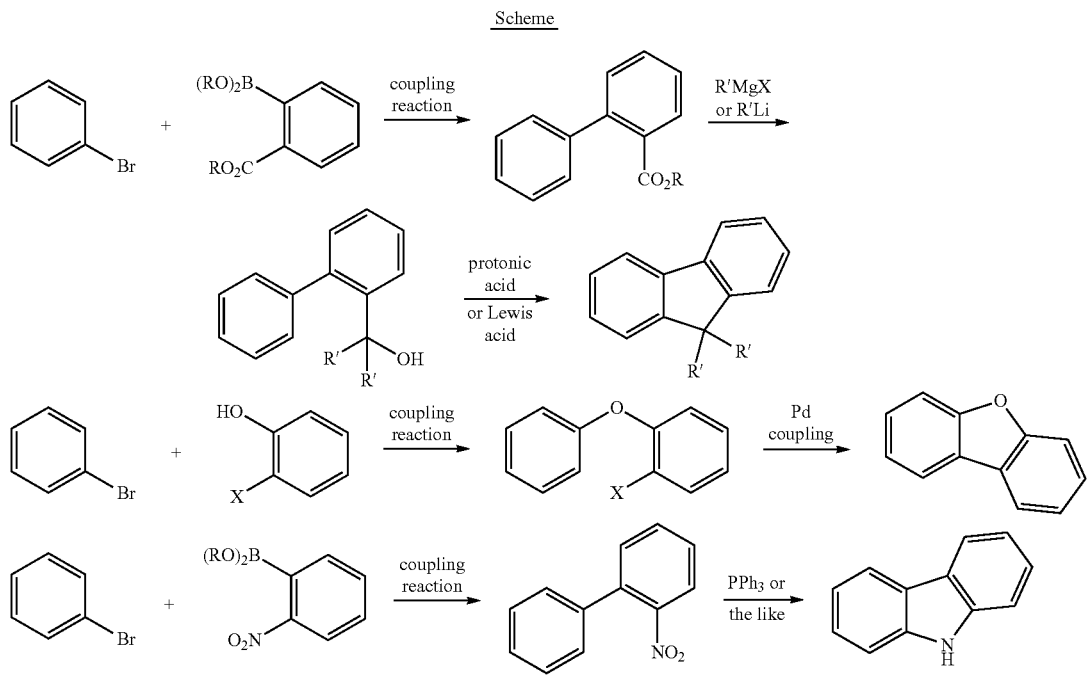

After the synthesis, purification is preferably carried out by column chromatography, recrystallization, or the like, and then by sublimation purification. By the sublimation purification, organic impurities can be separated and inorganic salts, residual solvents, or the like can be removed effectively.

In the case of the use as a light emitting material using the compound represented by the general formula (1), its maximum light emitting wavelength is preferably less than 455 nm, more preferably 400 nm or more and less than 455 nm, particularly preferably 420 nm or more and less than 455 nm, still more preferably 430 nm or more and less than 455 nm, and most preferably 440 nm or more and less than 455 nm.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which the light emitting layer includes a compound represented by the general formula (1).

The configuration of the organic electroluminescent element of the present invention is not particularly limited. FIG. 1 shows one example of the configuration of the organic electroluminescent element of the present invention. The organic electroluminescent element 10 in FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed descriptions described in this publication can be applied to the present invention.

Hereinafter, preferred embodiments of the organic electroluminescent element of the present invention will be described in detail in the order of the substrate, the electrodes, the organic layer, a protective layer, a sealing enclosure, a driving method, a light emitting wavelength, and applications.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element of the present invention has at least one organic layer including a light emitting layer, disposed between the electrodes, in which the organic layer includes the compound represented by the general formula (1). For the organic electroluminescent element of the present invention, at least one organic layer including the compound represented by the general formula (1) is preferably a light emitting layer.

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred embodiments of the respective layers constituting the organic layer, and the materials used in the respective layers in the organic electroluminescent element of the present invention will be described in detail in order.

(Configuration of Organic Layer)

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (1) is contained in the organic layer disposed between the electrodes of the organic electroluminescent element, and preferably contained in the light emitting layer in the organic layer disposed between the electrodes.

The compound represented by the general formula (1) may be contained in another organic layer of the organic electroluminescent element of the present invention. Examples of the organic layer other than the light emitting layer, which may contain the compound represented by the general formula (1), include a hole injecting layer, a hole transporting layer, an electron transporting layer, an electron injecting layer, an exciton blocking layer, and a charge blocking layer (a hole blocking layer, an electron blocking layer, or the like), preferably any one of an exciton blocking layer, a charge blocking layer, an electron transporting layer, and an electron injecting layer, and more preferably an exciton blocking layer, a charge blocking layer, or an electron transporting layer.

In the case where the compound represented by the general formula (1) is contained in the light emitting layer, the compound represented by the general formula (1) is contained in the light emitting layer, preferably in the amount of 0.1% by mass to 100% by mass, more preferably 1% by mass to 50% by mass, and still more preferably 2% by mass to 20% by mass, with respect to the total mass.

In the case where the compound represented by the general formula (1) is contained in an organic layer other than the light emitting layer, the compound represented by the general formula (1) is contained in the organic layer, preferably in the amount of 70% by mass to 100% by mass, more preferably 80% by mass to 100% by mass, and still more preferably 90% by mass to 100% by mass, with respect to the total mass.

(Method for Forming Organic Layer)

The respective organic layers in the organic electroluminescent element of the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element of the present invention, the light emitting layer disposed between the pair of electrodes is preferably formed by a vacuum deposition process or a wet process. Further, the light emitting layer is more preferably formed by deposition of a composition further including at least the compound represented by the general formula (1).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, the light emitting layer contains the compound represented by the general formula (1), and it is a preferred embodiment to use the compound represented by the general formula (1) as a light emitting material of the light emitting layer. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably 5% or less, more preferably 3% or less, and still more preferably 1% or less, with respect to the total amount of light emission in the whole of the element. The compound represented by the general formula (1) may be used as a host material of the light emitting layer.

(Light Emitting Material)

In the organic electroluminescent element of the present invention, the compound represented by the general formula (1) is preferably used as the light emitting material, but in this case, a combination of the compound with light emitting materials different from the compound represented by the general formula (1) can be used. Further, in the organic electroluminescent element of the present invention, in the case where the compound represented by the general formula (1) is used as a host material of the light emitting layer or in the case where the compound represented by the general formula (1) is used in an organic layer other than the light emitting layer, it is used in the light emitting materials different from the compound represented by the general formula (1).

The light emitting material which can be used in the present invention may be any one of a phosphorescent light emitting material, a fluorescent light emitting material, and the like. Further, the light emitting layer in the present invention may contain two or more kinds of light emitting materials in order to improve the color purity or widen the light emitting wavelength region.

The fluorescent light emitting material and the phosphorescent material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, the detailed descriptions thereon in these publications can be applied to the present invention.

Examples of the phosphorescent light emitting material which can be used in the present invention include phosphorescent light emitting materials described in patent documents, for example, U.S. Pat. Nos. 6,303,238, 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, European Patent Application, Publication No. 211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, with Ir complexes, Pt complexes, and Re complexes being particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, and chromaticity, Ir complexes and Pt complexes are particularly preferred, and Ir complexes are the most preferred.

The kind of the fluorescent light emitting material which can be used in the present invention is not particularly limited, but examples thereof include those other than the compound represented by the general formula (1), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

In addition, the light emitting layer may be made of a single layer or two or more layers. The respective layers may include the same light emitting materials or host materials, and may also include different materials from each other over layers. In the case where a plurality of light emitting layers are present, the respective light emitting layers may emit light in different luminous colors from each other.

(Host Material)

The host material is a compound that usually plays a role in injecting or transporting charges in the light emitting layer and is also a compound which does not substantially emit light in itself. As used herein, it is meant by the terms "which does not substantially emit light" that the amount of light emitting from the compound which does not substantially emit light is preferably 5% or less, more preferably 3% or less, and still more preferably 1% or less of the total amount of light emitting in the whole of the element.

Examples of the hose material which can be used in the organic electroluminescent element of the present invention include the following compounds, other than compound represented by the general formula (1):

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused ring aromatic hydrocarbon compounds (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

The host material that can be used in the light emitting layer in the organic electroluminescent element of the present invention may be a host material having hole transporting properties or a host material having electron transporting properties.

In the light emitting layer, the singlet lowest excited energy ($S_1$ energy) in the film state of the host material is preferably higher than the $S_1$ energy of the light emitting material from the viewpoints of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the $S_1$ of the light emitting material. Further, even in the case where $S_1$ of the host material is higher than the $S_1$ of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Furthermore, the content of the host compound in the light emitting layer in the organic electroluminescent element of the present invention is not particularly limited, but from the viewpoint of luminous efficiency and driving voltage, it is preferably from 15% by mass to 95% by mass, with respect to the total mass of the compounds forming the light emitting layer. When the light emitting layer includes a plurality of kinds of host compounds containing the compound represented by the general formula (1), the content of the compound represented by the general formula (1) is preferably from 50% by mass to 99% by mass, with respect to the total host compounds.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, Anode/hole injecting layer/hole transporting layer/blocking layer/light emitting layer/blocking layer/electron transporting layer/electron injecting layer/cathode.

The organic electroluminescent element of the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element of the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred embodiments of the organic electroluminescent element of the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer preferably includes at least one compound of the compounds represented by the following general formulae (Sa-1), (Sb-1), and (Sc-1).

[Chem. 32]

General formula (Sa-1)

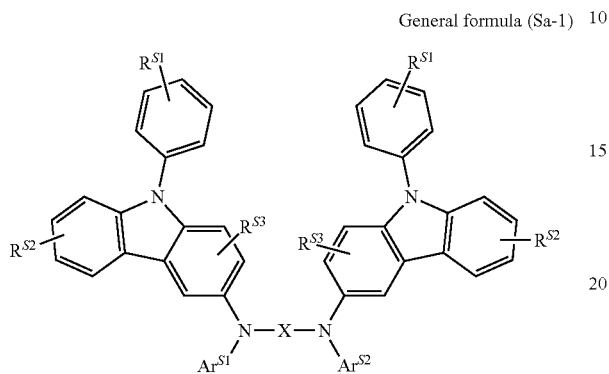

(in which X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 33]

General formula (Sb-1)

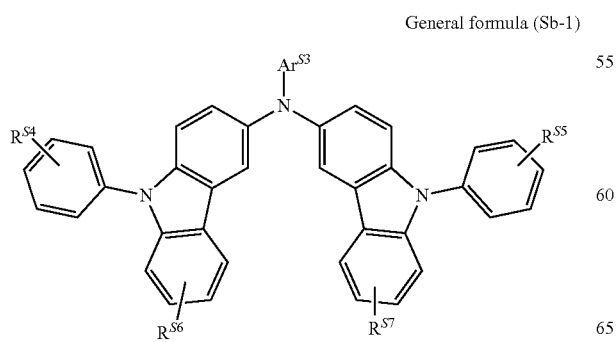

(in which $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 34]

General formula (Sc-1)

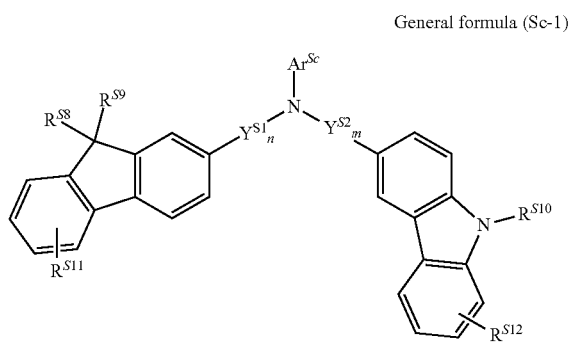

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. X is preferably a substituted or unsubstituted arylene group having 6 to 30 carbon atoms, more preferably having a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene having 1 to 30 carbon atoms, or substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

[Chem. 35]

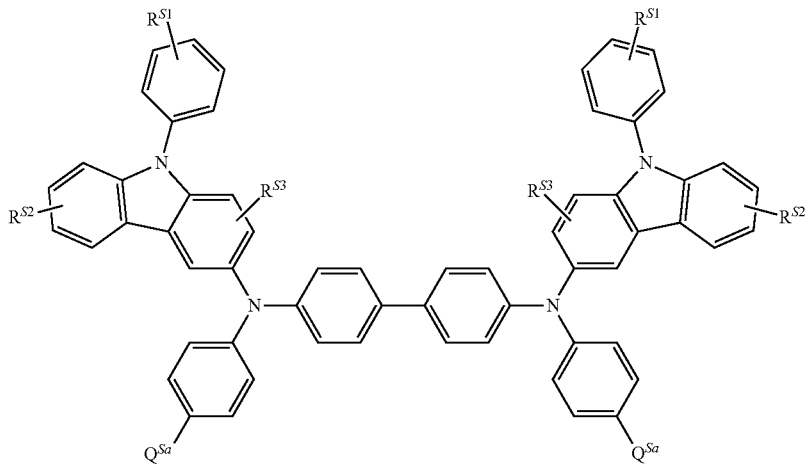

General formula (Sa-2)

(in which $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

[Chem. 36]

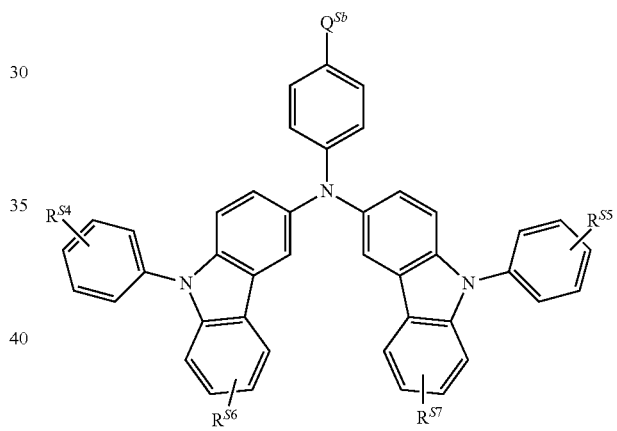

General formula (Sb-2)

(in which $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

[Chem. 37]

General formula (Sc-2)

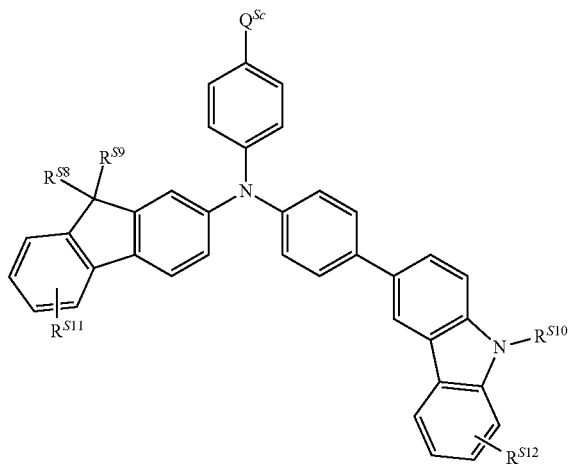

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$ and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 38]

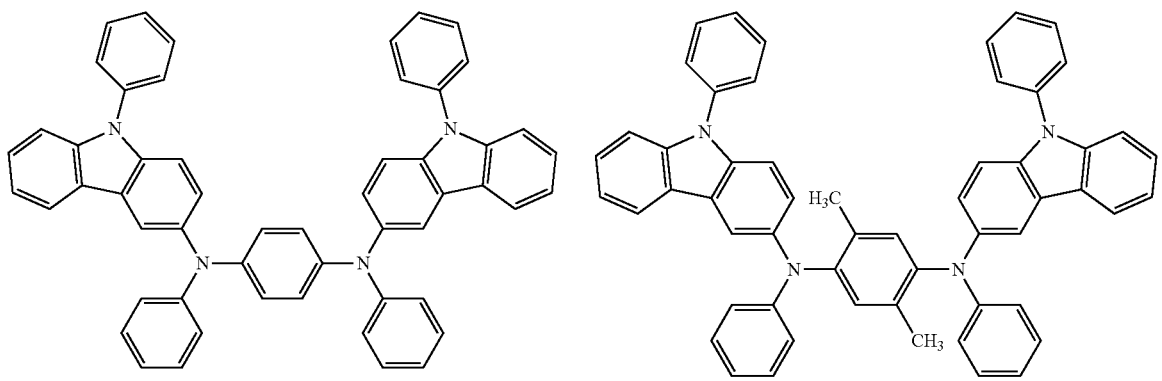

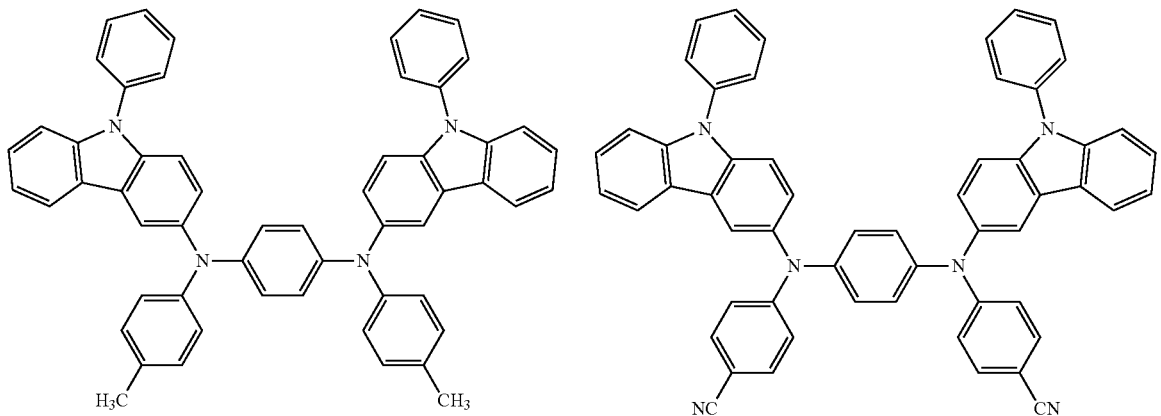
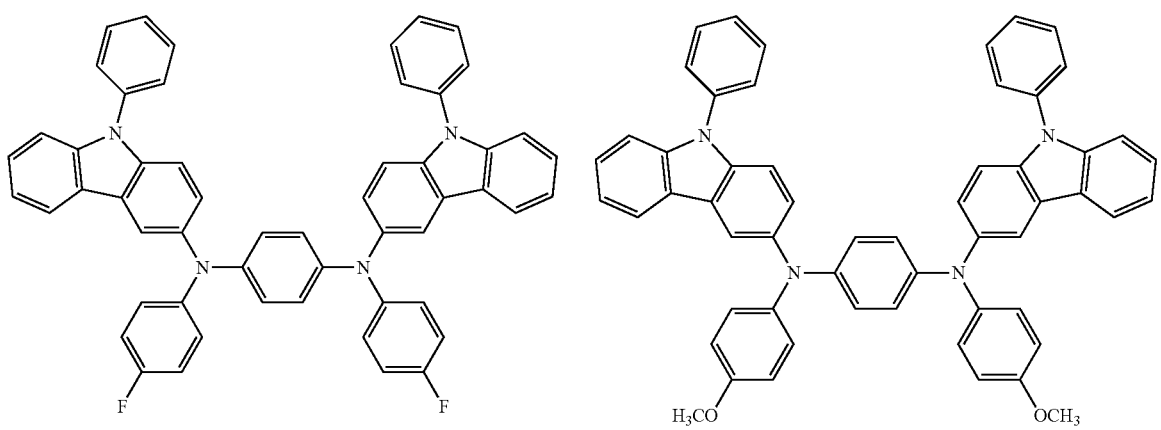
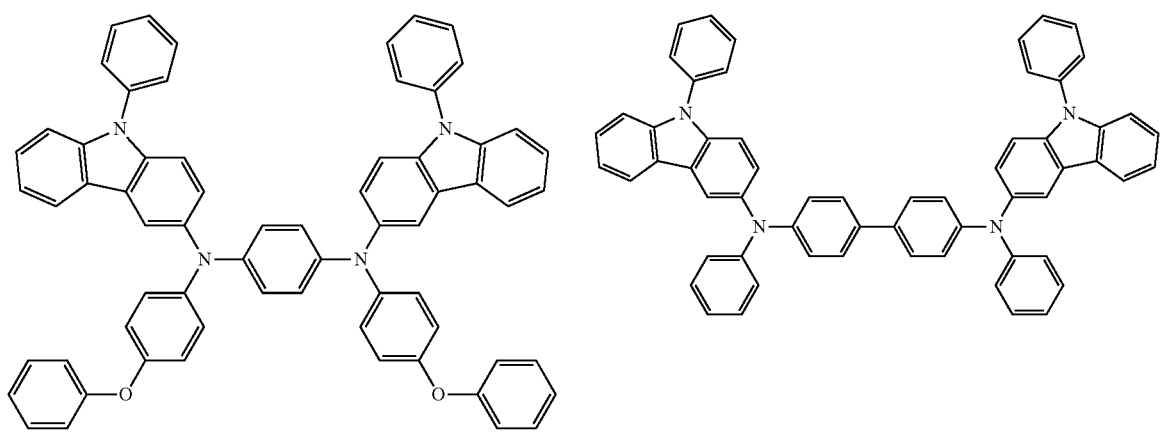

[Chem. 39]
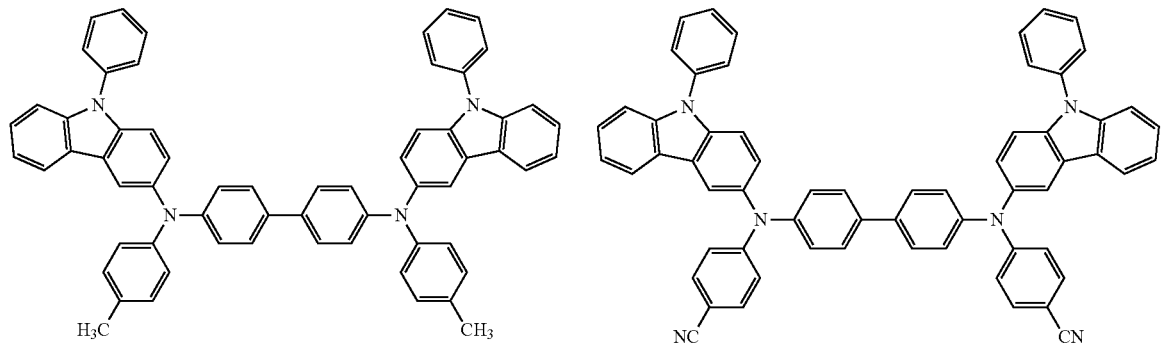
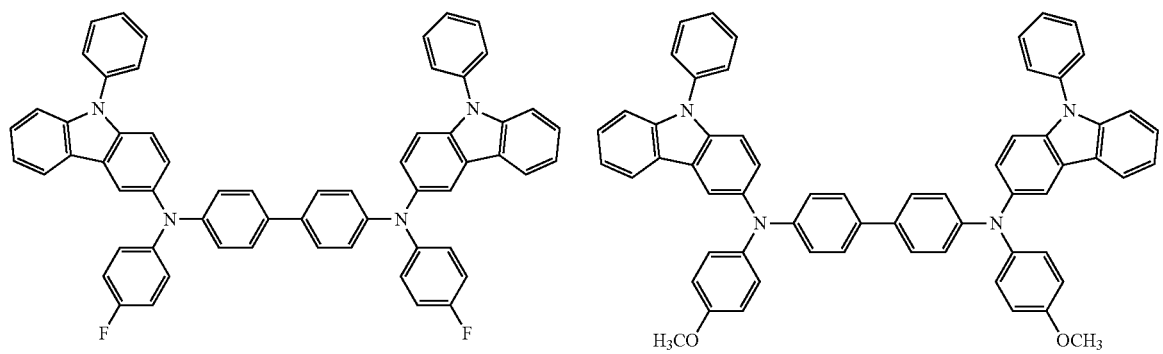
[Chem. 40]
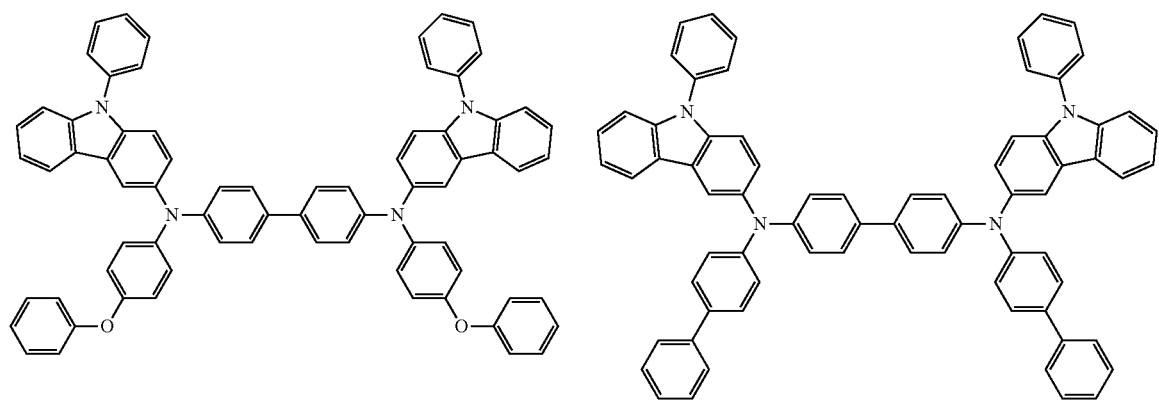
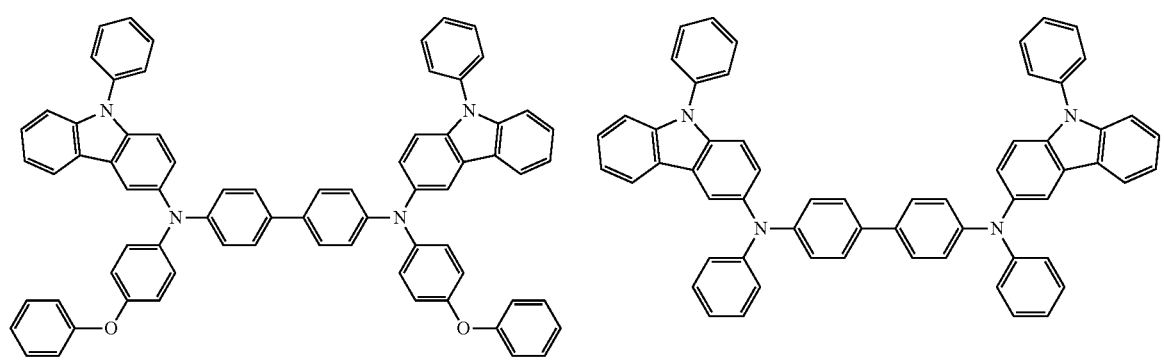

-continued
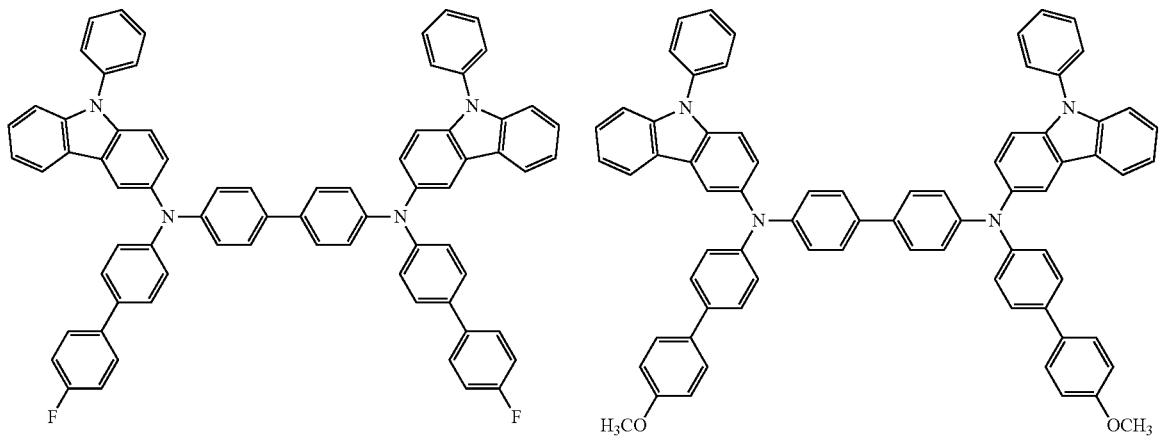
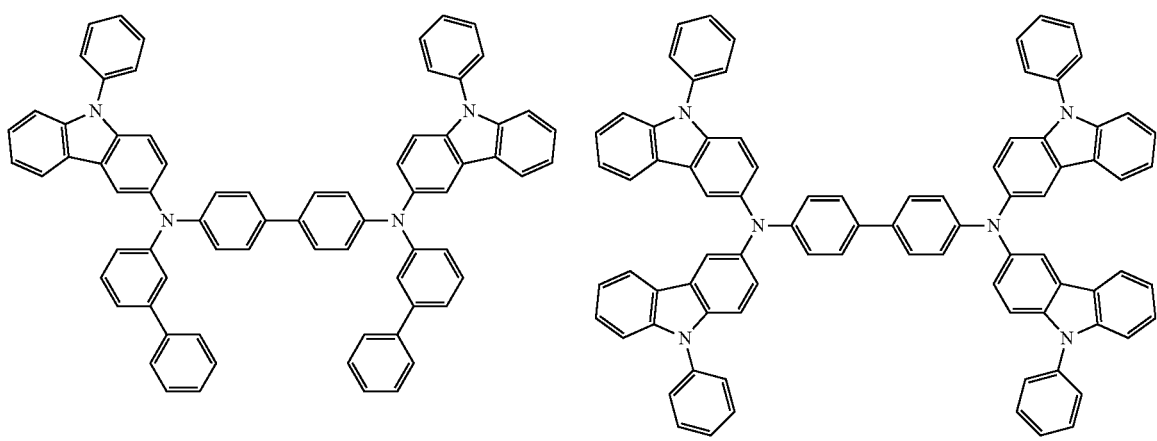
[Chem. 41]
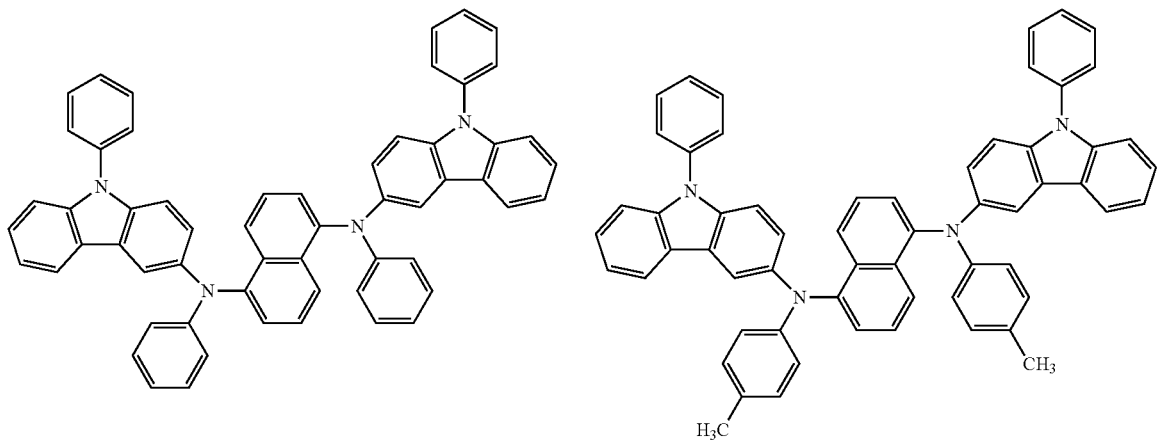

-continued
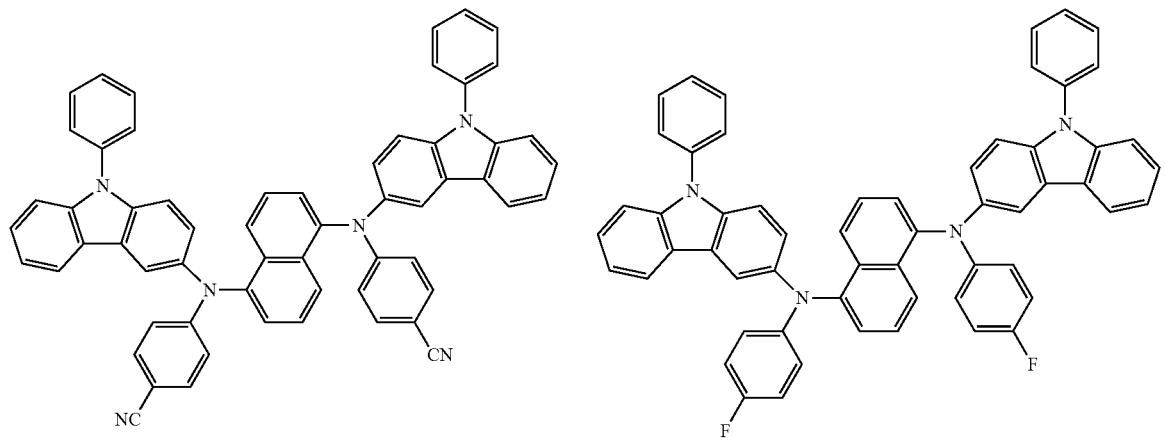
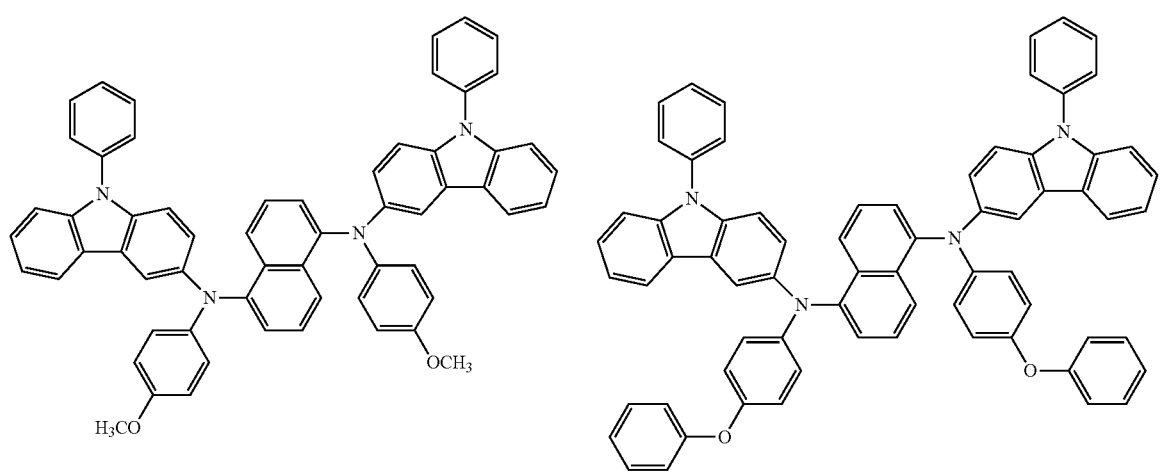
[Chem. 42]
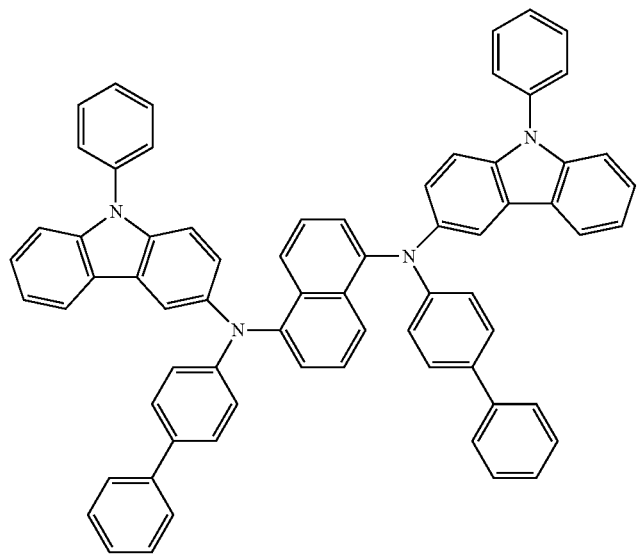

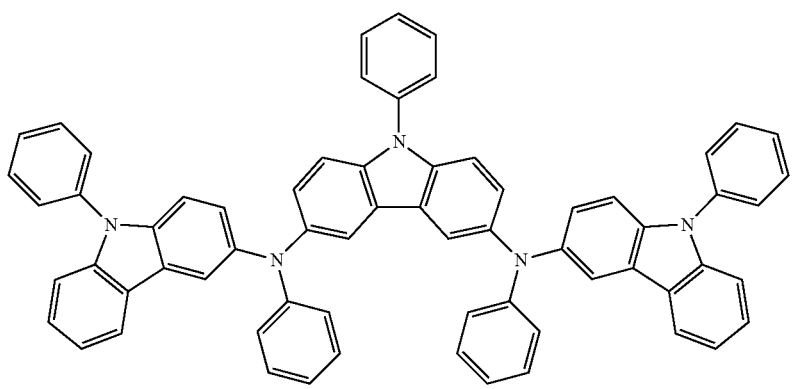
28
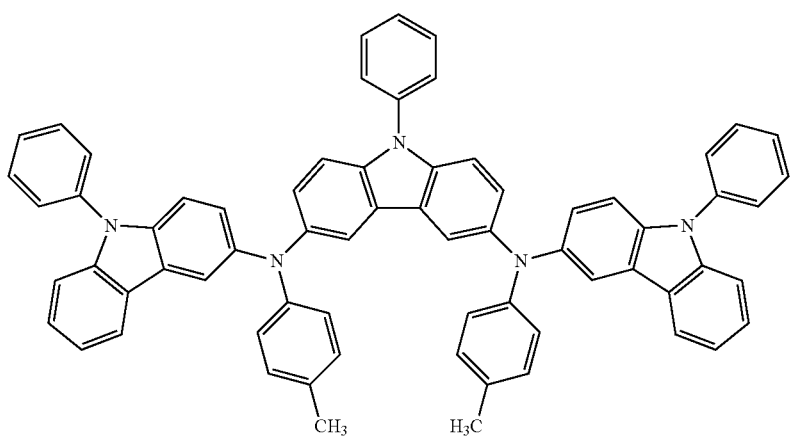
29
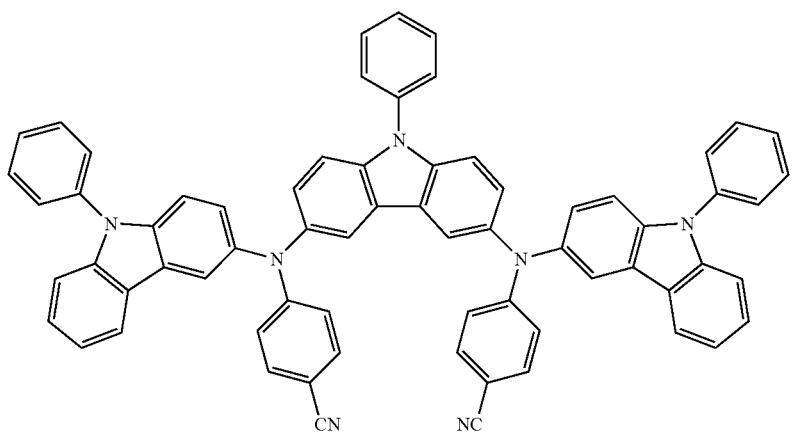
30

-continued
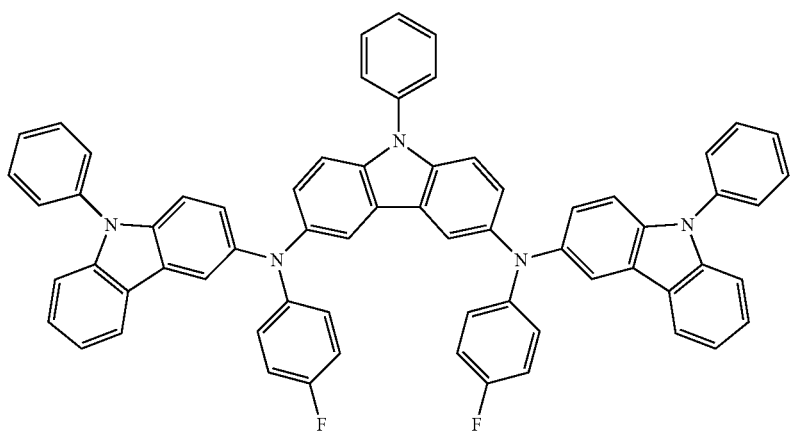
31
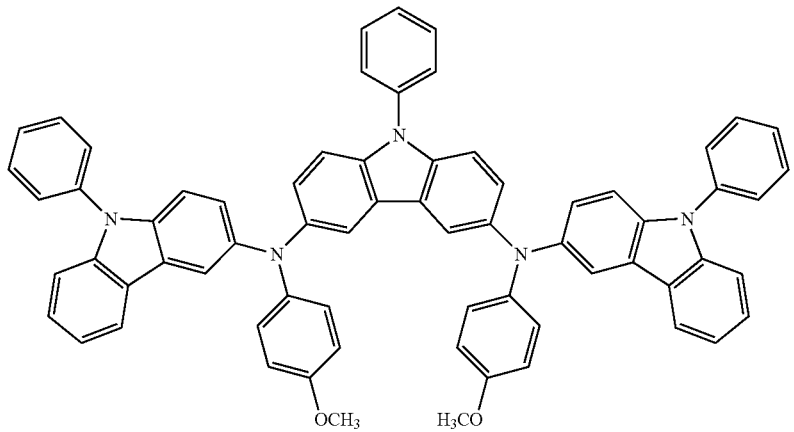
32
[Chem. 43]
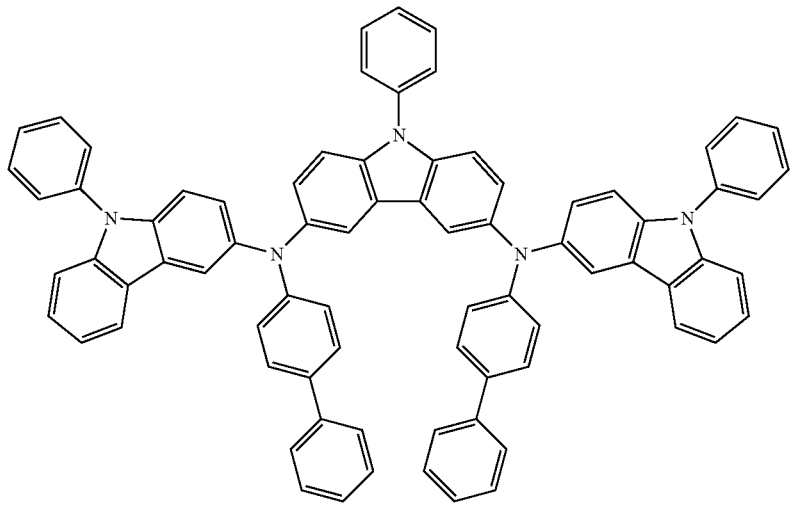
33

34
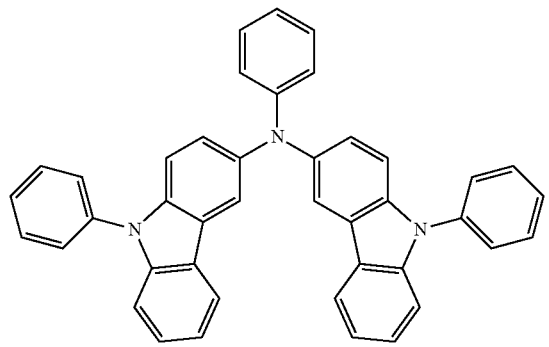
35
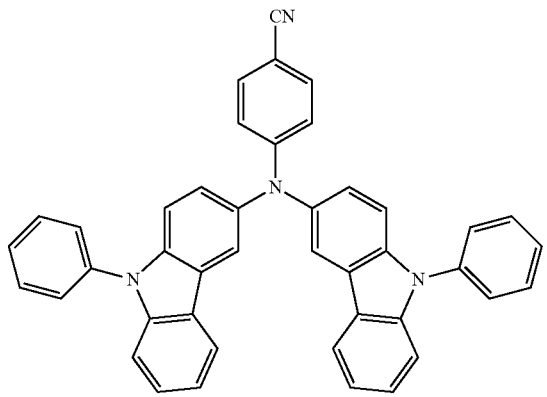
36
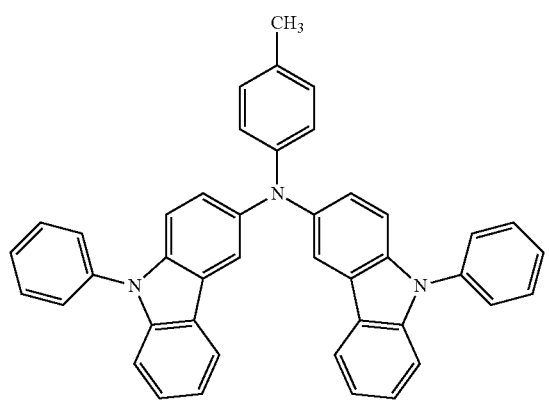
37
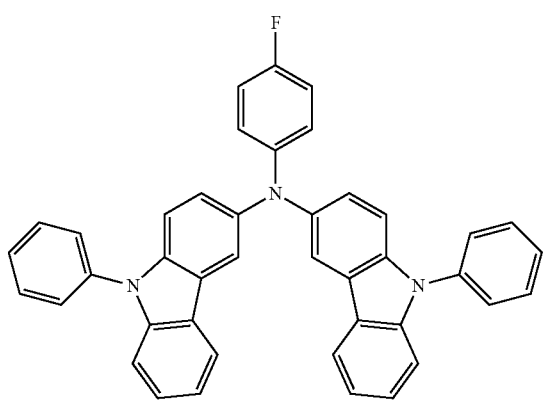
38
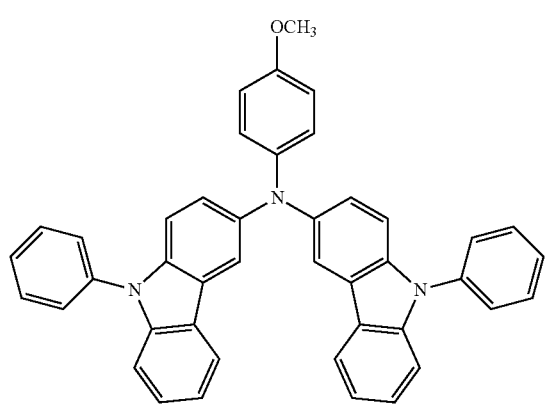

-continued
39 40
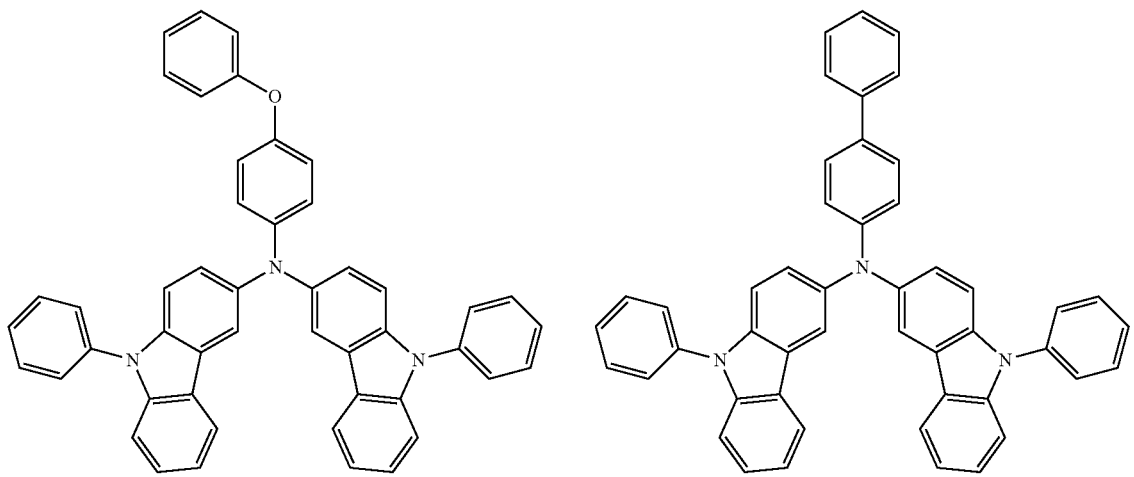
41 42
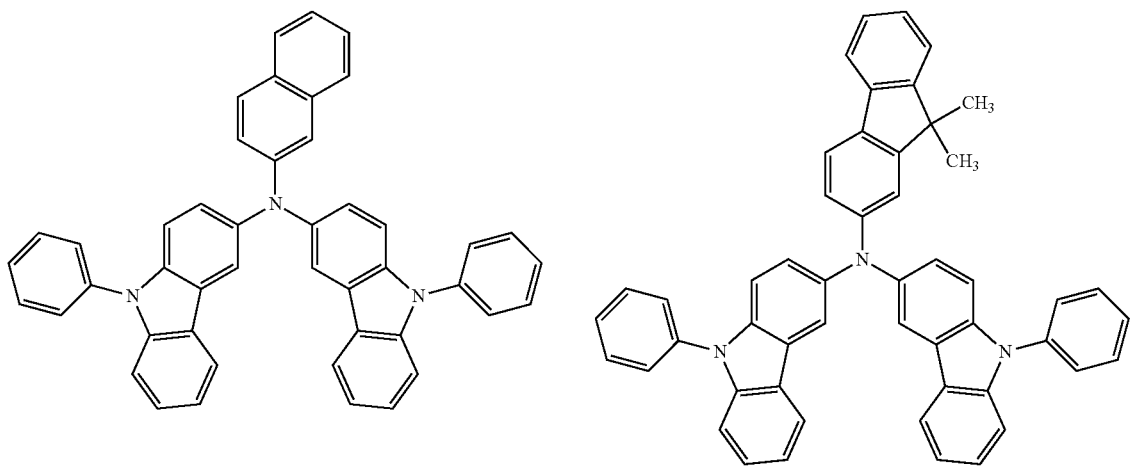
[Chem. 45]
43 44
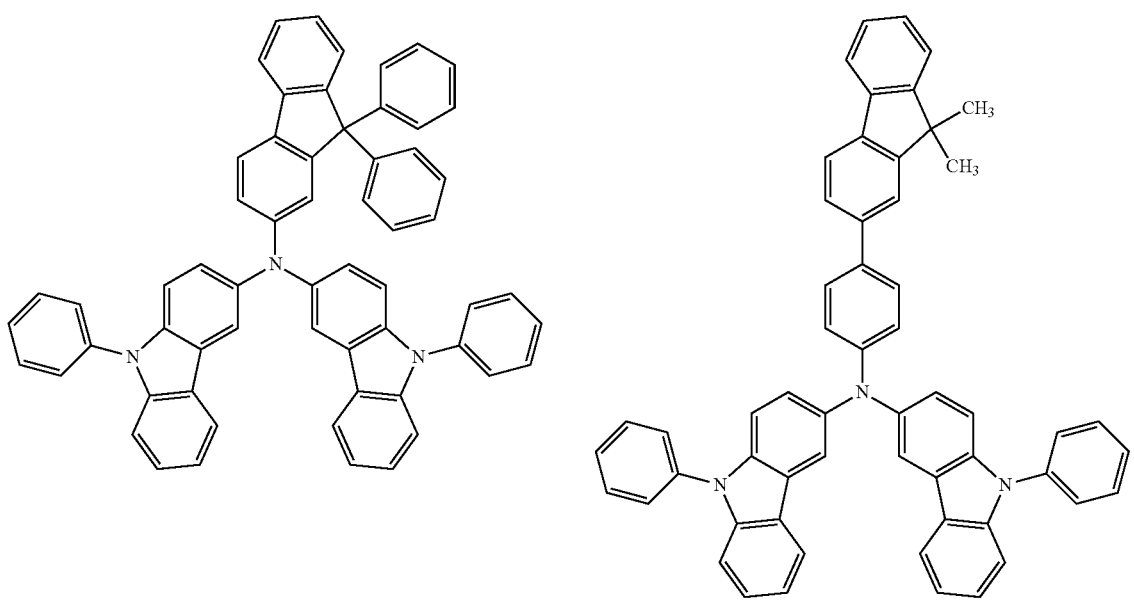

45
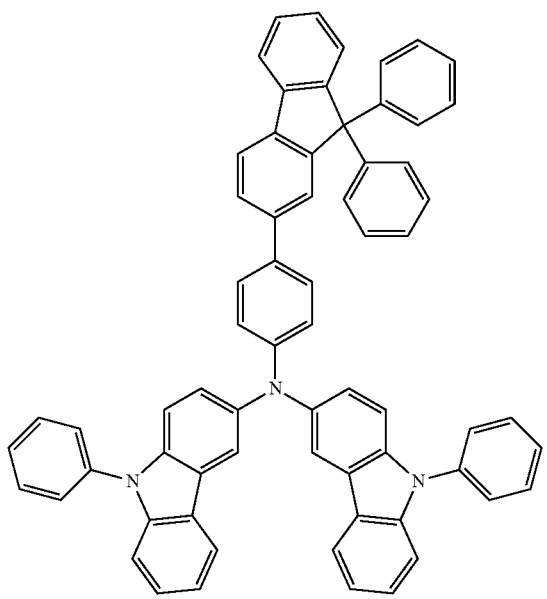
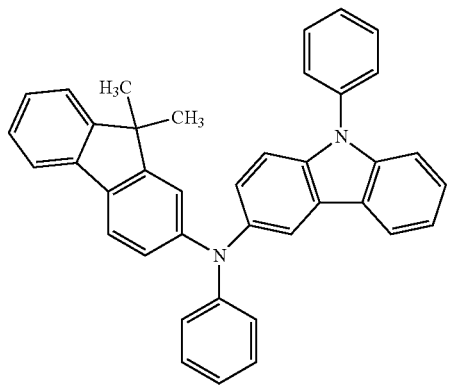
46
[Chem. 46]
47
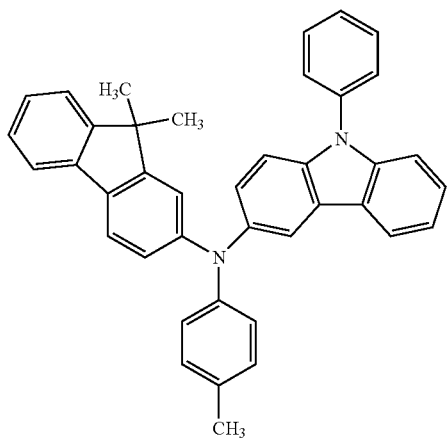
48
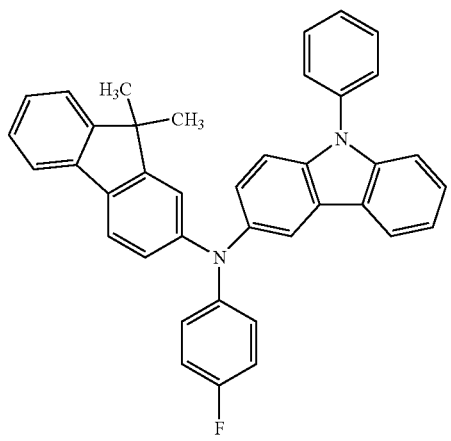
49
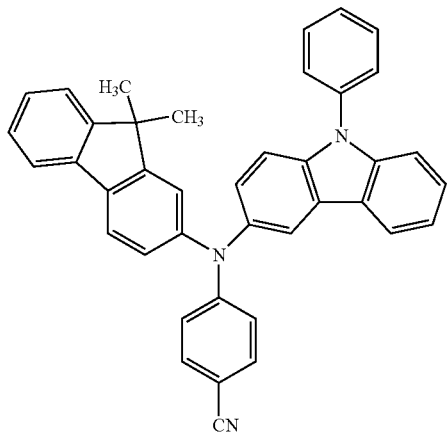
50
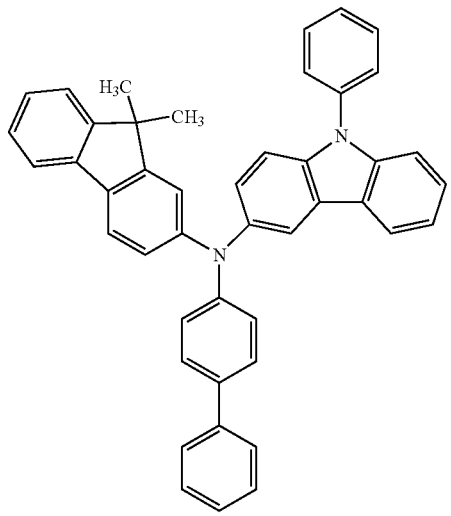

-continued
51
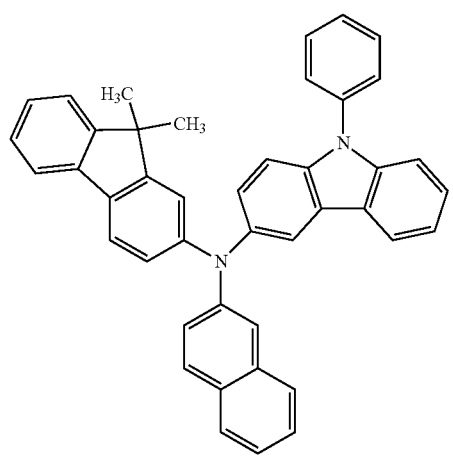
52
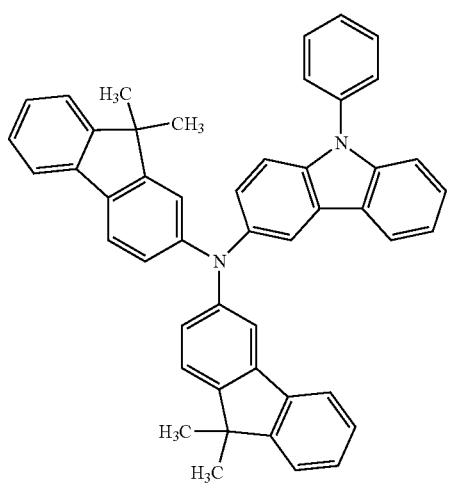
53
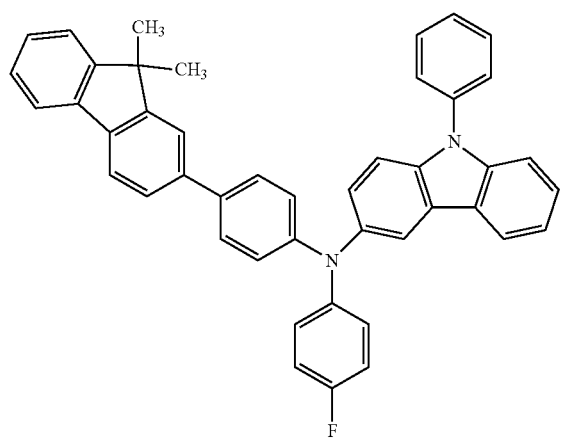
54
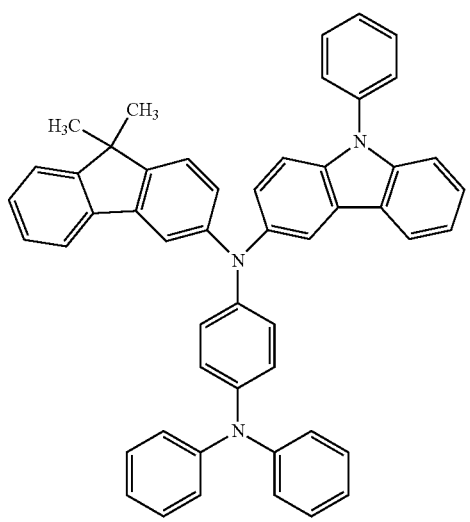
55
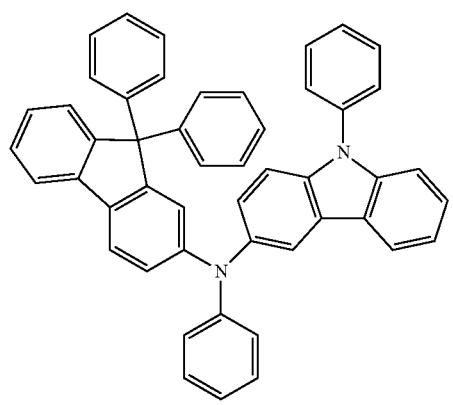

[Chem. 47]
56
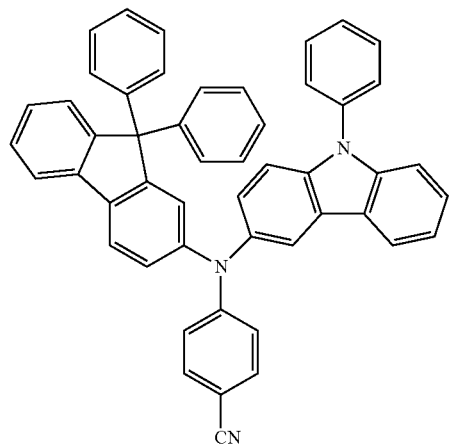
57
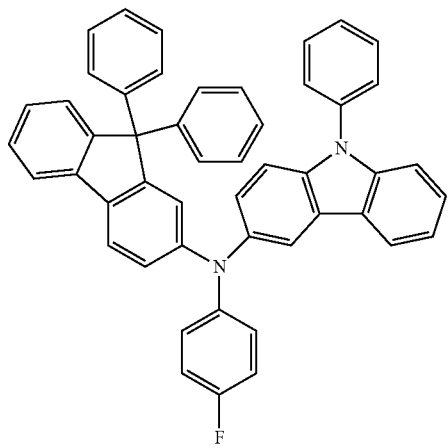
58
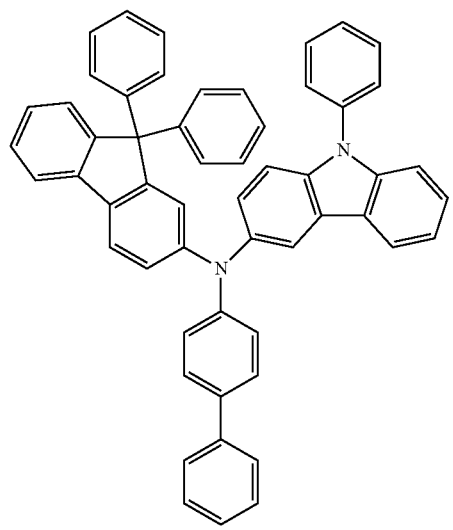
59
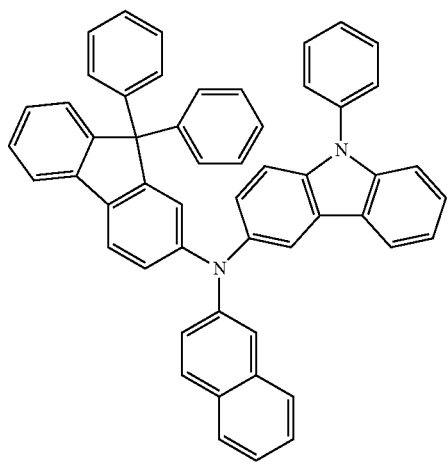
60
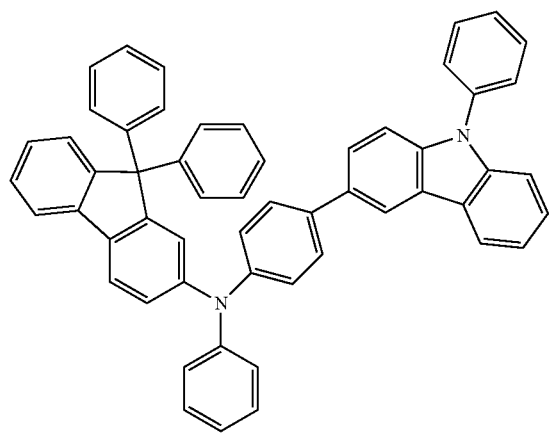
61
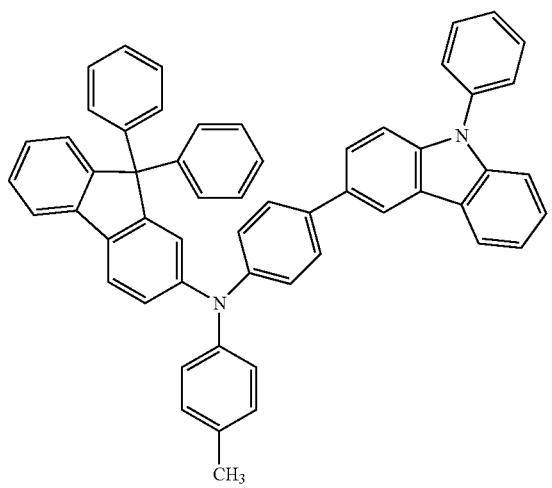

-continued

62

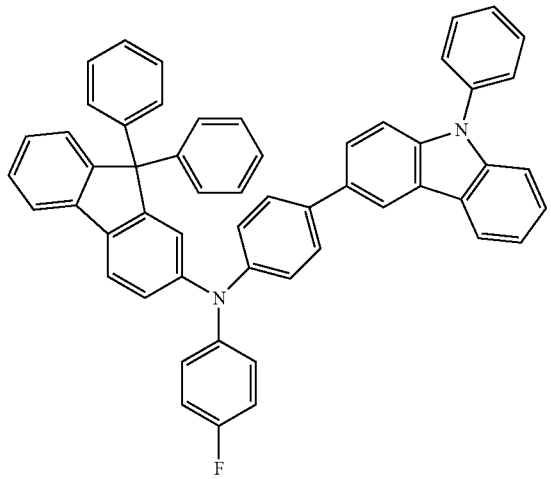

63

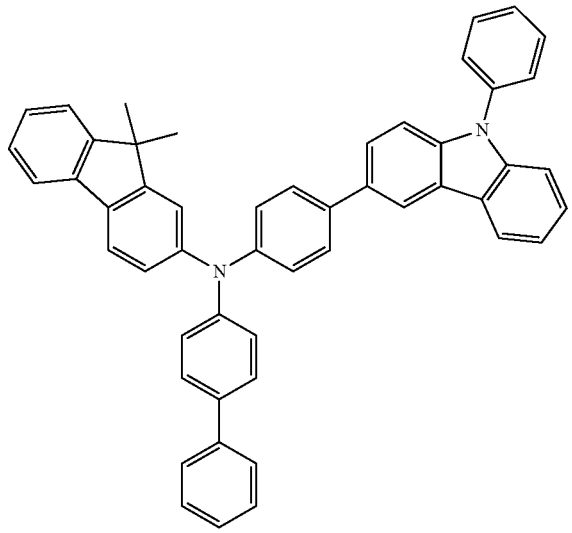

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and above all, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70% by mass to 100% by mass, and more preferably 85% by mass to 100% by mass, with respect to the total mass of the organic layer added.

With respect to the hole injecting layer and the hole transporting layer, the detailed descriptions in paragraph Nos. [0165] to [0167] of JP-A-2008-270736 can be applied to the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include tetracyanoquinodimethane (TCNQ) and TCNQ compounds such as tetrafluorotetracyanoquinodimethane ($F_4$-TCNQ), hexaazatriphenylene compounds such as hexacyano-hexaazatriphenylene (HAT-CN), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer (A-2) Electron Blocking Layer The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (1), a compound represented by the following general formula (P-1), and a compound represented by the following general formula (O-1).

Hereinafter, a compound represented by the general formula (O-1) and a compound represented by the general formula (P-1) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 48]

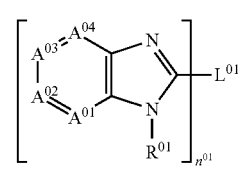

General formula (O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'S may be the same as or different from each other. $L^{O1}$ represents any of divalent to hexavalent linking groups with an aryl ring or a heteroaryl ring, $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 members out of $A^{O1}$ to $A^{O4}$ be nitrogen atoms; and it is more preferable that 0 or 1 member out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ are C—$R^A$; it is more preferable that $A^{O1}$ be a nitrogen atom, and $A^{O2}$ to $A^{O4}$ be C—$R^A$; it is still more preferable that $A^{O1}$ be a nitrogen atom, $A^{O2}$ to $A^{O4}$ be C—$R^A$, and $R^A$'s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents any of a divalent to hexavalent linking group including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 49]

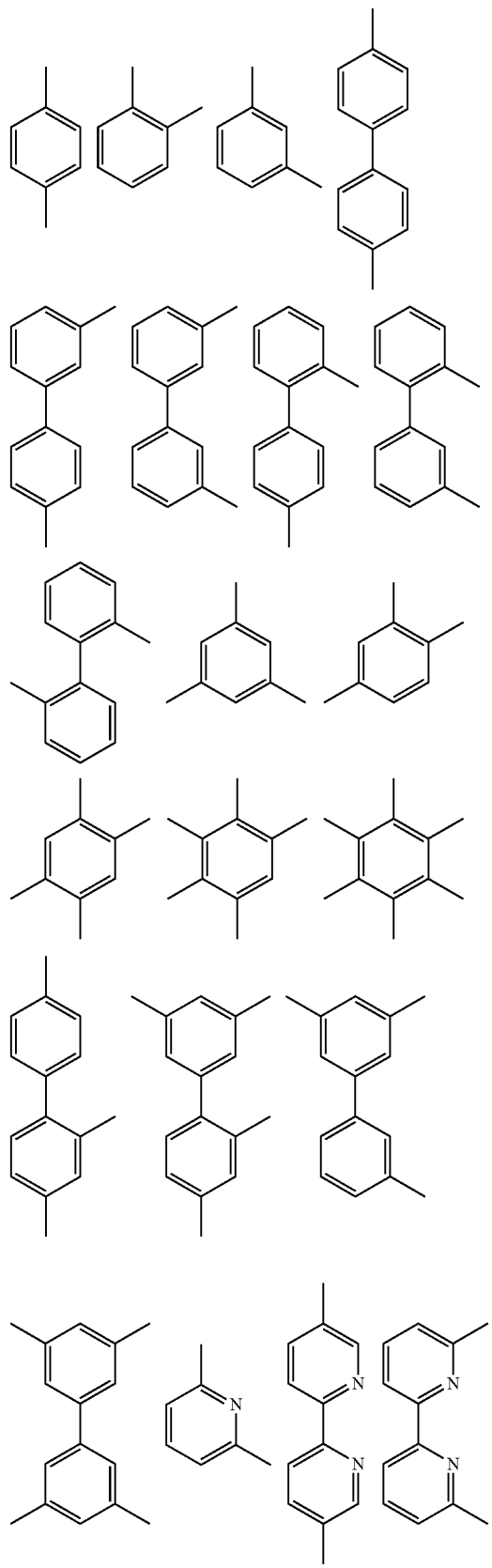

-continued

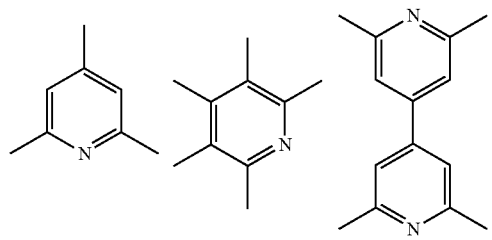

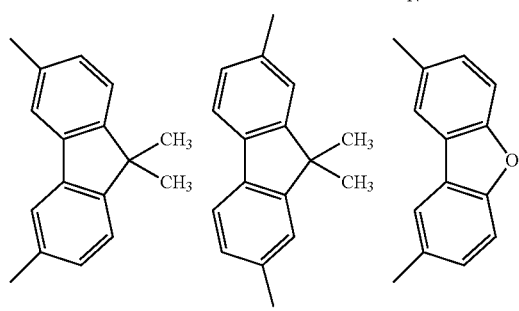

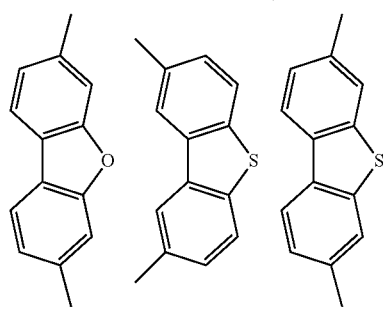

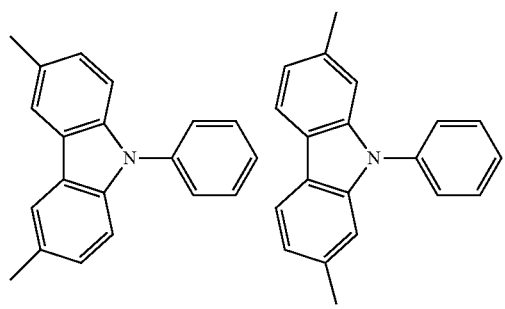

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 50]

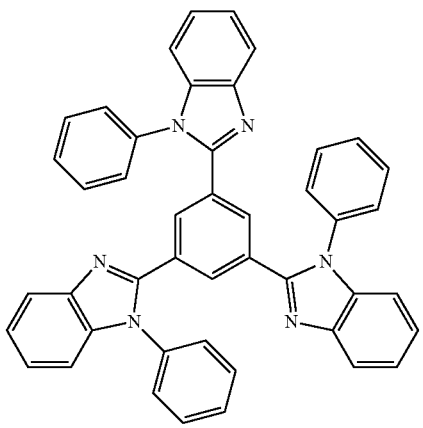

OM-1

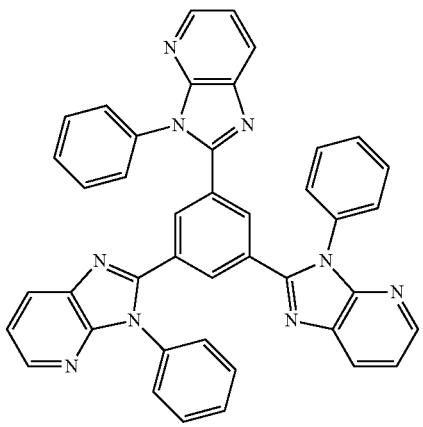

OM-2

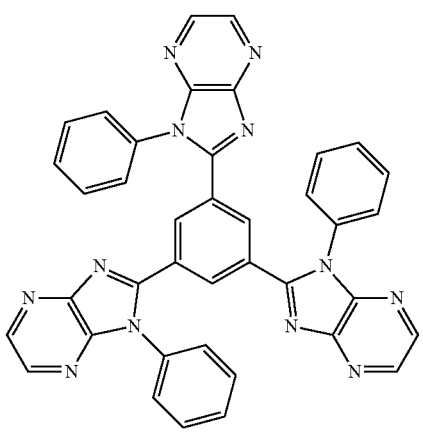

OM-3

OM-4
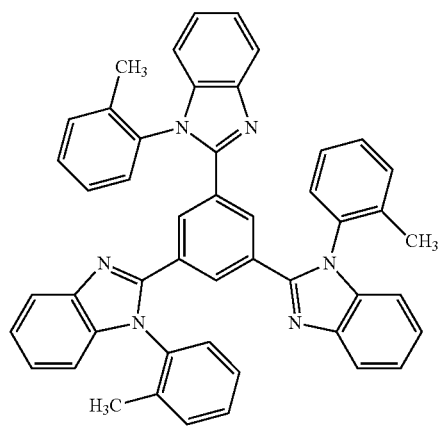
OM-5
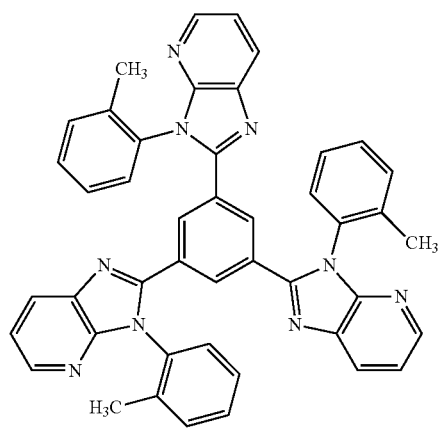
OM-6
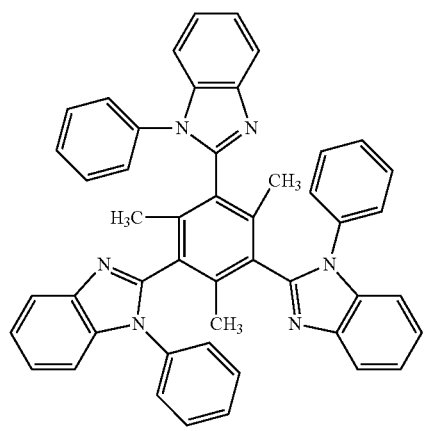
OM-7
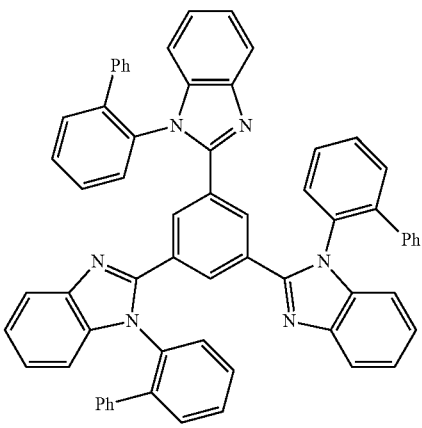
OM-8
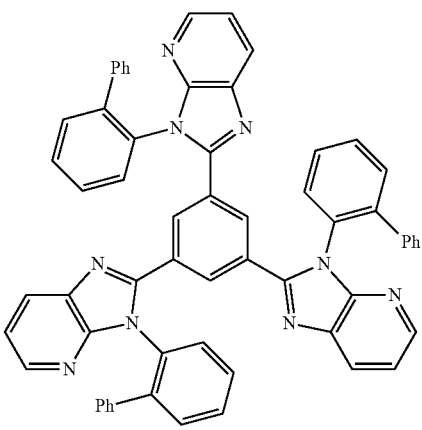
OM-9
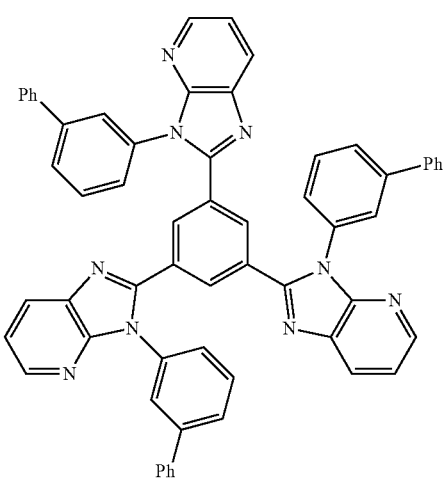

OM-10
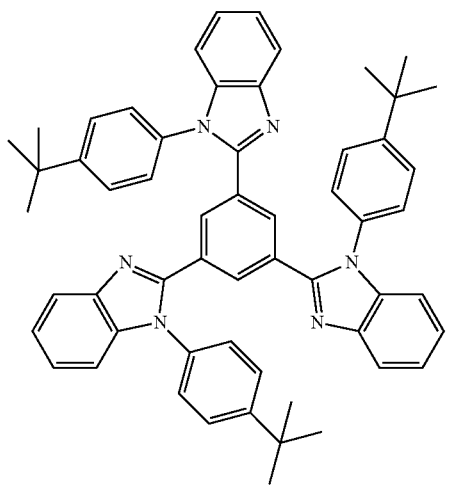
OM-11
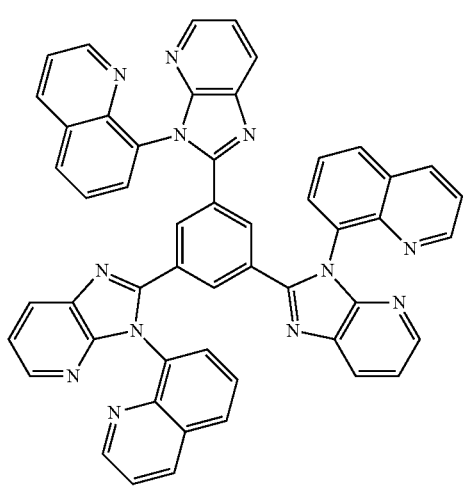
OM-12
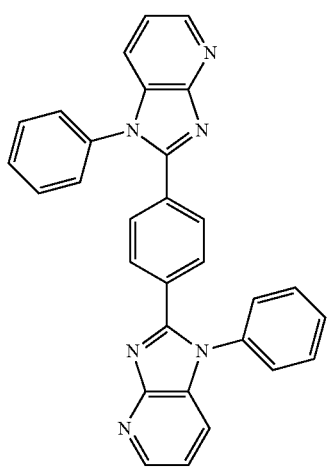
OM-13
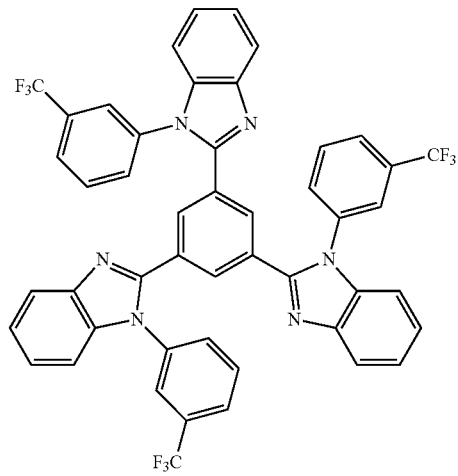
OM-14
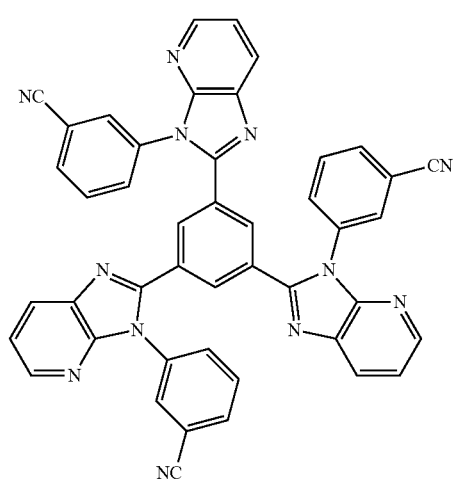
OM-15
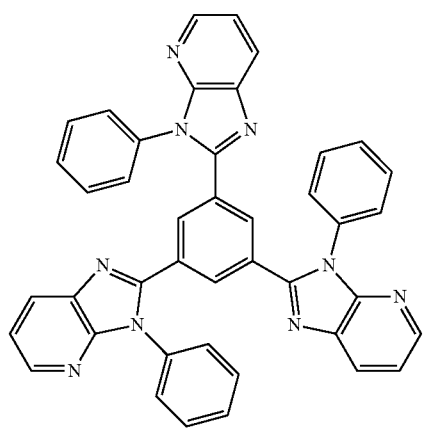

OM-16

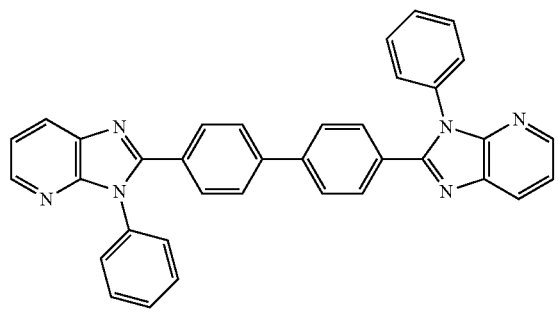

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70% by mass to 100% by mass, and more preferably 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

[Chem. 52]

General formula (P)

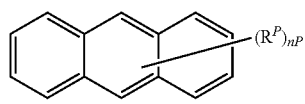

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in the case where there are a plurality of $R^P$'s, these may be the same as or different from each other. At least one of $R^P$'s is a substituent represented by the following general formulae (P-1) to (P-3).

[Chem. 53]

General formula (P-1)

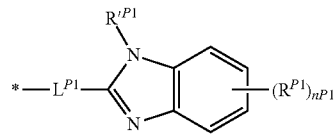

General formula (P-2)

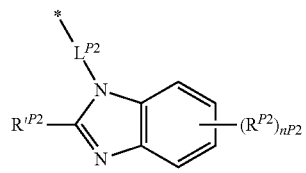

General formula (P-3)

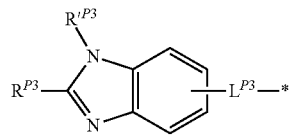

(In the general formulae (P-1) to (P-3), $R^{P1}$ to $R^{P3}$ and $R^{\prime P1}$ to $R^{\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in the case where there are a plurality of $R^{P1}$ to $R^{P3}$ and $R^{\prime P1}$ to $R^{\prime P3}$, these may be the same as or different from each other. $L^{P1}$ to $L^P3$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R^{\prime P1}$ to $R^{\prime P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 54]
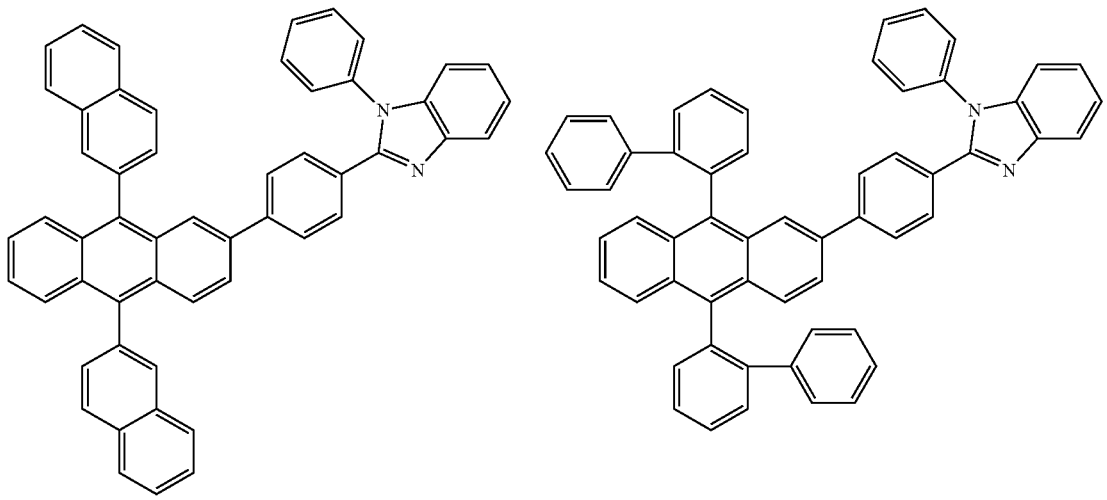
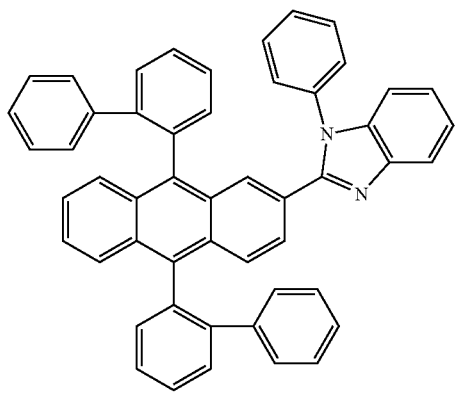
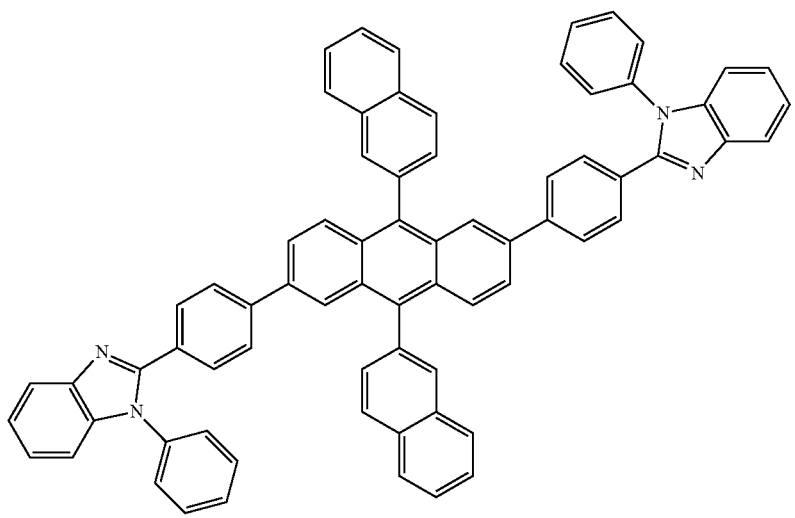

-continued
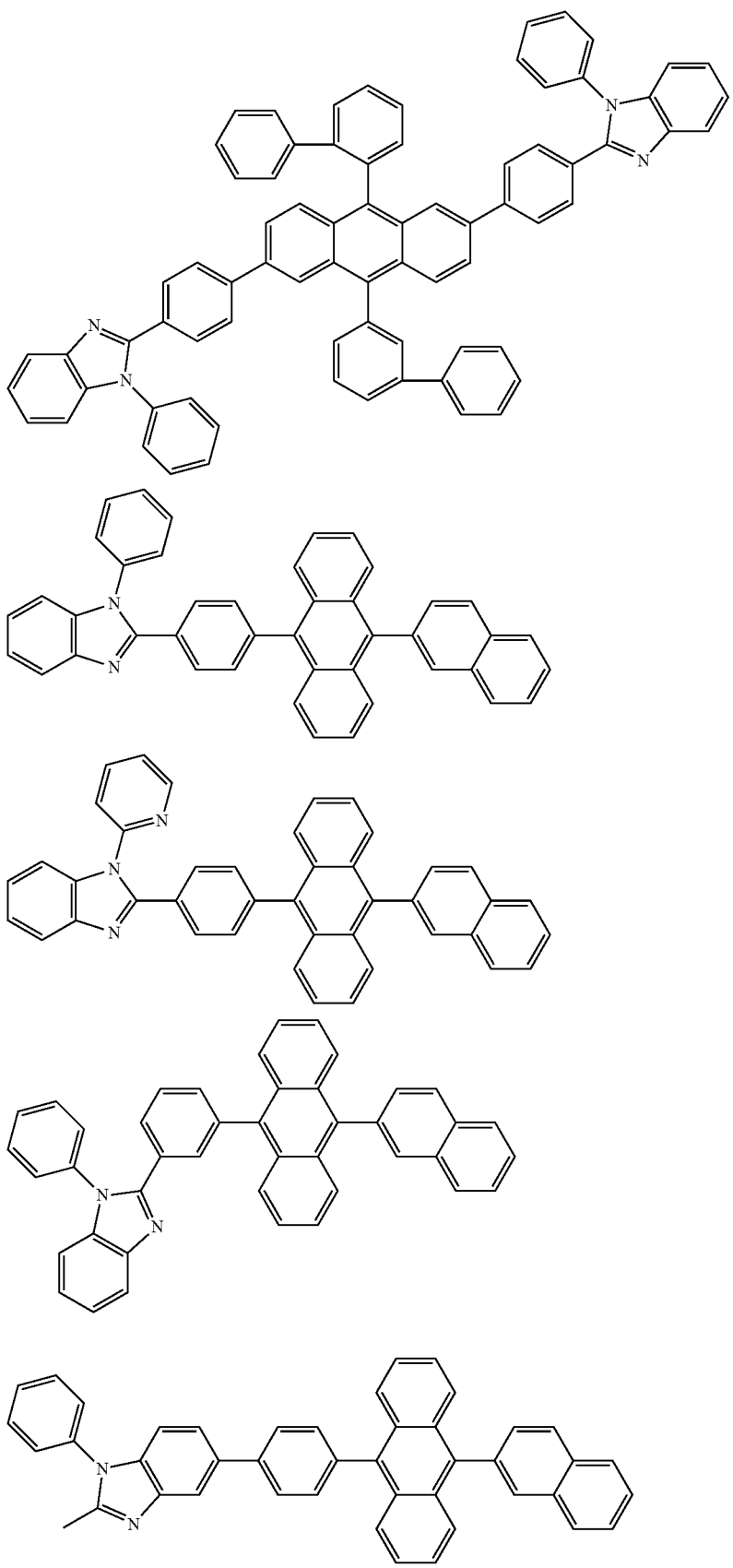

[Chem. 55]

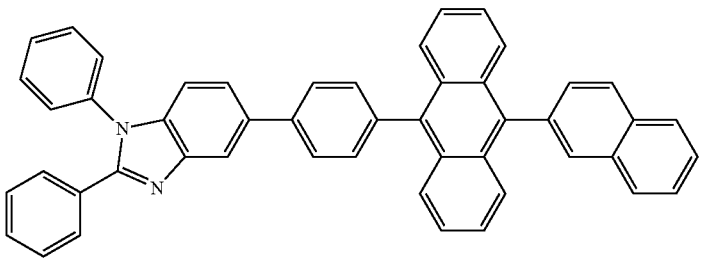

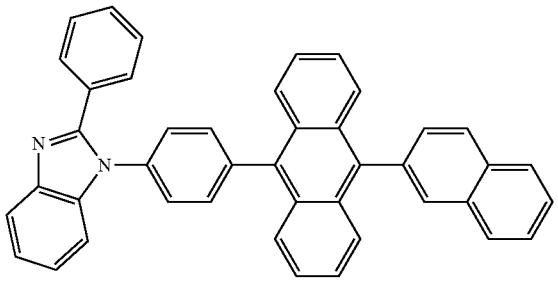

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70% by mass to 100% by mass, and more preferably 85% by mass to 100% by mass, based on the total mass of the organic layer added.

<Protective Layer>

In the present invention, the entirety of the organic electroluminescent element may be protected by a protective layer.

For the protective layer, the detailed description in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of from 300 cd/m$^2$ to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is not limited, but is preferably used for blue or white light emission. Above all, in the organic electroluminescent element of the present invention, the compound represented by the general formula (1) is preferably used as a light emitting material to emit light, and particularly preferably to emit blue light.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
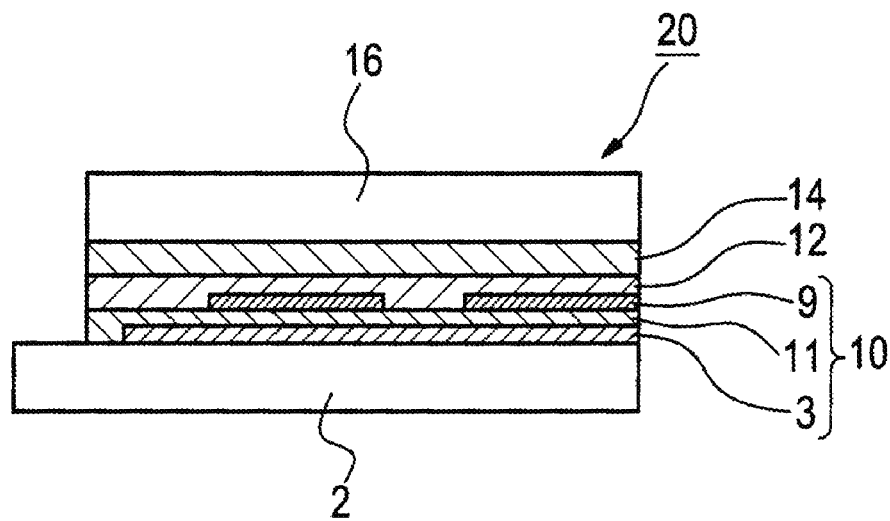
FIG. 2 is a schematic view showing one example of the light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
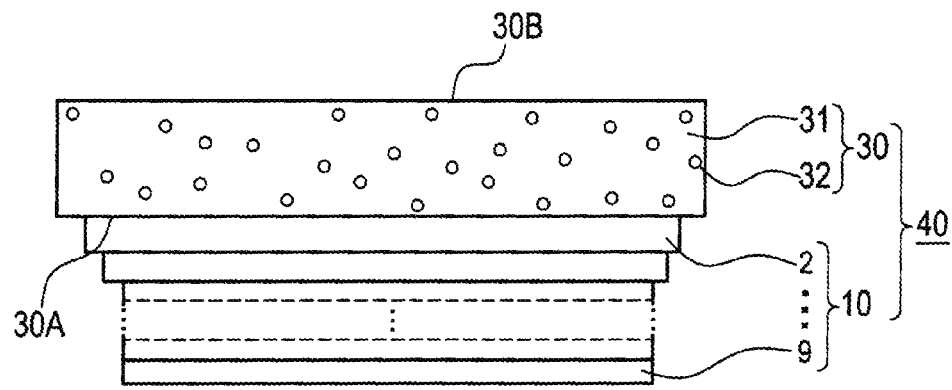
FIG. 3 is a schematic view showing one example of the illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

1. Synthesis Example

The compound represented by the general formula (1) can be synthesized by the method described in the present specification or a combination of other known reactions. Representative examples of the specific synthesis procedure of the compound represented by the general formula (1) will be described below. Further, other compounds represented by the general formula (1) used in each of Examples can also be synthesized by similar methods.

Synthesis of Compound 2

According to the following scheme, a compound 2 was synthesized.

[Chem. 56]

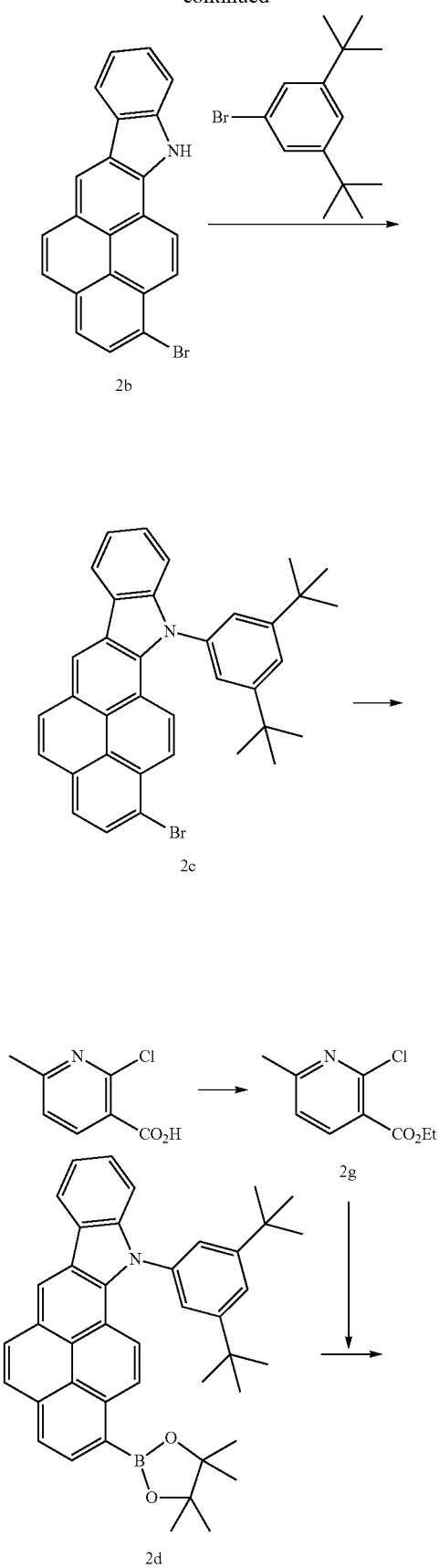

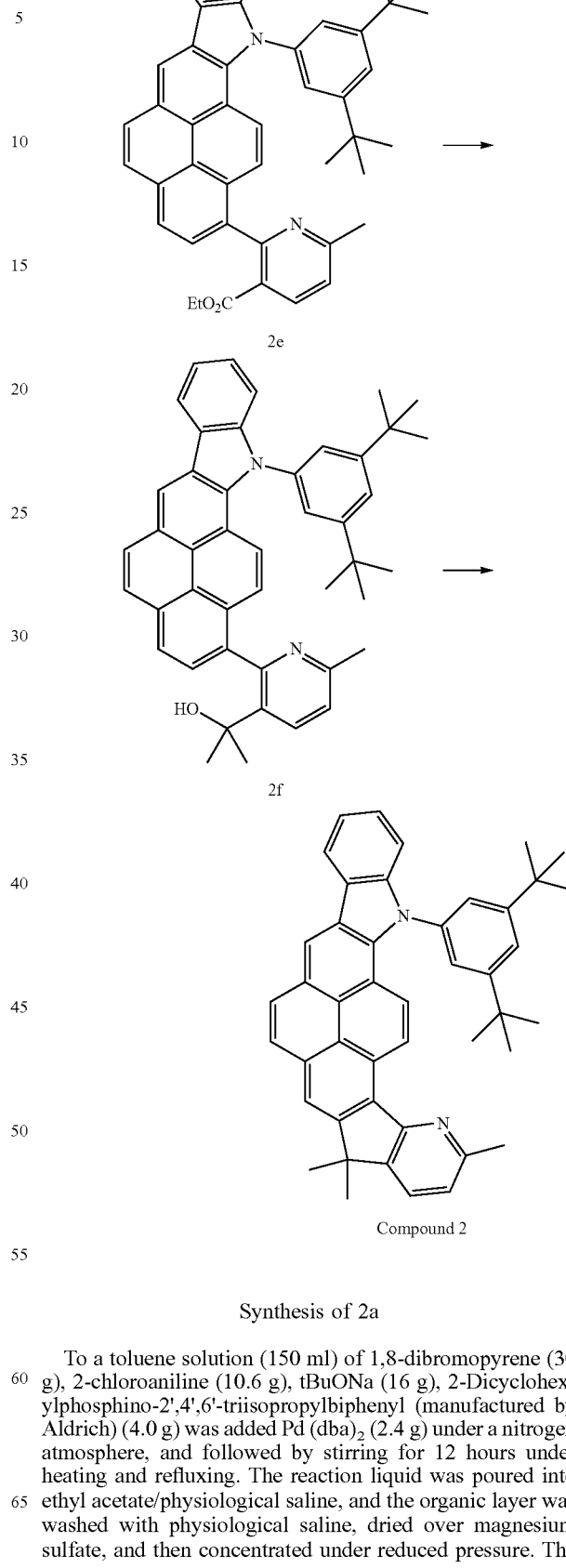

Compound 2

Synthesis of 2a

To a toluene solution (150 ml) of 1,8-dibromopyrene (30 g), 2-chloroaniline (10.6 g), tBuONa (16 g), 2-Dicyclohexylphosphino-2',4',6'-triisopropylbiphenyl (manufactured by Aldrich) (4.0 g) was added Pd (dba)$_2$ (2.4 g) under a nitrogen atmosphere, and followed by stirring for 12 hours under heating and refluxing. The reaction liquid was poured into ethyl acetate/physiological saline, and the organic layer was washed with physiological saline, dried over magnesium sulfate, and then concentrated under reduced pressure. The concentrated residue was purified by silica gel column chromatography to obtain a compound 2a (10.2 g).

Synthesis of 2b

To a DMAc solution (100 ml) of the compound 2a (10 g), tricyclohexyl phosphine (0.7 g), and potassium carbonate (g)) was added Pd(OAc)$_2$ (0.3 g) under a nitrogen atmosphere, followed by stirring for 18 hours under heating and refluxing. The obtained crude crystal was purified by silica gel column chromatography to obtain a compound 2b (5.5 g).

Synthesis of 2c

To a xylene solution (100 ml) of the compound 2b (5.4 g), tBuONa (4.2 g), 1,3-di-tertiary butylbromobenzene (manufactured by Tokyo Chemical Industry Co., Ltd.) (11.8 g), and tri-tertiary butylphosphine (0.3 g) was added Pd(dba)$_2$ (0.4 g) under a nitrogen atmosphere, followed by stirring for 5 hours under heating and refluxing. The reaction liquid was poured into ethyl acetate/physiological saline, and the organic layer was washed with physiological saline, dried over magnesium sulfate, and then concentrated under reduced pressure. The concentrated residue was purified by silica gel column chromatography to obtain a compound 2c (6.1 g).

Synthesis of 2d

A toluene solution (300 ml) of the compound 2c (6.0 g), bispinacolatoboran (manufactured by Wako Pure Chemical Industries, Ltd. (3.3 g), PdCl$_2$(dppf)$_2$·CH$_2$Cl$_2$ (0.26 g), and potassium acetate (2.6 g) was stirred for 12 hours under heating and refluxing under a nitrogen atmosphere. The reaction liquid was poured into ethyl acetate/physiological saline, and the organic layer was washed with physiological saline, dried over magnesium sulfate, and then concentrated under reduced pressure. The concentrated residue was purified by silica gel column chromatography to obtain a compound 2d (5.4 g).

Synthesis of 2 g

An acetonitrile solution (100 ml) of 2-chloro-6-methyl nicotinic acid (10 g), iodine ethane (5 equivalents), and cesium carbonate (1.5 equivalents) was stirred for 6 hours under heating and refluxing. The reaction liquid was filtered, and the inorganic salts were removed and then concentrated under reduced pressure. The concentrate was dissolved in chloroform and washed with aqueous sodium bicarbonate, and the organic layer was dried over magnesium sulfate and then concentrated under reduced pressure to obtain a compound 2g (9.7 g).

Synthesis of 2e

The compound 2d (5.2 g), the compound 2g (1.9 g), tris(dibenzylidenacetone) dipalladium (Pd$_2$ (dba) 3) (0.4 mg), 2-dicyclohexylphosphino-2',6'-dimethoxybiphenyl (SPhos) (0.35 mg), and potassium phosphate (3.6 g) were mixed, and heated and refluxed for 8 hours under a nitrogen atmosphere. The reaction liquid was returned to room temperature, then ethyl acetate and pure water were added thereto, and the organic layer was extracted. The organic layer was dried over sodium sulfate, concentrated under reduced pressure, and purified by silica gel column chromatography to obtain a compound 2e (4.7 g).

Synthesis of 2f

A THF solution (50 ml) of the compound 2e (4.5 g) was allowed to undergo a reaction with 3 equivalents of a methyl Grignard reagent at −78° C., thereby performing a reaction. The reaction liquid was poured into ethyl acetate/physiological saline, and the organic layer was washed with physiological saline, dried over magnesium sulfate, and then concentrated under reduced pressure. The concentrated residue was purified by silica gel column chromatography to obtain a compound 2f (3.4 g).

Synthesis of Compound 2

A dichloromethane/methane sulfonic acid=1/1 solution (60 ml) of the compound 2f (3.2 g) was stirred for 2 hours under ice-cooling. The reaction liquid was poured into ice water and further neutralized with an aqueous sodium hydroxide solution. Ethyl acetate was added thereto and the organic layer was extracted, washed with saturated physiological saline, and then dried over magnesium sulfate. After concentrating under reduced pressure, the concentrated residue was purified by silica gel column chromatography to obtain a compound 2 (1.46 g). Further, the obtained compound was identified by elemental analysis, NMR and MASS spectrum.

2. Evaluation of Physical Properties of Materials

Test Example (a) Light Emitting Wavelength

The following Host Compound H-1 and each of light emitting materials shown in Table 1 below were deposited on a 0.7 mm-thick and 25 mm square quartz glass substrate by a vacuum deposition method in a mass ratio (99/1), thereby forming a thin film having a film thickness of 50 nm and depositing 100 nm of aluminum thereon. The obtained film was irradiated with UV rays of 350 nm to emit light. The luminous spectrum at that time was measured using a fluorescent spectrophotometer (FP-6300, manufactured by JASCO Corporation), and the maximum light emitting wavelength was evaluated as the following 3 grades according to the following criteria.

A: 440 nm or more and less than 455 nm.
B: 430 nm or more and less than 440 nm, and 455 nm or more and less than 465 nm.
C: Less than 430 nm and 465 nm or more.

[Chem. 57]

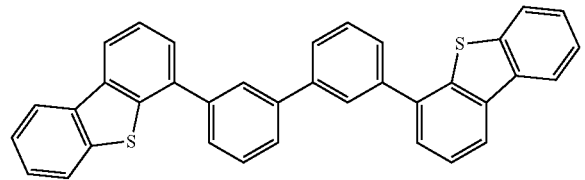

(Host compound H-1)

(b) Spectrum Half-Value Width

The spectrum half-value width FWHM (1%) (conversion in terms of energy) in the luminous spectrum, measured with the (a) light emitting wavelength, was evaluated as the following 3 grades according to the following criteria.

A: Less than 0.20 eV.

B: 0.20 eV or more and less than 0.25 eV.

C: 0.25 eV or more.

(c) Inhibition of Association Sub-Light Emission

In the film fabricated in the same manner as for the measurement of the (a) light emitting wavelength except for the mass ratio of the host compound H-1 to each of the light emitting materials described in Table 1 below was changed to 93:7, the spectrum half-value width %, FWHM (7%) was measured in the same manner as for the measurement of the (b) spectrum half-value width. The spectrum half-value width ratio (FWHM (7%)/FWHM (1%)) of a 7% doped film of each light emitting material to a 1% doped film measured by the measurement of the (b) spectrum half-value width was evaluated as the following 3 grades according to the following criteria.

A: Less than 1.1.

B: 1.1 or more and less than 1.2.

C: 1.2 or more.

(d) Deposition Suitability

Using 20 mg of each compound described as a light emitting material in Table 1 below, vacuum TG/DTA measurement (a temperature elevating speed of 2° C./min and a vacuum degree of about $10^{-2}$ Pa) was carried out, and the 10%-by-mass reduction temperature was evaluated as the following 2 grades.

A: Lower than 300° C.

C: 300° C. or higher.

The comparative compounds 1 to 4 used as a comparative light emitting material in Table 1 below have the following structures.

[Chem. 58]

(Comparative light emitting material)

Comparative compound 1

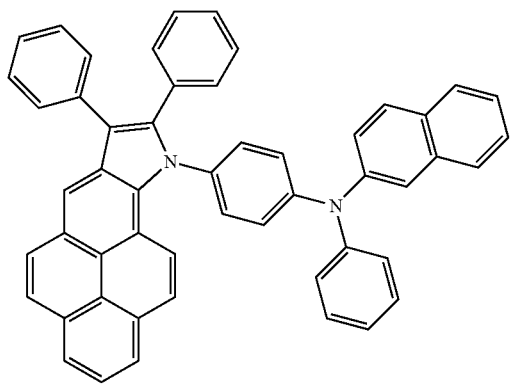

Compound described in JP-A-2011-51969

Comparative compound 2

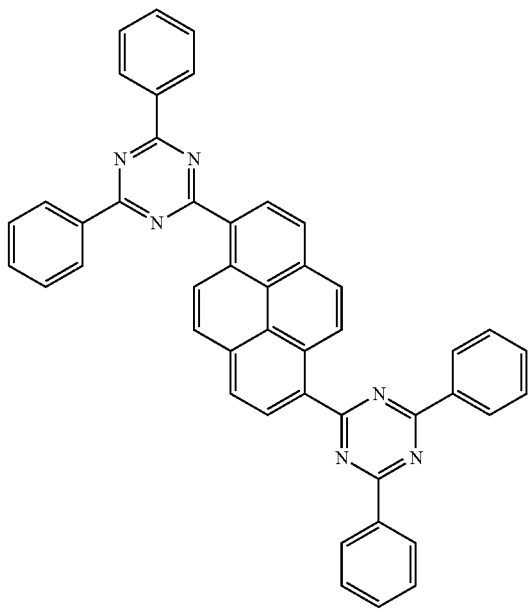

Compound described in JP-A-2010-18121

Comparative compound 3

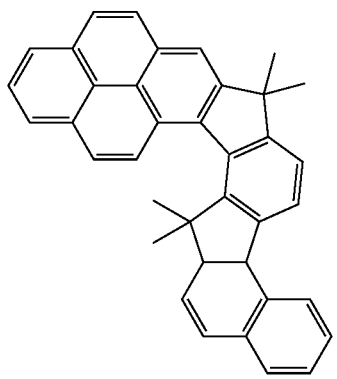

Compound 2 described in DE102008035413

Comparative compound 4

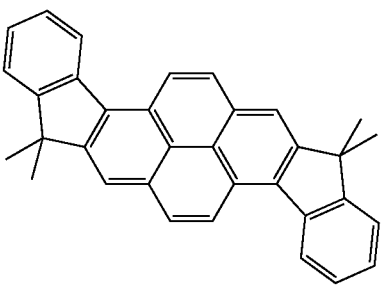

Compound 81 described in DE102008035413

The test results for the physical properties of each of the light emitting materials obtained in (a) to (d) above are described in Table 1 below.

TABLE 1

| Light emitting material | Light emitting wavelengt | spectrum half-value width | Inhibition of association sub-light emission | Deposition suitability | Note |
|---|---|---|---|---|---|
| Compound 1 | A | A | A | A | The present invention |
| Compound 2 | A | A | A | A | The present invention |
| Compound 3 | A | A | A | A | The present invention |
| Compound 4 | A | A | A | A | The present invention |
| Compound 5 | A | A | A | A | The present invention |
| Compound 6 | A | A | A | A | The present invention |
| Compound 7 | A | A | A | A | The present invention |
| Compound 8 | A | A | A | A | The present invention |
| Compound 9 | A | A | A | A | The present invention |
| Compound 10 | A | A | A | A | The present invention |
| Compound 11 | A | A | A | A | The present invention |
| Compound 12 | A | A | A | A | The present invention |
| Compound 13 | A | A | A | C | The present invention |
| Compound 14 | A | A | A | A | The present invention |
| Compound 15 | A | A | A | A | The present invention |
| Compound 16 | A | A | B | A | The present invention |
| Compound 17 | A | A | A | A | The present invention |
| Compound 18 | B | A | A | A | The present invention |
| Compound 19 | A | A | A | A | The present invention |
| Compound 20 | A | A | A | A | The present invention |
| Compound 21 | A | A | A | A | The present invention |
| Compound 22 | B | A | A | A | The present invention |
| Compound 23 | A | A | A | A | The present invention |
| Compound 24 | A | A | A | A | The present invention |
| Compound 25 | B | A | A | A | The present invention |
| Compound 26 | A | A | A | A | The present invention |
| Compound 27 | B | A | A | A | The present invention |
| Comparative compound 1 | C | B | A | C | Comparative Example |
| Comparative compound 2 | C | C | B | A | Comparative Example |
| Comparative compound 3 | A | C | B | A | Comparative Example |
| Comparative compound 4 | B | B | C | C | Comparative Example |

3. Fabrication and Evaluation of Organic Electroluminescent Element

All of the materials used in the fabrication of the organic electroluminescent element were subjected to sublimation purification, and it was confirmed that the purity (absorption intensity area ratio at 254 nm) was 99.9% or more by using a high performance liquid chromatograph (TSKgel ODS-100Z, manufactured by Tosoh Corporation).

Example 1

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method.

Furthermore, the deposition rates in Examples and Comparative Examples below are 0.1 nm/sec unless otherwise indicated. The deposition rates were measured using a quartz crystal oscillator. Further, the thickness of each of the layers below was measured using a quartz crystal oscillator.

First layer: HAT-CN: Film thickness: 10 nm
Second layer: HT-2: Film thickness 30 nm
Third layer: H-1 and the light emitting material descried in Table 1 (mass ratio=93:7): Film thickness: 30 nm
Fourth layer: ET-1: Film thickness 30 nm 1 nm of lithium fluoride and 100 nm of metallic aluminum were deposited in this order thereon, thereby forming a cathode. At that time, a patterned mask (mask having a light emitting area of 2 mm×2 mm) was placed on the layer of lithium fluoride, and the metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-CIBA Ltd.), thereby obtaining organic electroluminescent elements 1-1 to 1-10, and comparative organic electroluminescent elements 1-1 to 1-4, each having a light emitting area in a 2 mm×2 mm square. Light emission due to the light emitting material was observed in each of the elements. For each of the obtained organic electroluminescent element, the tests below were carried out.

(a) External Quantum Efficiency

A direct current voltage was applied to each element by using a source measure unit 2400 (Keithley Instruments Inc.) to allow the organic electroluminescent element to emit light. The luminance was measured with a luminance meter (BM-8, manufactured by Topcon Corporation). The luminous spectrum and the light emitting wavelength were measured with a spectrum analyzer (PMA-11, Hamamatsu Photonics K. K.). Based on these values, the external quantum efficiency (η) at a luminance in the vicinity of 1,000 cd/m$^2$ was calculated by using a luminance conversion method, and shown as a relative value, taking the value of the organic electroluminescent element using the comparative compound 3 as 1.0. Larger numeral values are preferable, because larger values indicate better efficiency.

(b) Chromaticity

The chromaticity (x, y) was determined from the luminous spectrum when light was emitted at a luminance of 1,000 cd/m$^2$ after a direct current voltage was applied to each of the organic electroluminescent elements. From the y values at the time, the chromaticity was evaluated as the following 4 grades.

A: 0.05≤y≤0.10.
B: 0.04≤y<0.05, 0.10<y≤0.15.
C: 0.03≤y<0.04, 0.15≤y≤0.20.
D: y<0.03, 0.20<y.

(c) Chromaticity after Deterioration by Driving

Light was emitted at a luminance of 1000 cd/m$^2$ after a direct current voltage was continuously applied to each of the organic electroluminescent elements, and the chromaticity (x', y') after the luminance decreased to 500 cd/m was measured from the luminous spectrum. The change in chromaticity after deterioration by driving was evaluated as the following 3 grades, from changes in y values Δy (=|y'−Δy|) before and after the deterioration by driving.

A: Δy≤0.01.
B: 0.01<Δy≤0.02.
C: 0.02<Δy.

TABLE 2

| Element No. | Light emitting material | Relative external quantum efficiency | Chromaticity | Chromaticity after deterioration by driving | Note |
|---|---|---|---|---|---|
| Element 1-1 | Compound 1 | 5.2 | A | B | The present invention |
| Element 1-2 | Compound 2 | 5.1 | A | B | The present invention |
| Element 1-3 | Compound 3 | 5.1 | A | B | The present invention |
| Element 1-4 | Compound 9 | 4.9 | A | B | The present invention |
| Element 1-5 | Compound 13 | 4.8 | A | B | The present invention |
| Element 1-6 | Compound 14 | 5.3 | A | B | The present invention |
| Element 1-7 | Compound 15 | 3.4 | A | B | The present invention |
| Element 1-8 | Compound 17 | 4.7 | A | B | The present invention |
| Element 1-9 | Compound 18 | 3.6 | A | B | The present invention |
| Element 1-10 | Compound 20 | 3.1 | A | B | The present invention |
| Comparative element 1-1 | Comparative compound 1 | 0.3 | D | D | Comparative Example |
| Comparative element 1-2 | Comparative compound 2 | 0.5 | D | D | Comparative Example |
| Comparative element 1-3 | Comparative compound 3 | 1.0 | D | D | Comparative Example |
| Comparative element 1-4 | Comparative compound 4 | 0.1 | D | D | Comparative Example |

Example 2

Organic electroluminescent elements were fabricated in the same manner as in Example 1, except that the layer configurations were changed as follows, and evaluations were carried out in the same manner as in Example 1. The results are shown in Table 3 below. Further, the external quantum efficiency shown in Table 3 is shown as a relative value, taking the external quantum efficiency of the organic electroluminescent element using the comparative compound 3 as 1.0.

First layer: HT-4: Film thickness 50 nm

Second layer: HT-3: Film thickness 45 nm

Third layer: H-2 and the light emitting material descried in Table 3 (mass ratio=95:5): Film thickness: 25 nm Fourth layer: ET-5: Film thickness 5 nm Fifth layer: ET-3: Film thickness 20 nm

TABLE 3

| Element No. | Light emitting material | Relative external quantum efficiency | Chromaticity | Chromaticity after deterioration by driving | Note |
|---|---|---|---|---|---|
| Element 2-1 | Compound 1 | 1.3 | A | B | The present invention |
| Element 2-2 | Compound 2 | 1.3 | A | B | The present invention |
| Element 2-3 | Compound 3 | 1.3 | A | B | The present invention |
| Element 2-4 | Compound 9 | 1.3 | A | B | The present invention |
| Element 2-5 | Compound 13 | 1.3 | A | B | The present invention |
| Element 2-6 | Compound 14 | 1.3 | A | B | The present invention |
| Element 2-7 | Compound 15 | 1.2 | A | B | The present invention |
| Element 2-8 | Compound 17 | 1.3 | A | B | The present invention |
| Element 2-9 | Compound 18 | 1.2 | A | B | The present invention |
| Element 2-10 | Compound 20 | 1.2 | A | B | The present invention |
| Comparative element 2-1 | Comparative compound 1 | 0.3 | D | D | Comparative Example |
| Comparative element 2-2 | Comparative compound 2 | 0.1 | D | D | Comparative Example |
| Comparative element 2-3 | Comparative compound 3 | 1.0 | C | D | Comparative Example |
| Comparative element 2-4 | Comparative compound 4 | 1.1 | B | D | Comparative Example |

Example 3

Organic electroluminescent elements were fabricated in the same manner as in Example 1, except that the layer configurations were changed as follows, and evaluations were carried out in the same manner as in Example 1. The results are shown in Table 4 below. Further, the external quantum efficiency shown in Table 4 is shown as a relative value, taking the external quantum efficiency of the organic electroluminescent element using the comparative compound 3 as 1.0.

First layer: HAT-CN: Film thickness 10 nm
Second layer: HT-2: Film thickness 30 nm
Third layer: H-1 and the light emitting material descried in Table 4 (mass ratio=95:5): Film thickness: 30 nm
Fourth layer: ET-4: Film thickness 30 nm

TABLE 4

| Element No. | Light emitting material | Relative external quantum efficiency | Chromaticity | Chromaticity after deterioration by driving | Note |
|---|---|---|---|---|---|
| Element 3-1 | Compound 1 | 1.4 | A | B | The present invention |
| Element 3-2 | Compound 2 | 1.3 | A | B | The present invention |
| Element 3-3 | Compound 3 | 1.4 | A | B | The present invention |
| Element 3-4 | Compound 9 | 1.3 | A | B | The present invention |
| Element 3-5 | Compound 13 | 1.3 | A | B | The present invention |
| Element 3-6 | Compound 14 | 1.3 | A | B | The present invention |
| Element 3-7 | Compound 15 | 1.2 | A | B | The present invention |
| Element 3-8 | Compound 17 | 1.3 | A | B | The present invention |
| Element 3-9 | Compound 18 | 1.2 | A | B | The present invention |
| Element 3-10 | Compound 20 | 1.2 | A | B | The present invention |
| Comparative element 3-1 | Comparative compound 1 | 0.3 | D | D | Comparative Example |
| Comparative element 3-2 | Comparative compound 2 | 0.6 | D | D | Comparative Example |

TABLE 4-continued

| Element No. | Light emitting material | Relative external quantum efficiency | Chromaticity | Chromaticity after deterioration by driving | Note |
|---|---|---|---|---|---|
| Comparative element 3-3 | Comparative compound 3 | 1.0 | C | D | Comparative Example |
| Comparative element 3-4 | Comparative compound 4 | 1.1 | B | D | Comparative Example |

Example 4

Organic electroluminescent elements were fabricated in the same manner as in Example 1, except that the layer configurations were changed as follows, and evaluations were carried out in the same manner as in Example 1. The results are shown in Table 5 below. Further, the external quantum efficiency shown in Table 5 is shown as a relative value, taking the external quantum efficiency of the organic electroluminescent element using the comparative compound 3 as 1.0.

First layer: HAT-CN: Film thickness 10 nm
Second layer: HT-1: Film thickness 30 nm
Third layer: H-3 and the light emitting material descried in Table 5 (mass ratio=93:7): Film thickness: 30 nm
Fourth layer: ET-4: Film thickness 30 nm

Example 5

Organic electroluminescent elements were fabricated in the same manner as in Example 1, except that the layer configurations were changed as follows, and evaluations were carried out in the same manner as in Example 1. The results are shown in Table 6 below. Further, the external quantum efficiency shown in Table 6 is shown as a relative value, taking the external quantum efficiency of the organic electroluminescent element using the comparative compound 3 as 1.0.

First layer: HAT-CN: Film thickness 10 nm
Second layer: HT-2: Film thickness 30 nm
Third layer: H-4 and the light emitting material descried in Table 6 (mass ratio=93:7): Film thickness: 30 nm
Fourth layer: ET-2: Film thickness 30 nm

TABLE 5

| Element No. | Light emitting material | Relative external quantum efficiency | Chromaticity | Chromaticity after deterioration by driving | Note |
|---|---|---|---|---|---|
| Element 4-1 | Compound 1 | 1.3 | A | B | The present invention |
| Element 4-2 | Compound 2 | 1.3 | A | B | The present invention |
| Element 4-3 | Compound 3 | 1.4 | A | B | The present invention |
| Element 4-4 | Compound 9 | 1.3 | A | B | The present invention |
| Element 4-5 | Compound 13 | 1.2 | A | B | The present invention |
| Element 4-6 | Compound 14 | 1.3 | A | B | The present invention |
| Element 4-7 | Compound 15 | 1.2 | A | B | The present invention |
| Element 4-8 | Compound 17 | 1.3 | A | B | The present invention |
| Element 4-9 | Compound 18 | 1.2 | A | B | The present invention |
| Element 4-10 | Compound 20 | 1.2 | A | B | The present invention |
| Comparative element 4-1 | Comparative compound 1 | 0.5 | C | D | Comparative Example |
| Comparative element 4-2 | Comparative compound 2 | 0.7 | C | D | Comparative Example |
| Comparative element 4-3 | Comparative compound 3 | 1.0 | C | D | Comparative Example |
| Comparative element 4-4 | Comparative compound 4 | 0.9 | B | D | Comparative Example |

TABLE 6

| Element No. | Light emitting material | Relative external quantum efficiency | Chromaticity | Chromaticity after deterioration by driving | Note |
|---|---|---|---|---|---|
| Element 5-1 | Compound 4 | 1.2 | A | B | The present invention |
| Element 5-2 | Compound 6 | 1.2 | A | B | The present invention |
| Element 5-3 | Compound 11 | 1.3 | A | B | The present invention |
| Element 5-4 | Compound 12 | 1.3 | A | B | The present invention |
| Element 5-5 | Compound 19 | 1.2 | A | B | The present invention |
| Element 5-6 | Compound 22 | 1.2 | A | B | The present invention |
| Element 5-7 | Compound 23 | 1.4 | A | B | The present invention |
| Element 5-8 | Compound 24 | 1.1 | A | B | The present invention |
| Element 5-9 | Compound 25 | 1.2 | A | B | The present invention |
| Element 5-10 | Compound 26 | 1.1 | A | B | The present invention |
| Comparative element 5-1 | Comparative compound 1 | 0.3 | C | D | Comparative Example |
| Comparative element 5-2 | Comparative compound 2 | 0.1 | C | D | Comparative Example |
| Comparative element 5-3 | Comparative compound 3 | 1.0 | C | D | Comparative Example |
| Comparative element 5-4 | Comparative compound 4 | 0.9 | B | D | Comparative Example |

[Chem. 59]

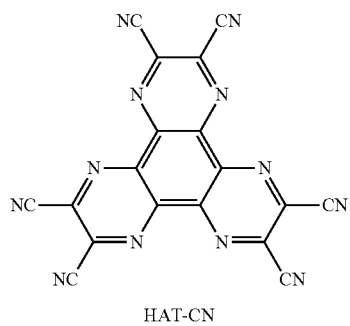

HAT-CN

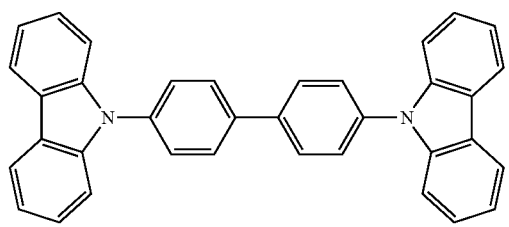

CBP

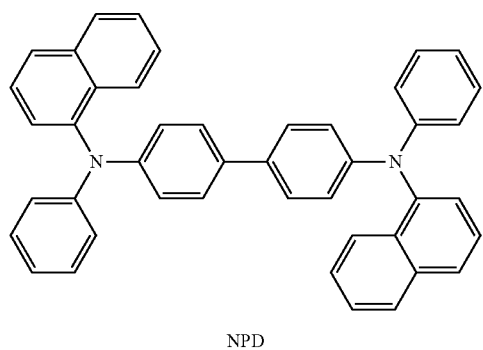

NPD

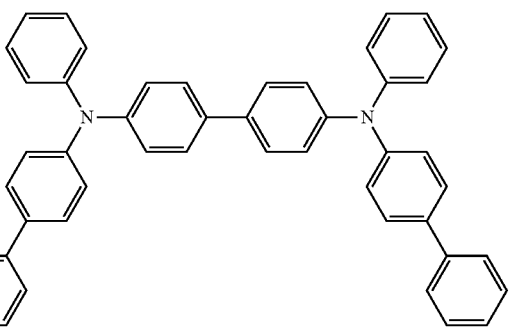

HT-1

-continued
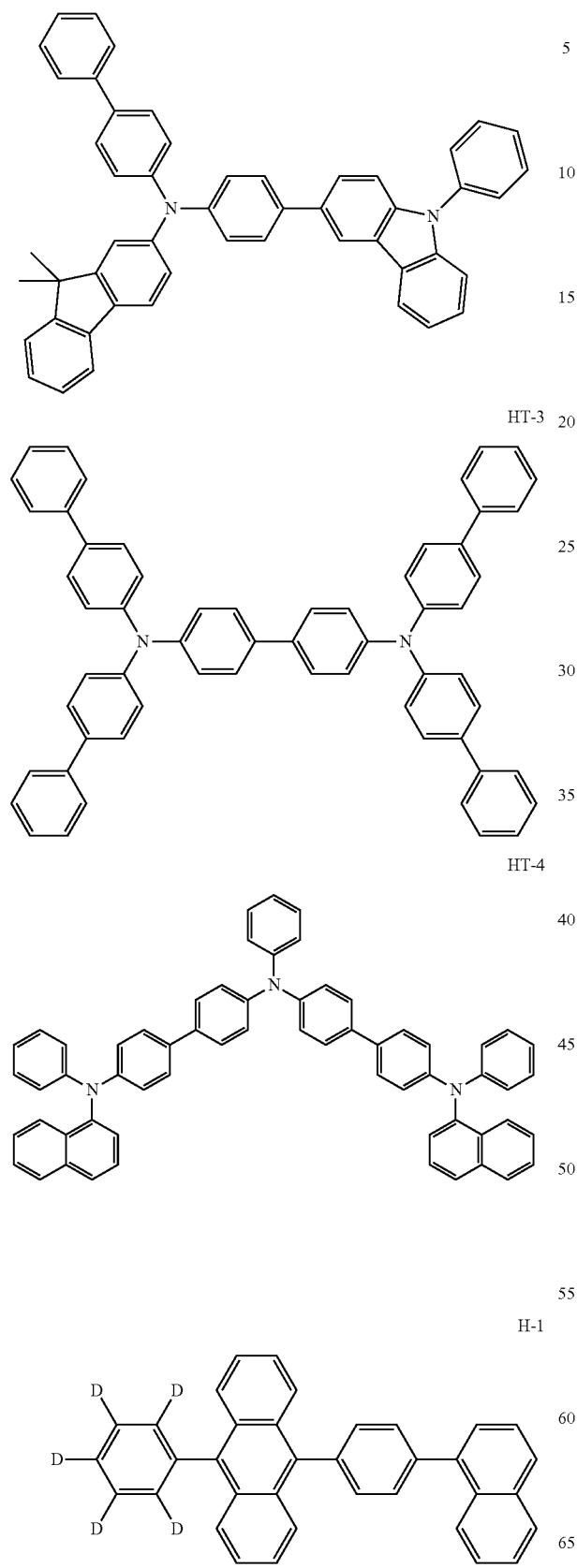
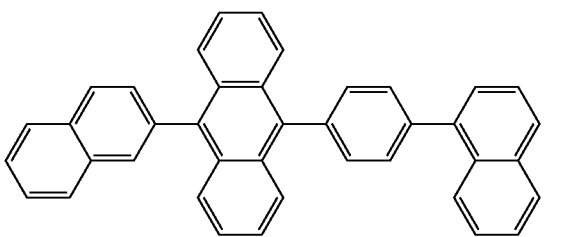
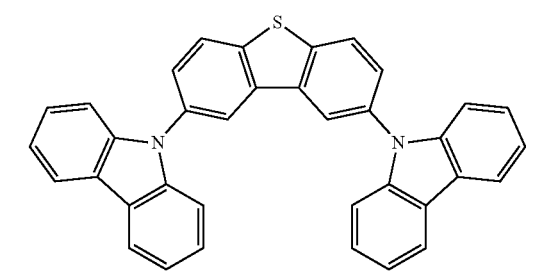
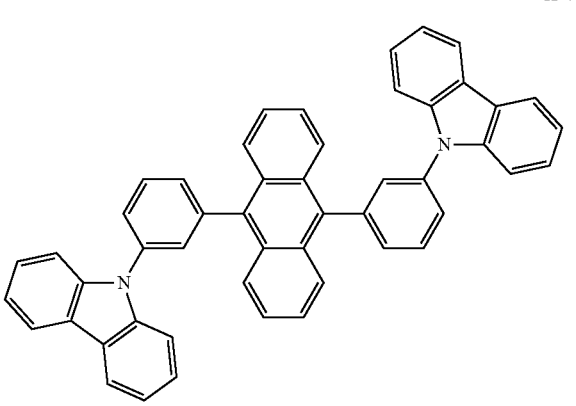

ET-2

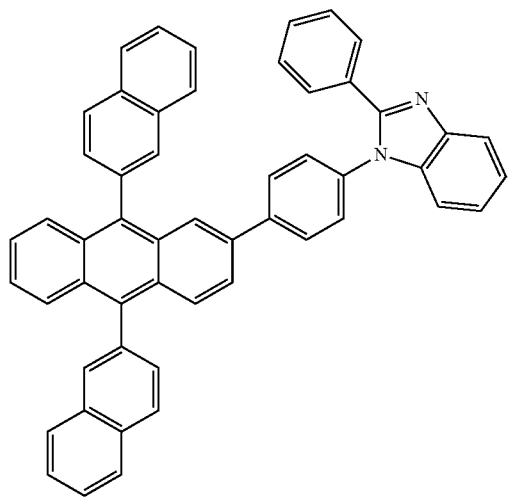

ET-3

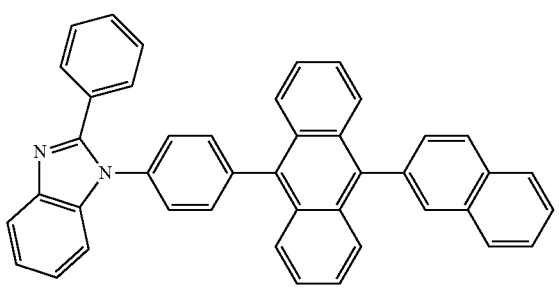

ET-4

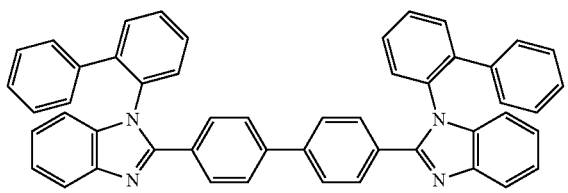

et-5

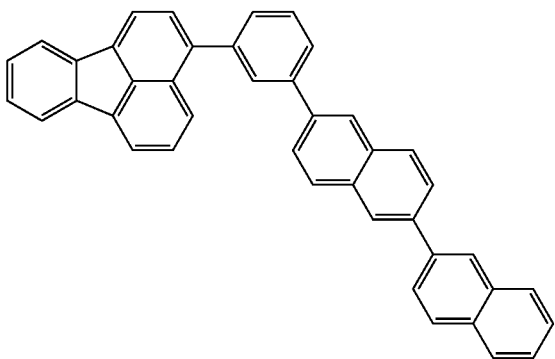

Example 6

Evaluation of Organic Electroluminescent Element (Coating)

—Preparation of Light Emitting Layer-Forming Coating Liquids—

The compound 2 as a light emitting material (0.1% by mass) and the following host material PH-1 (0.9% by mass) were mixed with methyl ethyl ketone (98.99% by mass) to obtain a light emitting layer-forming coating liquid 1.

Light emitting layer-forming coating liquids 2 and 3 were prepared in the same manner as for the light emitting layer-forming coating liquid 1, except that the compound 2 as a light emitting material in the light emitting layer-forming coating liquid 1 was changed to compounds 9 and 17 as the light emitting materials.

Furthermore, light emitting layer-forming coating liquids 4 to 6 were prepared, respectively, in the same manner as for the light emitting layer-forming coating liquids 1 to 3, except that the host material PH-1 in the light emitting layer-forming coating liquids 1 to 3 was changed to a host material H-2.

[Chem. 60]

(Host material PH-1)

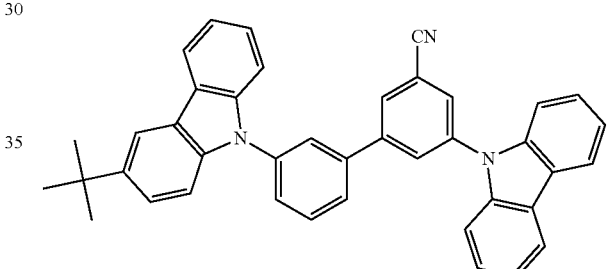

In addition, for comparison, comparative light emitting layer-forming coating liquid 1 was prepared in the same manner as for the light emitting layer-forming coating liquid 1, except that the light emitting material 2 in the light emitting layer-forming coating liquid 1 was changed to the comparative compound 3.

(Procedure for Production of Element)

—Fabrication of Organic Electroluminescent Element P1—

ITO was deposited on a 25 mm×25 mm×0.7 mm glass substrate to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the Electronics Industry (manufactured by Kanto Chemical Co., Inc.) and spin-coated (2,000 rpm, 20 seconds) to give a thickness of about 40 nm, and then dried at 120° C. for 30 minutes and subjected to an annealing treatment at 160° C. for 10 minutes to form a hole injecting layer.

[Chem. 61]

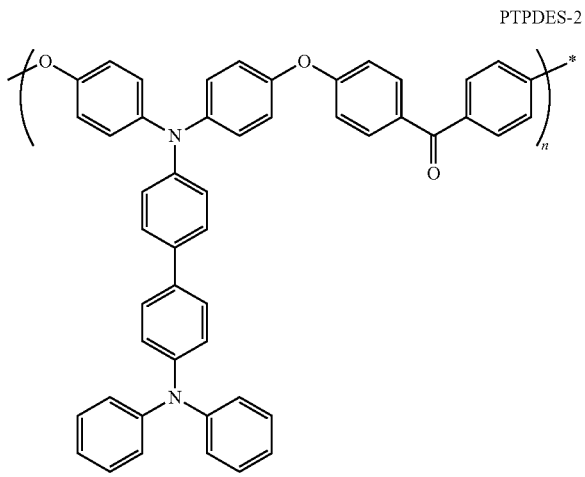

PTPDES-2

(XNR5516HV, manufactured by Nagase Chemical Co., Ltd.) to fabricate an organic electroluminescent element P1.

Organic electroluminescent elements P2 to P6 were fabricated in the same manner as for the organic electroluminescent element P1, except that the light emitting layer-forming coating liquid 1 was changed to the light emitting layer-forming coating liquids 2 to 6 in the organic electroluminescent element P1.

Furthermore, for comparison, an organic electroluminescent element P7 was fabricated in the same manner as for the organic electroluminescent element P1, except that the light emitting layer-forming coating liquid 1 was changed to the comparative light emitting layer-forming coating liquid 1 in the organic electroluminescent element P1.

The same evaluation as in Example 1 was carried out for the organic electroluminescent element P7. The results are shown in Table 7. The external quantum efficiency in Table 7 is shown as a relative value, taking the external quantum efficiency of the organic electroluminescent element, in which the comparative compound 1 is used, as 1.0.

TABLE 7

| Organic electro-luminescent element | Light emitting material | Host material | Relative external quantum efficiency | Chromaticity | Change in chromaticity after deterioration by driving | Note |
|---|---|---|---|---|---|---|
| P1 | Compound 2 | PH-1 | 1.3 | A | B | The present invention |
| P2 | Compound 9 | PH-1 | 1.3 | A | B | The present invention |
| P3 | Compound 17 | PH-1 | 1.3 | A | C | The present invention |
| P7 | Comparative Compound 1 | PH-1 | 1.0 | C | D | Comparative Example |
| P4 | Compound 2 | H-2 | 1.3 | A | B | The present invention |
| P5 | Compound 9 | H-2 | 1.3 | A | B | The present invention |
| P6 | Compound 17 | H-2 | 1.2 | A | C | The present invention |
| P8 | Comparative compound 1 | H-2 | 1.0 | C | D | Comparative Example |

The light emitting layer-forming coating liquid 1 was spin-coated on a hole injecting layer (1,300 rpm, 30 seconds) to give a thickness of about 40 nm, thereby obtaining a light emitting layer.

Subsequently, BAlq (bis-(2-methyl-8-quinolato)-4-(phenylphenolate)-aluminum (III)) represented by the following structural formula was formed as an electron transporting layer on the light emitting layer to give a thickness of 40 nm by a vacuum deposition method.

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a globe box purged with an argon gas, and then sealed with a sealing can made of stainless steel and an ultraviolet curing adhesive It could be seen from Tables 2 to 7 that the organic electroluminescent element of the present invention has high luminous efficiency, and thus, has excellent blue color purity and a small chromaticity change after deterioration by driving.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE

10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

We claim:

1. A material for an organic electroluminescent element, which is represented by the following general formula (1):

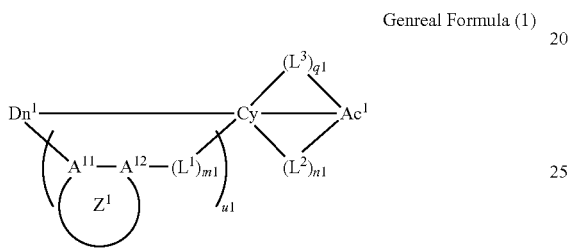

Genreal Formula (1)

wherein
Dn$^1$ represents NR$^{11}$, an O atom, or an S atom; R$^{11}$ represents a substituent, and R$^{11}$ may be bonded to Cy to form a ring other than an aromatic ring;
Ac$^1$ represents an electron absorbing substituent, an aryl group having a substituent selected from the group consisting of a halogen atom, a cyano group, and a trifluoromethyl group, or an electron deficient heteroaryl group, and Ac$^1$ may further have a substituent;
wherein the Cy is represented by pyrene which may have a substituent, has any one of the Dn$^1$ and the Ac$^1$ at the 1- or 3-position of the pyrene, and has the other of the Dn$^1$ and the Ac$^1$ at the 6- or 8-position of the pyrene, in the general formula (1);
Ring Z$^1$ represents an arylene group or a heteroarylene group, A$^{11}$ represents a carbon atom constituting the ring Z$^1$, and A$^{12}$ represents a carbon atom or a nitrogen atom constituting the ring Z$^1$;
L$^1$, L$^2$ and L$^3$ each independently represent an oxygen atom, a sulfur atom, CR$^{12}$R$^{13}$, or SiR$^{14}$R$^{15}$, and R$^{12}$, R$^{13}$, R$^{14}$ and R$^{15}$ each independently represent a hydrogen atom or a substituent;
wherein at least one of L$^1$, L$^2$, and L$^3$ is not sulfur;
u1 represents 1;
m1 represents 0 or 1, and when m1 is 0, Cy and ring Z$^1$ are directly bonded to each other;
n1 and q1 represent 0 or 1, and in the case where any one of n1 and q1 is 0 and n1 or q1 is 1, the rings formed by Cy, Ac$^1$ and L$^2$ or L$^3$ are not all aromatic rings,
wherein when Ac$^1$ is a pyridine ring, at least one of n1 and q1 is 1;
wherein at least one of the conditions (i) and (ii) is true:
(i) L$^2$ and L$^3$ are not sulfur; and
(ii) Ac$^1$ is not an aryl group substituted with fluorine.

2. An organic electroluminescent element comprising:
a substrate;
a pair of electrodes including an anode and a cathode, disposed on the substrate; and
at least one organic layer including a light emitting layer, disposed between the electrodes, wherein the organic layer includes the material according to claim 1.

3. The organic electroluminescent element according to claim 2, wherein the compound represented by the general formula (1) is a light emitting material.

4. A device using the organic electroluminescent element according to claim 2, wherein the device is selected from the group consisting of a light emitting device, a display device, or an illumination device.

5. The material according to claim 1, wherein Ac$^1$ is not an aryl group substituted with fluorine.

6. A material for an organic electroluminescent element, which is represented by any one of the following general formulae (2) to (5):

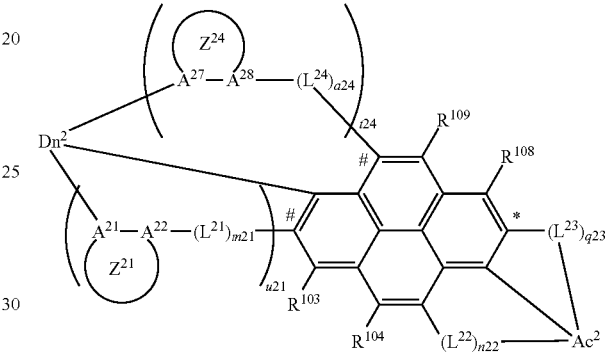

General formula (2)

wherein Dn$^2$ represents an N atom, an O atom, or an S atom, and in the case where Dn$^2$ represents an O atom or an S atom, the sum of u21 and t24 is 0 or 1, wherein in the case where Dn$^2$ represents an N atom, at least one of u21 and t24 represents 0, or wherein in the case where Dn$^2$ represents an O atom or an S atom, u21 and t24 are both 0, Dn$^2$ further has a substituent;
Ac$^2$ represents an electron absorbing substituent, an aryl group having an electron absorbing substituent, or an electron deficient heteroaryl group, and Ac$^2$ may further have a substituent;
Ring Z$^{21}$ and ring Z$^{24}$ each independently represents an arylene group or a heteroarylene group, A$^{21}$ represents a carbon atom constituting the ring Z$^{21}$, A$^{22}$ represents a carbon atom or a nitrogen atom constituting the ring Z$^{21}$, A$^{27}$ represents a carbon atom constituting the ring Z$^{24}$, and A$^{28}$ represents a carbon atom or a nitrogen atom constituting the ring Z$^{24}$;
R$^{103}$, R$^{104}$, R$^{108}$ and R$^{109}$ each independently represent a hydrogen atom or a substituent;
L$^{21}$, L$^{22}$, L$^{23}$ and L$^{24}$ each independently represent an oxygen atom, a sulfur atom, CR$^{22}$R$^{23}$, or SiR$^{24}$R$^{25}$, and R$^{22}$, R$^{23}$, R$^{24}$ and R$^{25}$ each independently represent a hydrogen atom or substituent;
wherein at least one of L$^{21}$, L$^{22}$, L$^{23}$, and L$^{24}$ is not sulfur;
u21 represents 0 or 1, and in the case where u21 is 0, the #positions of the pyrene ring and Dn$^2$ are not bonded to each other;
t24 represents 0 or 1, in the case where t24 is 0, the #positions of the pyrene ring and Dn$^2$ are not bonded to each other;
m21 represents 0 or 1, and when m21 is 0 and u21 is 1, #positions of pyrene ring and ring Z$^{21}$ are directly bonded to each other;

s24 represents 0 or 1, and when s24 is 0 and u24 is 1, the #positions of pyrene ring and ring $Z^{24}$ are directly bonded to each other;

n22 and q23 represent 0 or 1, in the case where any one of n22 and q23 is 0 and n22 or q23 is 1, the rings formed by the pyrene ring, $Ac^2$ and $L^{22}$ or $L^{23}$ are not all aromatic rings; wherein the case where n22 or q23 is 0, the * positions of the pyrene ring and $Ac^2$ are not bonded to each other wherein when $Ac^2$ is a pyridine ring, at least one of n22 and q23 is 1;

General formula (3)

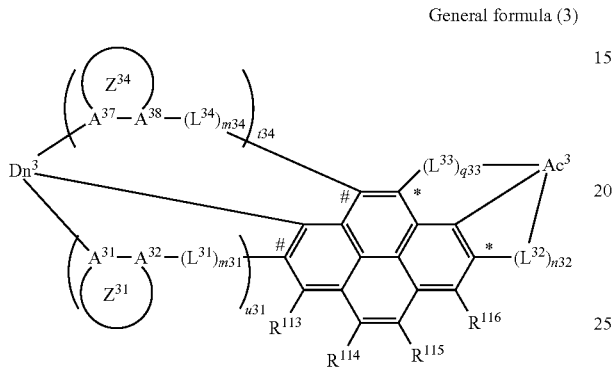

wherein $Dn^3$ represents an N atom, an O atom, or an S atom, and in the case where $Dn^3$ represents an O atom or an S atom, the sum of u31 and t34 is 0 or 1; where when $Dn^3$ represents an N atom, at least one of u31 and t34 represents 0, and when in the case where u31 and t34 are each 0, $Dn^3$ further has two substituents, or when in the case where one of u31 and t34 is 1, then $Dn^3$ further has one substituent; or when in the case where $Dn^3$ represents an O atom or an S atom and u31 and t34 are both 0, $Dn^3$ further has a substituent;

$Ac^3$ represents an electron absorbing substituent, an aryl group having an electron absorbing substituent, or an electron deficient heteroaryl group, and $Ac^3$ may further have a substituent;

Ring $Z^{31}$ and the ring $Z^{34}$ each independently represent an arylene group or a heteroarylene group, $A^{31}$ represents a carbon atom constituting ring $Z^{31}$, and $A^{32}$ represents a carbon atom or a nitrogen atom constituting ring $Z^{31}$, $A^{37}$ represents a carbon atom constituting ring $Z^{34}$, and $A^{38}$ represents a carbon atom or a nitrogen atom constituting ring $Z^{34}$;

$R^{113}$, $R^{114}$, $R^{115}$ and $R^{116}$ each independently represent a hydrogen atom or a substituent;

$L^{31}$, $L^{32}$, $L^{33}$ and $L^{34}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent hydrogen or a substituent;

u31 represents 1;

t34 represents 0 or 1, and in the case where t34 is 0, the #positions of the pyrene ring and $Dn^3$ are not bonded to each other;

m31 represents 0 or 1, and when m31 is 0 and u31 is 1, the #positions of the pyrene ring and ring $Z^{31}$ are directly bonded to each other;

m34 represents 0 or 1 and when m34 is 0 and t34 is 1, the #positions of the pyrene ring and ring $Z^{34}$ are directly bonded to each other;

n32 and q33 represent 0 or 1, and in the case where any one of n32 and q33 is 0 and n32 or q33 is 1, the rings formed by the pyrene ring, $Ac^3$ and $L^{32}$ or $L^{33}$ are not all aromatic rings; where when n32 or q33 is 0, the * positions of the pyrene ring and $Ac^3$ are not bonded to each other, wherein when $Ac^3$ is a pyridine ring, at least one of n32 and q33 is 1;

General formula (4)

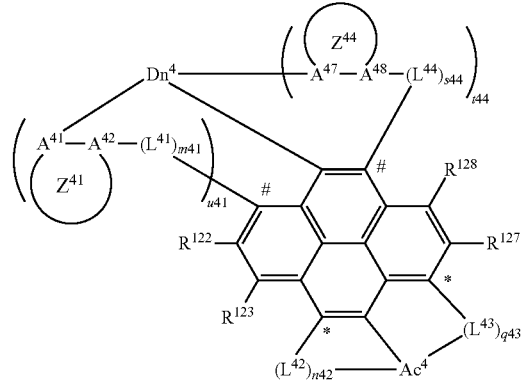

wherein $Dn^4$ represents an N atom, an O atom, or an S atom, and in the case where $Dn^4$ represents an O atom or an S atom, the sum of u41 and t44 is 0 or 1; when in the case where $Dn^4$ represents an N atom and at least one of u41 and t44 represents 0, and when in the case where u41 and t44 are each 0, $Dn^4$ further has two substituents, or when in the case where one of u41 and t44 is 1, then $Dn^4$ further has one substituent; or when in the case where $Dn^4$ represents an O atom or an S atom, u41 and t44 are both 0, $Dn^4$ further has a substituent;

$Ac^4$ represents an electron absorbing substituent, an aryl group having an electron absorbing substituent, or an electron deficient heteroaryl group, and $Ac^4$ may further have a;

Ring $Z^{41}$ and the ring $Z^{44}$ each independently represent an arylene group or a heteroarylene group, $A^{41}$ represents a carbon atom constituting ring $Z^{41}$, $A^{42}$ represents a carbon atom or a nitrogen atom constituting ring $Z^{41}$, $A^{47}$ represents a carbon atom constituting ring $Z^{44}$, and $A^{48}$ represents a carbon atom or a nitrogen atom constituting ring $Z^{44}$;

$R^2$, $R^3$, $R^7$ and $R^8$ each independently represent a hydrogen atom or a substituent;

$L^{41}$, $L^{42}$, $L^{43}$ and $L^{44}$ each independently represent an oxygen atom, a sulfur atom, $CR^{42}R^{43}$, or $SiR^{44}R^{45}$, and $R^{42}$, $R^{43}$, $R^{44}$ and $R^{45}$ each independently represent a hydrogen atom or a substituent;

u41 represents 0 or 1, and in the case where u41 is 0, the #positions of the pyrene ring and $Dn^4$ are not bonded to each other;

t44 represents 0 or 1, and in the case where t44 is 0, the #positions of the pyrene ring and $Dn^4$ are not bonded to each other;

m41 represents 0 or 1, and when m41 is 0 and u41 is 1, the #positions of the pyrene ring and ring $Z^{41}$ are directly bonded to each other;

m44 represents 0 or 1, and when m44 is 0 and t44 is 1, the #positions of the pyrene ring and the ring $Z^{44}$ are directly bonded to each other;

n42 and q43 represents 0 or 1, and in the case where any one of n42 and q43 is 0 and n42 or q43 is 1, the rings formed by the pyrene ring, $Ac^4$ and $L^{42}$ or $L^{43}$ are not all aromatic rings; in the case where n42 or q43 is 0, the * positions of the pyrene ring and $Ac^4$ are not bonded to each other wherein when $Ac^4$ is a pyridine ring, at least one of n42 and q43 is 1;

General formula (5)

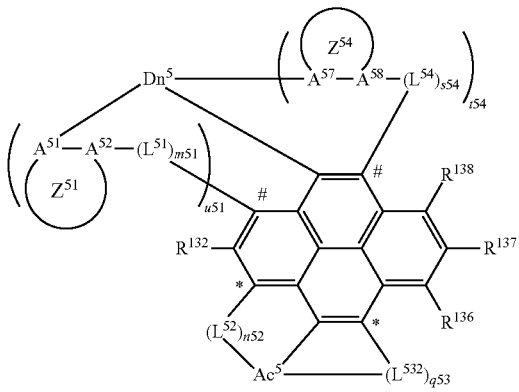

wherein $Dn^5$ represents an N atom, an O atom, or an S atom, in the case where $Dn^5$ represents an O atom or an S atom, the sum of u51 and t54 is 0 or 1 where when $Dn^5$ represents an N atom, at least one of u51 and t54 represents 0, and when in the case where u51 and t54 are each 0, $Dn^5$ further has two substituents, or when in the case where one of u51 and t54 is 1, then $Dn^5$ further has one substituent; or when in the case where $Dn^5$ represents an O atom or an S atom, u51 and t54 are both 0, $Dn^5$ further has a substituent;

$Ac^5$ represents an electron absorbing substituent, an aryl group having an electron absorbing substituent, or an electron deficient heteroaryl group, $Ac^5$ may further have a substituent;

Ring $Z^{51}$ and ring $Z^{54}$ each independently represent an arylene group or a heteroarylene group, $A^{51}$ represents a carbon atom constituting the ring $Z^{51}$, $A^{52}$ represents a carbon atom or a nitrogen atom constituting the ring $Z^{51}$, $A^{57}$ represents a carbon atom constituting ring $Z^{54}$, and $A^{58}$ represents a carbon atom or a nitrogen atom constituting ring $Z^{54}$;

$R^2$, $R^6$, $R^7$ and $R^8$ each independently represent a hydrogen atom or a substituent;

$L^{51}$, $L^{52}$, $L^{53}$ and $L^{54}$ each independently represent an oxygen atom, a sulfur atom, $CR^{52}R^{53}$, or $SiR^{54}R^{55}$, and $R^{52}$, $R^{53}$, $R^{54}$ and $R^{55}$ each independently represent a hydrogen atom or a substituent;

u51 represents 0 or 1, and in the case where u51 is 0, the #positions of the pyrene ring and $Dn^5$ are not bonded to each other;

t54 represents 0 or 1, and in the case where t54 is 0, the #positions of the pyrene ring and $Dn^5$ are not bonded to each other;

m51 represents 0 or 1, and when m51 is 0 and u51 is 1, the #positions of the pyrene ring and ring $Z^{51}$ are directly bonded to each other;

m54 represents 0 or 1, and when m54 is 0 and t54 is 1, the #positions of the pyrene ring and ring $Z^{54}$ are directly bonded to each other;

n52 and q53 represent 0 or 1, and in the case where any one of n52 and q53 is 0 and n52 or q53 is 1, the rings formed by the pyrene ring, $Ac^5$ and $L^{52}$ or $L^{53}$ are not all aromatic rings wherein in the case where n52 or q53 is 0, the * positions of the pyrene ring and $Ac^5$ are not bonded to each other, wherein when $Ac^5$ is a pyridine ring, at least one of n52 and q53 is 1.

7. The material according to claim 6, wherein the compound is represented by the general formula (2) and is a compound represented by the following general formula (6):

General formula (6)

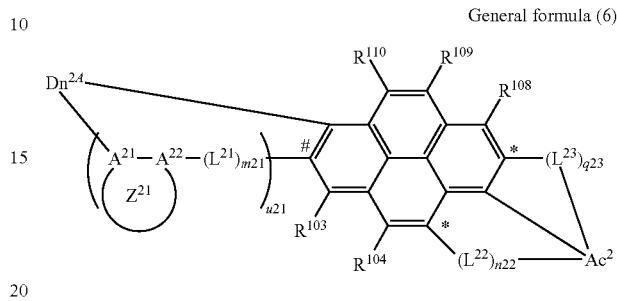

wherein $Dn^{24}$ represents $NR^{114}$, an O atom, or an S atom, and when u21 represents 0, $Dn^{24}$ further has a substituent; $R^{114}$ represents a substituent;

$Ac^2$ represents an electron absorbing substituent, an aryl group having an electron absorbing substituent, or an electron deficient heteroaryl group, $Ac^2$ may further have a substituent;

Ring $Z^{21}$ represents an arylene group or a heteroarylene group, $A^{21}$ represents a carbon atom constituting the ring $Z^{21}$, $A^{22}$ represents a carbon atom or a nitrogen atom constituting ring $Z^{21}$;

$R^{103}$, $R^{104}$, $R^{108}$, $R^{109}$ and $R^{110}$ each independently represent a hydrogen atom or a substituent;

$L^{21}$, $L^{22}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent;

wherein at least one $L^{21}$, $L^{22}$, and $L^{23}$ is not sulfur;

u21 represents 0 or 1, and in the case where u21 is 0, the #positions of the pyrene ring and $Dn^{24}$ are not bonded to each other;

m21 represents 0 or 1, and when m21 is 0 and u21 is 1, the #positions of the pyrene ring and the ring $Z^{21}$ are directly bonded to each other;

n22 and q23 represent 0 or 1, and in the case where any one of n22 and q23 is 0 and n22 or q23 is 1, the rings formed by the pyrene ring, $Ac^2$ and $L^{22}$ or $L^{23}$ are not all aromatic rings, wherein in the case where n22 or q23 is 0, the * positions of the pyrene ring and $Ac^2$ are not bonded to each other, wherein when $Ac^2$ is a pyridine ring, at least one of n22 and q23 is 1.

8. The material according to claim 7, wherein the compound is represented by the general formula (6) and is a compound represented by the following general formula (8):

General formula (8)

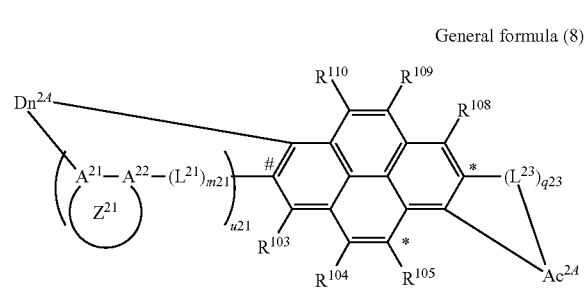

wherein $Dn^{24}$ represents $NR^{114}$, an O atom, or an S atom, and when u21 represents 0, $Dn^{24}$ further has a substituent; $R^{114}$ represents a substituent;

$Ac^{24}$ represents an electron absorbing substituent, an aryl group having an electron absorbing substituent, or an electron deficient heteroaryl group, $Ac^{24}$ may further have a substituent;

Ring $Z^{21}$ represents an arylene group or a heteroarylene group, $A^{21}$ represents a carbon atom constituting the ring $Z^{21}$, and $A^{22}$ represents a carbon atom or a nitrogen atom constituting the ring $Z^{21}$;

$R^{103}$, $R^{104}$, $R^{105}$, $R^{108}$, $R^{109}$ and $R^{110}$ each independently represent a hydrogen atom or a substituent;

$L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent;

wherein at least one of $L^{21}$ and $L^{23}$ is not sulfur;

u21 represents 0 or 1, and in the case where u21 is 0, the #positions of the pyrene ring and $Dn^{24}$ are not bonded to each other;

m21 represents 0 or 1, when m21 is 0 and u21 is 1, the #positions of the pyrene ring and the ring 721 are directly bonded to each other;

q23 represents 0 or 1, and in the case where q23 is 1, the rings formed by the pyrene ring, $Ac^{24}$ and $L^{23}$ are not all aromatic rings where when q23 is 0, the * positions of the pyrene ring and $Ac^{24}$ are not bonded to each other wherein when $Ac^{24}$ is a pyridine ring, q23 is 1.

9. The material according to claim 8, wherein the compound is represented by the general formula (8) and is a compound represented by the following general formula (10):

General formula (10)

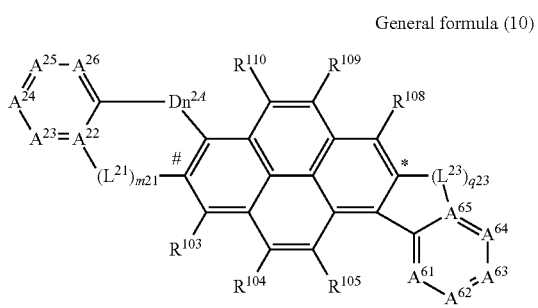

wherein $Dn^{24}$ represents $NR^{114}$, an O atom, or an S atom, and $R^{114}$ represents a substituent;

$A^{22}$ represents a C atom; $A^{23}$, $A^{24}$, $A^{25}$, $A^{26}$, $A^{61}$, $A^{62}$, $A^{63}$, $A^{64}$ and $A^{65}$ each independently represent CRzs or an N atom; when in the case where q23 is 1, $A^{65}$ represents CRz; wherein Rz represents a hydrogen atom or a substituent, and two adjacent CRzs may be combined with each other to form a 5- or 6-membered ring; where when $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent;

$R^{103}$, $R^{104}$, $R^{105}$, $R^{108}$, $R^{109}$ and $R^{110}$ each independently represent a hydrogen atom or a substituent;

$L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent;

wherein at least one of $L^{21}$ and $L^{23}$ is not sulfur;

m21 represents 0 or 1, and when m21 is 0, the #positions of the pyrene ring and $A^{22}$ are directly bonded to each other;

q23 represents 0 or 1, and in the case where q23 is 0, the * positions of the pyrene ring and $A^{65}$ are not bonded to each other, wherein in the case where only one of $A^{61}$, $A^{62}$, $A^{63}$, $A^{64}$ and $A^{65}$ is an N atom, q23 represents 1.

10. The material according to claim 9, wherein the compound is represented by the general formula (10) and is a compound represented by the following general formula (12):

General formula (12)

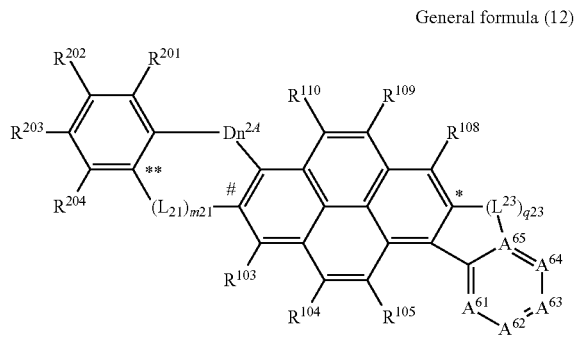

wherein $Dn^{24}$ represents $NR^{114}$, an O atom, or an S atom, and $R^{114}$ represents a substituent;

$A^{61}$, $A^{62}$, $A^{63}$, $A^{64}$ and $A^{65}$ each independently represent CRzs or an N atom; when in the case where q23 is 1, $A^{65}$ represents CRz; wherein Rz represents a hydrogen atom or a substituent, and two adjacent CRzs may be combined with each other to form a 5- or 6-membered ring; where when $A^{61}$, $A^{62}$, $A^{63}$, $A^{64}$ and $A^{65}$ are not all N atoms, at least one Rz in CRzs represented by $A^{61}$, $A^{62}$, $A^{63}$, $A^{64}$ and $A^{65}$ represents an electron absorbing substituent;

$R^{103}$, $R^{104}$, $R^{105}$, $R^{108}$, $R^{109}$, $R^{110}$, $R^{201}$, $R^{202}$, $R^{203}$ and $R^{204}$ each independently represent a hydrogen atom or a substituent;

$L^{21}$ and $L^{23}$ each independently represent an oxygen atom, a sulfur atom, $CR^{22}R^{23}$, or $SiR^{24}R^{25}$, and $R^{22}$, $R^{23}$, $R^{24}$ and $R^{25}$ each independently represent a hydrogen atom or a substituent;

wherein at least one of $L^{21}$ and $L^{23}$ is not sulfur;

m21 represents 0 or 1, and when m21 is 0, the ** position and the #position of the pyrene ring are directly bonded to each other;

q23 represents 0 or 1, and in the case where q23 is 0, the * positions of the pyrene ring and $A^{65}$ are not bonded to each other, wherein in the case where only one of $A^{61}$, $A^{62}$, $A^{63}$, $A^{64}$ and $A^{65}$ is an N atom, q23 is 1.

11. The material according to claim 6, wherein the compound is represented by the general formula (3) and is a compound represented by the following general formula (7):

General formula (7)

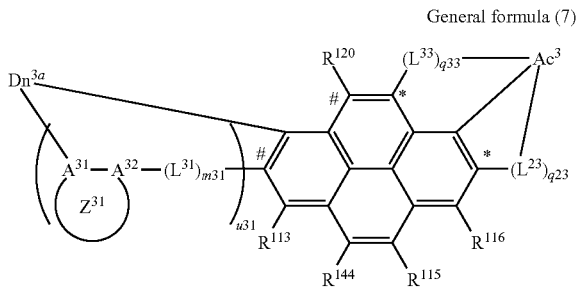

wherein $Dn^{3A}$ represents $NR^{11B}$, an O atom, or an S atom, and when u31 represents 0, $Dn^{3A}$ further has a substituent; $R^{11B}$ represents a substituent;

$Ac^3$ represents an electron absorbing substituent, an aryl group having an electron absorbing substituent, or an electron deficient heteroaryl group, $Ac^3$ may further have a substituent;

Ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$;

$R^{113}$, $R^{114}$, $R^{115}$, $R^{116}$ and $R^{120}$ each independently represent a hydrogen atom or a substituent;

$L^{31}$, $L^{32}$ and $L^{33}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent;

wherein at least one of $L^{31}$, $L^{32}$, and $L^{33}$ is not sulfur;

u31 represents 1;

m31 represents 0 or 1, and when m31 is 0 and u31 is 1, the #positions of the pyrene ring and the ring $Z^{31}$ are directly bonded to each other;

n32 and q33 represent 0 or 1, and in the case where any one of n32 and q33 is 0 and n32 or q33 is 1, the rings formed by the pyrene ring, $Ac^3$ and $L^{32}$ or $L^{33}$ are not all aromatic rings, wherein in the case where n32 or q33 is 0, the * positions of the pyrene ring and $Ac^3$ are not bonded to each other, wherein when $Ac^3$ is a pyridine ring, at least one of n32 and q33 is 1.

12. The material according to claim 11, wherein the compound is represented by the general formula (7) and is a compound represented by the following general formula (9):

General formula (9)

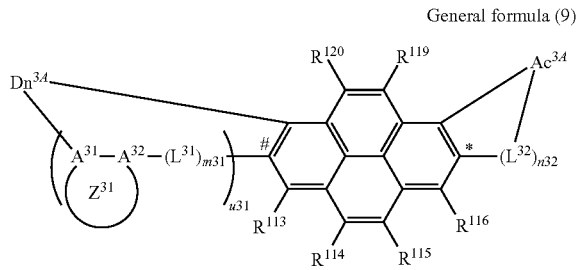

wherein $Dn^{3A}$ represents $NR^{11B}$, an O atom, or an S atom, and when u31 represents 0, $Dn^{3A}$ further has a substituent; $R^{11B}$ represents a substituent;

$Ac^{3A}$ represents an electron absorbing substituent, an aryl group having an electron absorbing substituent, or an electron deficient heteroaryl group, $Ac^{3A}$ may further have a substituent;

Ring $Z^{31}$ represents an arylene group or a heteroarylene group, $A^{31}$ represents a carbon atom constituting the ring $Z^{31}$, and $A^{32}$ represents a carbon atom or a nitrogen atom constituting the ring $Z^{31}$;

$R^{113}$, $R^{114}$, $R^{115}$, $R^{116}$, $R^{119}$ and $R^{120}$ each independently represent a hydrogen atom or a substituent;

$L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent;

wherein at least one of $L^{31}$ and $L^{32}$ is not sulfur;

u31 represents 1;

m31 represents 0 or 1, and when m31 is 0 and u31 is 1, the #positions of the pyrene ring and the ring $Z^{31}$ are directly bonded to each other;

n32 represents 0 or 1, and in the case where n32 is 1, the rings formed by the pyrene ring, $Ac^{3A}$ and $L^{32}$ are not all aromatic rings, wherein in the case where n32 is 0, the * positions of the pyrene ring and $Ac^{3A}$ are not bonded to each other, wherein when $Ac^{3A}$ is a pyridine ring, n32 is 1.

13. The material according to claim 12, wherein the compound is represented by the general formula (9) and is a compound represented by the following general formula (11):

General formula (11)

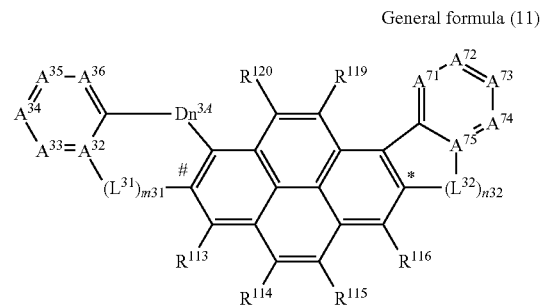

wherein $Dn^{3A}$ represents $NR^{11B}$, an O atom, or an S atom, and $R^{11B}$ represents a substituent;

$A^{32}$ represents a C atom; $A^{33}$, $A^{34}$, $A^{35}$, $A^{36}$, $A^{71}$, $A^{72}$, $A^{73}$, $A^{74}$ and $A^{75}$ each independently represent CRz' or an N atom; when in the case where n32 is 1, $A^{75}$ represents CRz'; wherein Rz' represents a hydrogen atom or a substituent, and two adjacent CRz's may be combined with each other to form a 5- or 6-membered ring; where when $A^{71}$, $A^{72}$, $A^{73}$, $A^{74}$ and $A^{75}$ are not all N atoms, at least one Rz' in CRz's represented by $A^{71}$, $A^{72}$, $A^{73}$, $A^{74}$ and $A^{75}$ represents an electron absorbing substituent;

$R^{113}$, $R^{114}$, $R^{115}$, $R^{116}$, $R^{119}$ and $R^{120}$ each independently represent a hydrogen atom or a substituent;

$L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent;

wherein at least one of $L^{31}$ and $L^{32}$ is not sulfur;

m31 represents 0 or 1, and when m31 is 0, the #positions of the pyrene ring and $A^{32}$ are directly bonded to each other;

n32 represents 0 or 1, and in the case where n32 is 1, the rings formed by the pyrene ring, $Ac^{3A}$ and $L^{32}$ are not all aromatic rings; in the case where n32 is 0, the * positions of the pyrene ring and $A^{75}$ are not bonded to each other, wherein in the case where only one of $A^{71}$, $A^{72}$, $A^{73}$, $A^{74}$ and $A^{75}$ is an N atom, n32 represents 1.

14. The material according to claim 13, wherein the compound is represented by the general formula (11) and is a compound represented by the following general formula (13):

General formula (13)

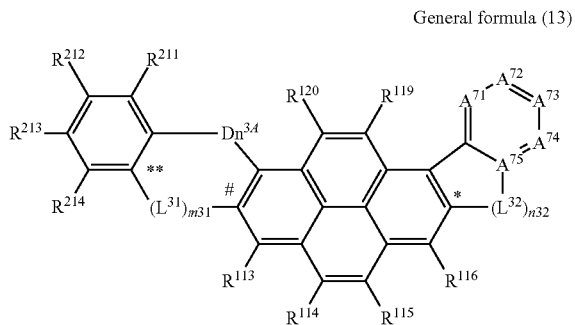

wherein $Dn^{34}$ represents $NR^{11B}$, an O atom, or an S atom, and $R^{11B}$ represents a substituent;

$A^{71}$, $A^{72}$, $A^{73}$, $A^{74}$ and $A^{75}$ each independently represent CRz' or an N atom; when in the case where n32 is 1, $A^{75}$ represents CRz'; wherein Rz' represents a hydrogen atom or a substituent, and two adjacent CRz's may be combined with each other to form a 5- or 6-membered ring; where when $A^{71}$, $A^{72}$, $A^{73}$, $A^{74}$ and $A^{75}$ are not all N atoms, at least one Rz' in CRz's represented by $A^{71}$, $A^{72}$, $A^{73}$, $A^{74}$ and $A^{75}$ represents an electron absorbing substituent;

$R^{113}$, $R^{114}$, $R^{115}$, $R^{116}$, $R^{119}$, $R^{120}$, $R^{211}$, $R^{212}$, $R^{213}$ and $R^{214}$ each independently represents a hydrogen atom or a substituent;

$L^{31}$ and $L^{32}$ each independently represent an oxygen atom, a sulfur atom, $CR^{32}R^{33}$, or $SiR^{34}R^{35}$, and $R^{32}$, $R^{33}$, $R^{34}$ and $R^{35}$ each independently represent a hydrogen atom or a substituent;

wherein at least one of $L^{31}$ and $L^{32}$ is not sulfur;

m31 represents 0 or 1, and when m31 is 0, the * position and the #position of the pyrene ring are directly bonded to each other;

n32 represents 0 or 1, and in the case where n32 is 0, the * positions of the pyrene ring and $A^{75}$ are not bonded to each other, wherein in the case where only one of $A^{71}$, $A^{72}$, $A^{73}$, $A^{74}$ and $A^{75}$ is an N atom, n32 represents 1.

15. An organic electroluminescent element comprising:
a substrate;
a pair of electrodes including an anode and a cathode, disposed on the substrate; and
at least one organic layer including a light emitting layer, disposed between the electrodes, wherein the organic layer includes a compound according to claim 6.

16. An organic electroluminescent element comprising:
a substrate;
a pair of electrodes including an anode and a cathode, disposed on the substrate; and
at least one organic layer including a light emitting layer, disposed between the electrodes, wherein the organic layer includes a compound according to claim 6.

* * * * *